US007723019B2

(12) United States Patent
Moscow et al.

(10) Patent No.: US 7,723,019 B2
(45) Date of Patent: May 25, 2010

(54) ORGANIC CATION TRANSPORTER PREFERENTIALLY EXPRESSED IN HEMATOPOIETIC CELLS AND LEUKEMIAS AND USES THEREOF

(75) Inventors: Jeffrey Moscow, Lexington, KY (US); Xin Lu, Shanghai (CN); Craig Jordan, Rochester, NY (US)

(73) Assignee: University of Kentucky Research Foundation, Lexington, KY (US)

(*) Notice: Subject to any disclaimer, the term of this patent is extended or adjusted under 35 U.S.C. 154(b) by 451 days.

(21) Appl. No.: 11/521,487

(22) Filed: Sep. 15, 2006

(65) Prior Publication Data

US 2007/0269846 A1 Nov. 22, 2007

Related U.S. Application Data

(62) Division of application No. 10/849,551, filed on May 20, 2004, now abandoned.

(60) Provisional application No. 60/471,709, filed on May 20, 2003.

(51) Int. Cl.
*C12Q 1/00* (2006.01)
*G01N 33/53* (2006.01)
*C07K 14/435* (2006.01)

(52) U.S. Cl. .......................................... 435/4; 530/350

(58) Field of Classification Search ....................... None
See application file for complete search history.

(56) References Cited

U.S. PATENT DOCUMENTS 7,045,316 B2 * 5/2006 Nezu et al. ................. 435/69.1
2003/0009024 A1 * 1/2003 Curtis ....................... 536/23.5

FOREIGN PATENT DOCUMENTS

WO WO-0246415 A2 * 6/2002

OTHER PUBLICATIONS

Gong et al. Identification of OCT6 as a novel organic cation transporter preferentially expressed in hematopoietic cells and leukemias. Exp Hematol 30: 1162-1169, 2002.*
Strober, W. Trypan Blue Exclusion Test for Cell Viability. Curr Prot Immunol Supplement 21: A.3B.1-A.3B.2, Mar. 1997.*
Okabe et al. Genbank Accession No. AAK58593, Jun. 2, 2001; 2 pages.*
Fischer G., Biochem. Pharmacol. "Short Communications" vol. 11: pp. 1233-1234, Pergamon Press Ltd., 1962.
Moscow, et al., "Isolation of a Gene Encoding a Human Reduced Folate Carrier (RFC1) and Analysis of Its Expression in Transport-deficient, Methotrexate-resistant Human Breast Cancer Cells" Cancer Res. 55: pp. 3790-3794, 1995.
Moscow et al., "Reduced Folate Carrier Gene (RFC1) Expression and Anti-Folate Resistance in Transfected and Non-Selected Cell Lines" Int J Cancer. 72: pp. 184-190, 1997.
Koepsell et al., "Organic Cation Transporters in Intestine, Kidney, Liver, and Brain" Ann. Rev. Physiol. 60: pp. 243-266, 1998.
Burckhardt, et al., "Structure of renal organic anion and cation transporters" Am J Physiol Renal Physiol. 278: pp. F853-F866., 2000.
Wu, et al., "Identity of the Organic Cation Transporter OCT3 as the Extraneuronal Monoamine Transporter (uptake$_2$) and Evidence for the Expression of the Transporter in the Brain" J Biol Chem. 273: pp. 32776-32786, 1998.
Dhillon et al. Clin Pharmacol Ther. 65: p. 205, 1996.
Koyama et al., "CD63, a Member of Tetraspan Transmembrane Protein Family, Induces Cellular Spreading by Reaction with Monoclonal Antibody on Substrata" Biochem Biophys Res Commun. 246: pp. 841-846, 1998.
Moscow, J. A., Schneider, E. S., Ivy, S. P., and Cowan, K. H. "Multidrug resistance" In: H. M. Pinedo, D. L. Longo, and B. A. Chabner (eds.), Cancer chemotherapy and biological response modifiers. Annual 17. New York: Elsevier, pp. 139-177, 1997.
Okabe et al., GenBank AF268892, Jun. 2, 2001.
Waterston et al., GenBank AC002464, Feb 4, 2000.
NCI-CGAP et al., GenBank AI040384, Aug 28, 1998.
Hillier et al., GenBank AA033971, May 9, 1997.
Hillier et al., GenBank H70190, Oct 24, 1995.
Tannock and Hill, The Basic Science of Oncology, 1998, New York: McGraw-Hill, pp. 53-70 and 396-410.
Hirose et al. Multidrug resistance in hematological malignancy, J. Med. Invest. 50: 126-135, 2003.
Vogelstein et al. The multistep nature of cancer, Trends Genet 9(4):138-141, 1993.
Voliotis et al. Challenge in treating hematologic malignancies, Semin Oncol 29(3 Suppl 8): 30-39, 2002.

* cited by examiner

*Primary Examiner*—Bridget E Bunner
(74) *Attorney, Agent, or Firm*—McDermott Will & Emery LLP

(57) ABSTRACT

A novel organic cation transporter (OCT) gene, OCT 6, and use thereof is described. The OCT6 gene is preferentially expressed in human hematopoietic tissues, including CD34+ cells and leukemia cells. Its narrow tissue distribution, substrate specificity, and close homology to other cell membrane transporters make OCT6 an attractive target for the treatment of myeloid diseases.

7 Claims, 10 Drawing Sheets

```
                                   10         20         30         40
SEQ ID NO. 2   OCT6   MGSRHFEGIYDHVGHFGRFQRVLYFICAFQNISCGIHYLASVFMGVTPH
SEQ ID NO. 4   OCTN1     MRDYDEVIAFLGEWGPFQRLIFFLLSASIIPNGFNGMSVVFLAGTPE
SEQ ID NO. 5   OCT3      MAQFVQVLAEIGDFGRFQIQLLILLCVLNFLSPFYFFAHVFMVLDEP
SEQ ID NO. 6   OCTN2     MRDYDEVTAFLGEWGPFQRLIFFLLSASIIPNGFTGLSSVFLIATPE
SEQ ID NO. 7   OCT2     MPTTVDDVLEHGGEFHFFQKQMFFLLALLSATFAPIYVGIVFLGFTPD
SEQ ID NO. 8   OCT1     MPTTVDDILEQVGESGWFQKQAFLILCLLSAAFAPICVGIVFLGFTPD
SEQ ID NO. 9   OAT5        MAFEELLSQVGGLGRFQMLHLVFILPSLMLLIPHILLENFAAAIPG
SEQ ID NO. 10  OAT4        MAFSKLLEQAGGVGLFQTLQVLTFILPCLMIPSQMLLENFSAAIPG
SEQ ID NO. 11  OAT3        MTFSBILDRVGSMGHFQFLHVAILGLPILNMANHNLLQIFTAATPV
SEQ ID NO. 12  OAT1        MAFNDLLQQVGGVGRFQQIQVTLVVLPLLLMASHNTLQNFTAAIPT
                            .F..L..G G FQ..   .L..  .     .  VF.  TP

       50        60        70        80        90        100
       HVCRPPGNVSQVVFHNHSNWSLEDTGALLSSGQKDYVTVQLQNGEIWELSR
       HRCRVPD------ANLSS--AWR-----------NNSVPLRLRDGREV-PHS
       HHCAVAW------VKNHTFN------LSA----AEQLVLSVPLDTAGHPEP
       HRCRVPD------ANLSS--AWR-----------NHTVPLRLRDGREV-PHS
       HRCRSPG------VAELSLRCGWSPAEEL----NYTVPGPGPAGEAS-PRQ
       HHCQSPG------VAELSQRCGWSPAEEL----NYTVPGLGPAGEAF-LGQ
       HRCWVHM------LDNNTGSGNETGILSE----DALLRISIPLDSNLRPEK
       HRCWTHM------LDNGS---AVSTNMTP----KALLTISIPPGPNQGPHQ
       HHCRPPH------NASTG-----------------PWVLPMGPNGKPER
       HHCRPPA------DANLSK---------------NGGLEVWLPRDRQGQPES
       H.CR P       AN S                    .  .P G    P
```

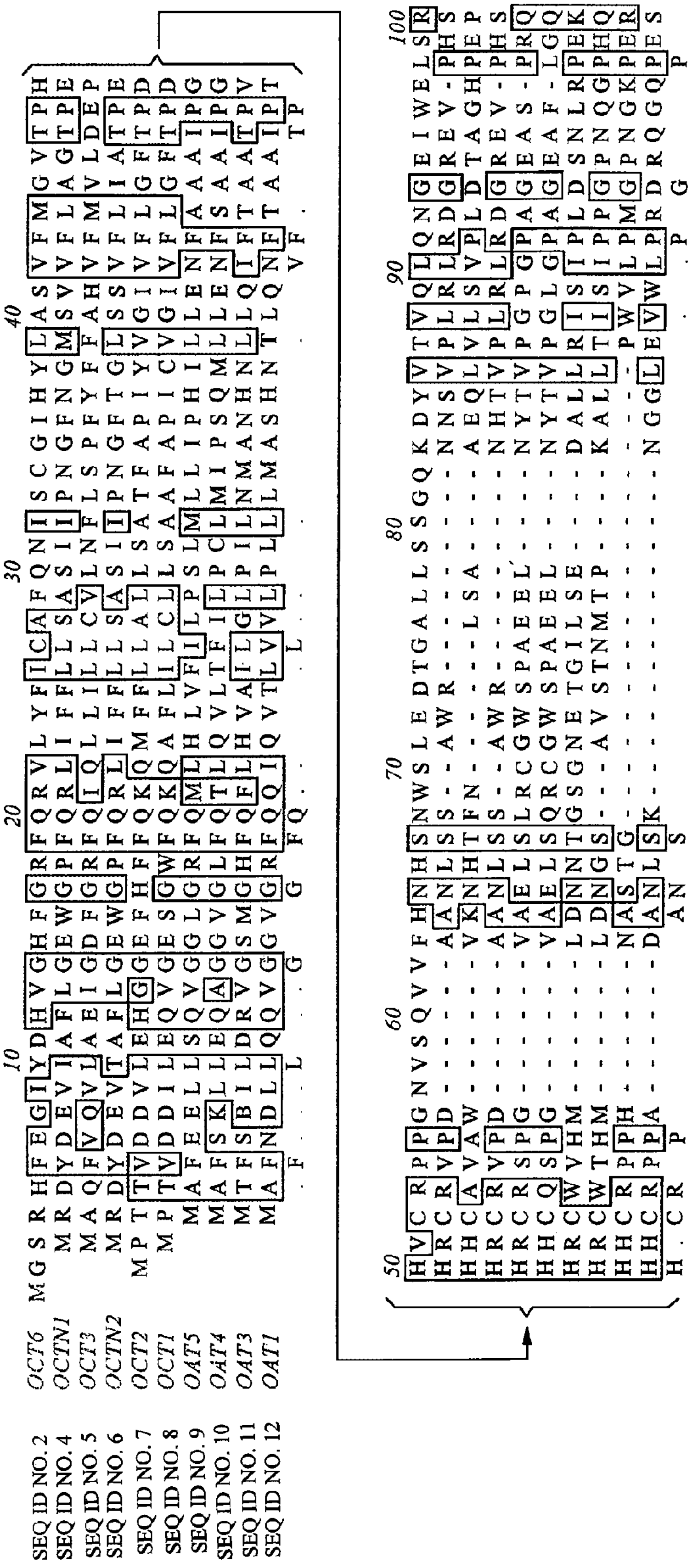

FIG. 2A

```
                                       110                 120                 130                 140
SEQ ID NO. 2   OCT6    C S R N K R E N - - - - - - - - - T S S L G Y E Y T G S K K E - F P C V D G Y I Y D Q N T W K
SEQ ID NO. 4   OCTN1   C S R Y R L A T - I A N F S A L G L E P G R D V D L G Q L E Q E S C L D G W E F S Q D V Y L
SEQ ID NO. 5   OCT3    C L M F R P P P - - - - - - - A N A S L Q D I L S H R F N E T Q P C D M G W E Y P - E N R L
SEQ ID NO. 6   OCTN2   C R R Y R L A T - I A N F S A L G L E P G R D V D L G Q L E Q E S C L D G W E F S Q D V Y L
SEQ ID NO. 7   OCT2    C R R Y E V D W N Q S T F D C V D P L A S L D T N R S R L P L G P C R D G W V Y - - E T P G
SEQ ID NO. 8   OCT1    C R R Y E V D W N Q S A L S C V D P L A S L A T N R S H L P L G P C Q D G W V Y - - D T P G
SEQ ID NO. 9   OAT5    C R F F V H P Q - - - - - W Q L L H L N G - I H S T S E A D T E P C V D G W V Y D Q S Y F P
SEQ ID NO. 10  OAT4    C R R F R Q P Q - - - - - W Q L L D P N A T A T S W S E A D T E P C V D G W V Y D R S V F T
SEQ ID NO. 11  OAT3    C L R F V H P P - - - - - N - - - - - A S L P N D T Q R A M - E P C L D G W V Y N - - S T K
SEQ ID NO. 12  OAT1    C L R F T S P Q - - - - - W G L P F L N G T E A N G T G A T - E P C T D G W I Y D N S T F P
                       C   R .                                         .   .   .   E P C . D G W . Y

        150                 160                 170                 180                 190                 200
S T A V T Q W N L V C D R K W L A M L I Q P L F M F G V L L G S V T F G Y F S D R L G R R V V L W A T S S S
S T V V T E W N L V C E D N W K V P L T T S L F F V G V L L G S F V S G Q L S D R F G R K N V L F A T M A V
P S L K N E F N L V C D R K H L K D T T Q S V F M G G L L V G T L M F G P L C D R I G R K A T I L A Q L L L
S T I V T E W N L V C E D D W K A P L T I S L F F V G V L L G S F I S G Q L S D R F G R K N V L F V T M G M
S S I V T E F N L V C A N S W M L D L F Q S S V N V G F F I G S M S I G Y I A D R F G R K L C L L T T V L I
S S I V T E F N L V C A D S W K L D L F Q S C L N A G F L F G S L G V G Y F A D R F G R K L C L L G T V L V
S T I V T K W D L V C D Y Q S L K S V V Q F L L T G M L V G G I I H H G V S D R F G R R F I L R W C L L Q
S T I V A K W D L V C S S Q G L K P L S Q S I F M S G I L V G S F I W G L L S Y R F G R K P M L S W C C L Q
D S I V T E W D L V C N S N K L K E M A Q S I F M A G I L I G G L V L G D L S D R F G R R P I L T C S Y L L
S T I V T E W D L V C S H R A L R Q L A Q S L Y M V G V L L G A M V F G Y L A D R L G R R K V L I L N Y L Q
S T I V T E W N L V C         L     L . Q S . F .   G . L . G S . .   G   L S D R F G R K   . L     . . L .
```

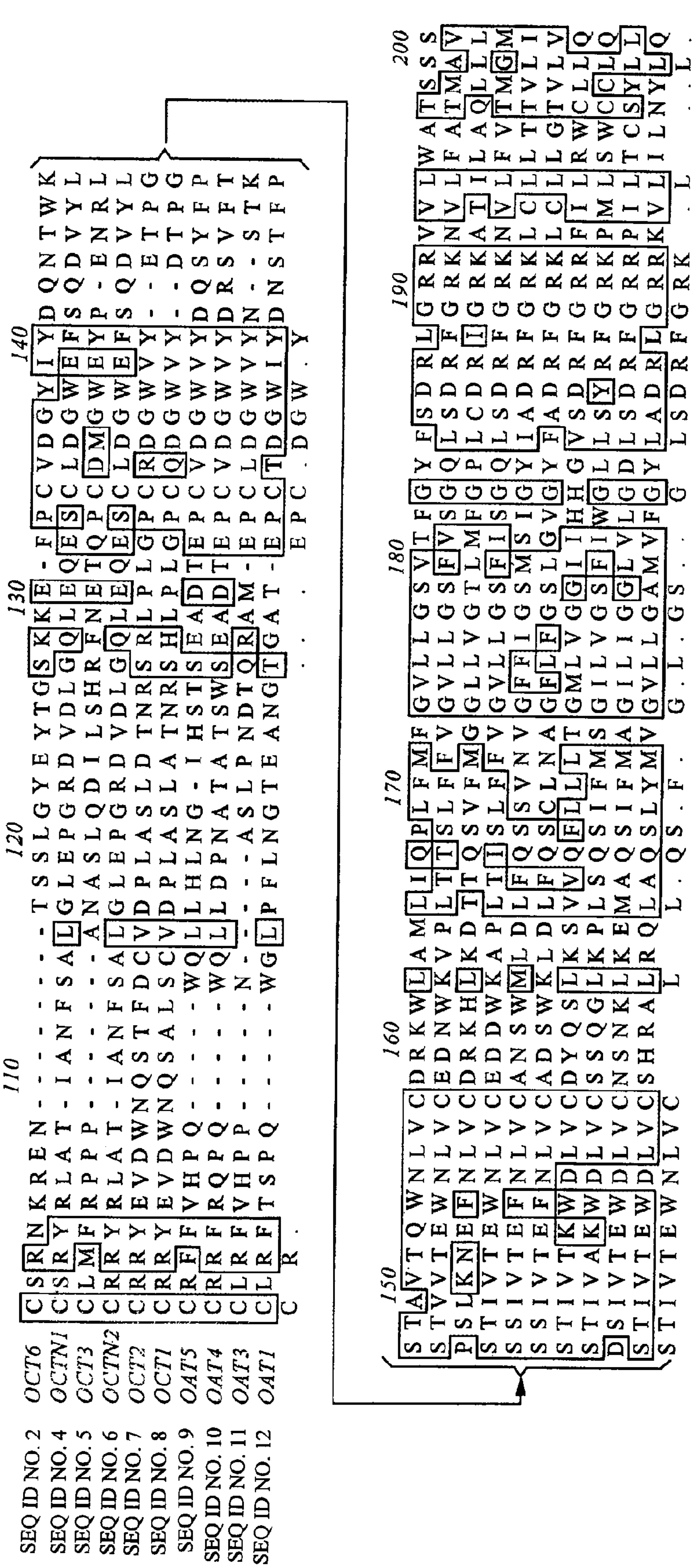

FIG. 2B

```
                            210       220       230       240       250
SEQ ID NO. 2   OCT6    MFLFGIAAAFAVDYYTFMAARFFLAMVASGYLVVGFVYVMEFIGMKSRTW
SEQ ID NO. 4   OCTN1   QTGFSFLQIFSISWEMFTVLFVIVGMGQISNYVVAFILGTEILGKSVRII
SEQ ID NO. 5   OCT3    FTLIGLATAFVPSFELYMALRFAVATAVAGLSFSNVTLLTEWVGPSWRTQ
SEQ ID NO. 6   OCTN2   QTGFSFLQIFSKNFEMFVVLFVLVGMGQISNYVAAFVLGTEILGKSVRII
SEQ ID NO. 7   OCT2    NAAAGVLMAISPTYTWMLIFRLIQGLVSKAGWLIGYILITEFVGRRYRRT
SEQ ID NO. 8   OCT1    NAVSGVLMAFSPNYMSMLLFRLLQGLVSKGNWMAGYTLITEFVGSGSRRT
SEQ ID NO. 9   OAT5    LAITDTCAAFAPTFPVYCVLRFLAGFSSMIIISNNSLPITEWIRPNSKAL
SEQ ID NO. 10  OAT4    LAVAGTSTIFAPTFVIYCGLRFVAAFGMAGIFLSSLTLMVEWTTTSRRAV
SEQ ID NO. 11  OAT3    LAASGSGAAFSPTFPIYMVFRFLCGFGISGITLSTVILNVEWVPTRMRAI
SEQ ID NO. 12  OAT1    TAVSGTCAAFAPNFPIYCAFRLLSGMALAGISLNCMTLNVEWMPIHTRAC
                        A..G  .AF.P.F ....R .G.  G  .  .L.TE .G   R.

                            260       270       280       290       300
                       ASVH-LHSFFAVGTLLVALTGYLXRTWXXYQMIXXSTVTVPFILCCWVLP
                       FSTLGVCTFFAVGYMLLPLFAYFIRDWRMLLLA-LTVPGVLCVPLWWFIP
                       AVVL-AQCNFSLGQMVLAGLAYGFRNWRLLQIT-GTAPGLLLFFYFWALP
                       FSTLGVCIFYAFGYMVLPLFAYFIRDWRMLLVA-LTMPGVLCVALWWFIP
                       VGIF-YQVAYTVGLLVLAGVAYALPHWRWLQFT-VALPNFFFLLYYWCIP
                       VAIM-YQMAFTVGLVALTGLAYALPHWRWLQLA-VSLPTFLFLLYYWCVP
                       VVIL-SSGALSIGQIILGGLAYVFRDWQTLHVV-ASVPFLGLLLLQRWLV
                       TMTV-VGCAFSAGQAALGGLAFALRDWRTLQLA-ASVPFFAISLISWWLP
                       MSTA-LGYCYTFGQFILPGLAYAIPQWRWLQLT-VSIPFFVFFLSSWWTP
                       VGTL-IGYVYSLGQFLLAGVAYAVPHWRHLQLL-VSAPFFAFFIYSWFIP
                        . .    ...G ..L G.AY .R WR LQ.. .S.P    .L  W .P
```

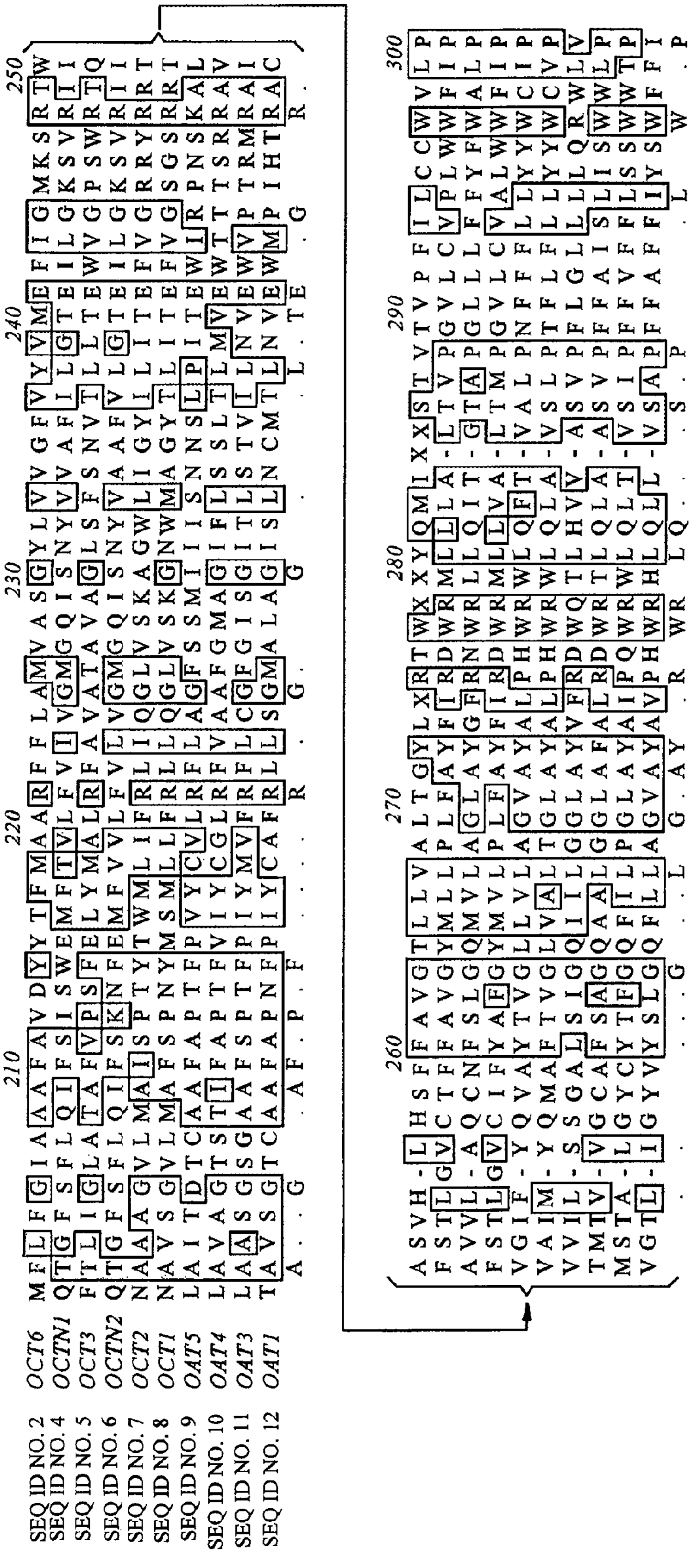

FIG. 2C

```
                                 410       420       430       440       450
SEQ ID NO. 2   OCT6    YLNLFLLGVVEIPAYTFVCIAXDKVGRRTVLAYSLFCSALACGVVMVIPQ
SEQ ID NO. 4   OCTN1   YLNCFLSALIEIPAYITAWLLLRTLPRRYIIAAVLFWGGGVLLFIQLVPV
SEQ ID NO. 5   OCT3    YLTQLIFGAVEVPARCSSIFMMQRFGRKWSQLGTLVLGGLMCIIIIFIPA
SEQ ID NO. 6   OCTN2   FVNCFLSAMVEVPAYVLAWLLLQYLPRRYSMATALFLGGSVLLFMQLVPP
SEQ ID NO. 7   OCT2    YLDFFYSALVEFPAAFMIILTIDRIGRRYPWAASNMVAGAACLASVFIPG
SEQ ID NO. 8   OCT1    YLDFFYSALVEIPGAFIALITIDRVGRIYPMAMSNLLAGAACLVMIFISP
SEQ ID NO. 9   OAT5    FLLQLLYGAVALIVRCLALLTLNHMGRRISQILFMFLVGLSILANTFVPK
SEQ ID NO. 10  OAT4    FLLQVLFGAVDFLGRATTALLLSFLGRRTIQAGSQAMAGLAILANMLVPQ
SEQ ID NO. 11  OAT3    YILQAIFGGVDVPAKFITILSLSYLGRHTTQAAALLLAGGAILALTFVPL
SEQ ID NO. 12  OAT1    YLIQIIFGAVDLPAKLVGFLVINSLGRRPAQMAALLLAGICILLNGVIPQ
                       YL   V. G VE.PA  ..L. .GRR  A .L L.G ..L .  .P

                                460       470       480       490       500
                       KHYILGVVTAMVGKFAIGAAFGLIYLYTAELYPTIVRSLAVGSGSMVCRL
                       DYYFLSIGLVMLGKFGITSAFSMLYVFTAELYPTLVRNMAVGVTSTASRV
                       DLPVVVTMLAVVGKMATAAAFTISYVYSAELFPTILRQTGMGLVGIFSRI
                       DLYYLATVLVMVGKFGVTAAFSMVYVYTAELYPTVIRNMGVGVSSTASRL
                       DLQWLKIIISCLGRMGITMAYEIVCLVNAELYPTFIRNLGVHICSSMCDI
                       DLHWLNIIIMCVGRMGITIAIQMICLVNAELYPTFVRNLGVMVCSSLCDI
                       EMQTLRVALACLGIGCSAATFSSVAVHFIELIPTVLRARASGIDLTASRI
                       DLQTLRVVFAVLGKGCFGISLTCLTIYKAELFPTPVRMTADGILHTVGRL
                       DLQTVRTVLAVFGKGCLSSSFSCLFLYTSELYPTVIRQTGMGVSNLWTRV
                       DQSIVRTSLAVLGKGCLAASFNCIFLYTGELYPTMIRQTGMGMGSTMARV
                       DL  L ..LA..GK ....AF.....Y.AELYPT..R. G.G. S. .R.
```

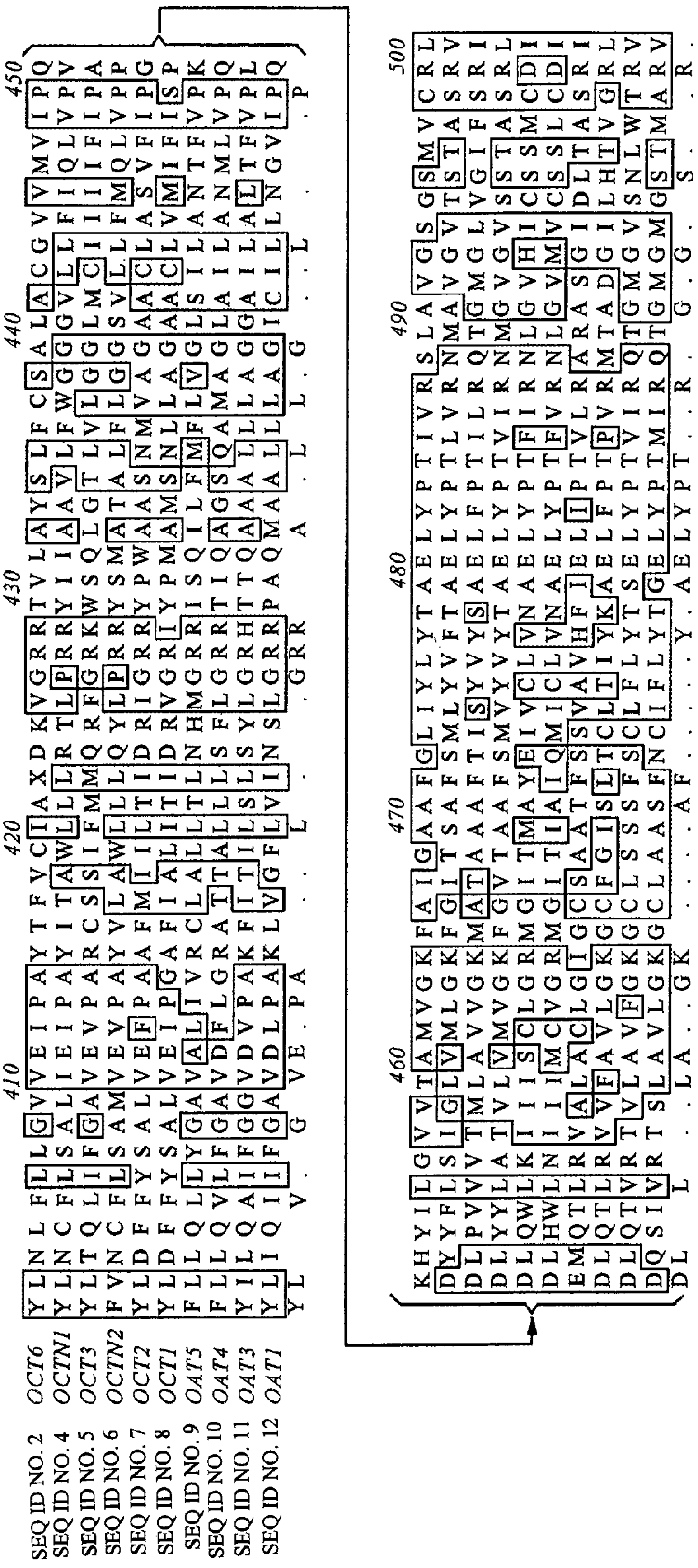

FIG. 2E

```
                             510       520       530       540
SEQ ID NO. 2   OCT6    A S I L A P F S V D L S S I W I F I P Q L F V G T M A L L S - G V L T L K L P E T L G K R
SEQ ID NO. 4   OCTN1   G S I I A P Y F V Y - L G A Y N R M L P Y I V M G S L T V L I G I L T L F F P E S L G M T
SEQ ID NO. 5   OCT3    G G I L T P L V I L L G E Y H A A L P M L I Y G S L P I V A - G L L C T L L P E T H G Q G
SEQ ID NO. 6   OCTN2   G S I L S P Y F V Y - L G A Y D R F L P Y I L M G S L T I L T A I L T L F L P E S F G T P
SEQ ID NO. 7   OCT2    G G I I T P F L V Y R L T N I W L E L P L M V F G V L G L V A G G L V L L L P E T K G K A
SEQ ID NO. 8   OCT1    G G I I T P F I V F R L R E V W Q A L P L I L F A V L G L L A A G V T L L L P E T K G V A
SEQ ID NO. 9   OAT5    G A A L - P L L M T L T V F F T T L P W I I Y G I F P I I G - G L I V F L L P E T K N L P
SEQ ID NO. 10  OAT4    G A M M G P L I L M S R Q A L P L L P P L L Y G V I S I A S S L V V L F F L P E T Q G L P
SEQ ID NO. 11  OAT3    G S M V S P L V K I T G E V Q P F I P N I I Y G I T A L L G - G S A A L F L P E T L N Q P
SEQ ID NO. 12  OAT1    G S I V S P L V S M T A E L Y P S M P L F I Y G A V P V A A - S A V T V L L P E T L G Q P
                       G . I . . P . .             . P . I   G .   . .   G . . . L   L P E T   G

 550       560       570       580       590       600
 L A T T W E E A A K L E S E N E S K S - - - S K L L L T T N N S G L E K T E A I T P R D S G L G E
 L P E T L E Q M Q K V K W F R S G K K - - - T R D S M E T E E N P K V L I T A F
 L K D T L Q D L E L G P H P R S P K S V P S E K E T E A K G R T S S P G V A F V S S T Y F
 L P D T I D Q M L R V K G M K H R K T P S H T R M L K D G Q E R P T I L K S T A F
 L P E T I E E A E N M Q R P R K N K E - - - K M I Y L Q V Q K L D I P L N
 L P E T M K D A E N L G R K A K P K E - - - N T I Y L K V Q T S E P S G T
 L P D T I K D V E N Q K - - - - K N L - - - K E K A
 L P D T I Q D L E S Q K S T A A Q G N - - - R Q E A V T V E S T S L
 L P E T I E D L E N W S L R A K K P K - - - Q E P E V E K A S Q R I P L Q P H G P G L G S S
 L P D T V Q D L E - - S R K G K Q T R - - - Q Q Q - - E H Q K Y M V P L Q A S A Q E K N G L
 L P . T . . D . E                 K                   .     .
```

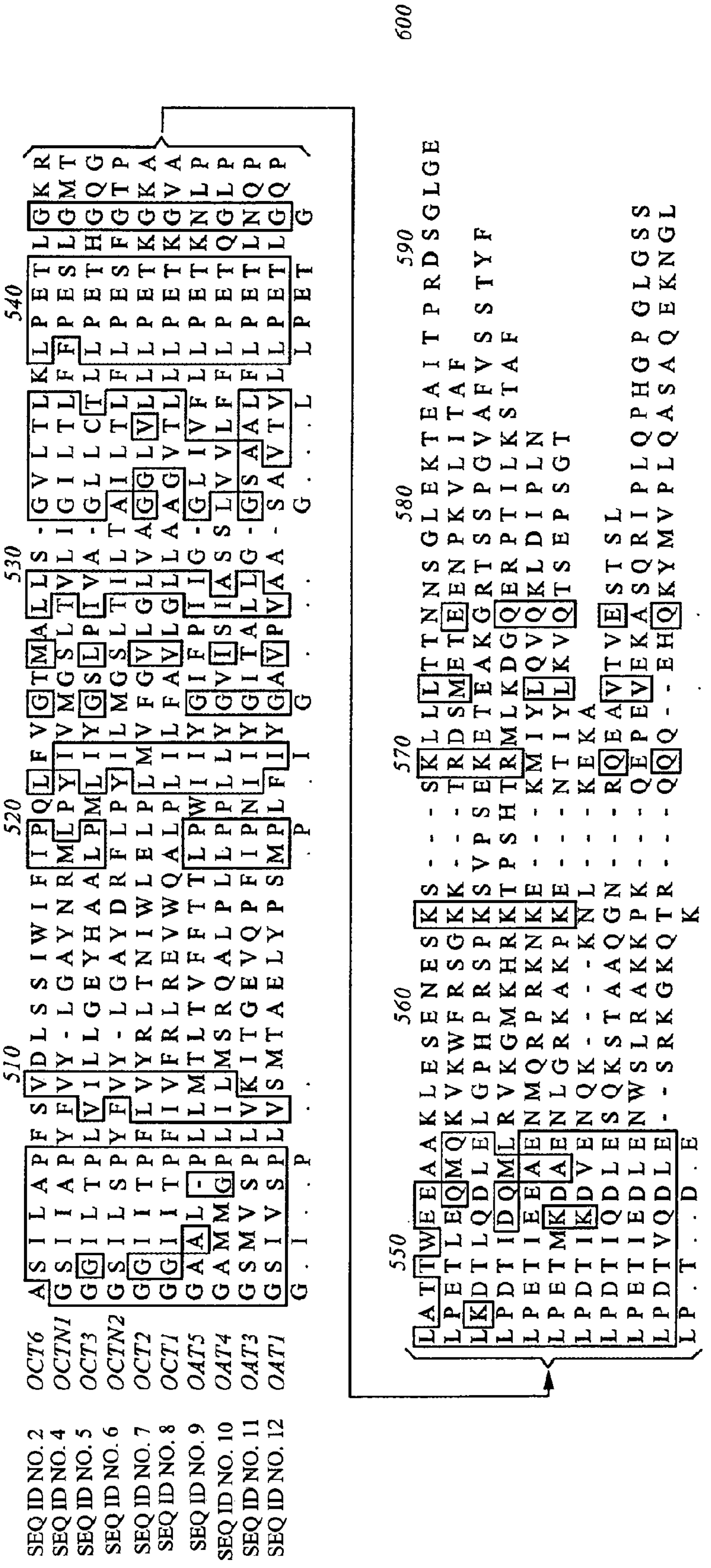

FIG. 2F

ORGANIC CATION TRANSPORTER PREFERENTIALLY EXPRESSED IN HEMATOPOIETIC CELLS AND LEUKEMIAS AND USES THEREOF

CROSS REFERENCE TO RELATED APPLICATIONS

This application is a divisional application of and claims the benefit of application Ser. No. 10/849,551, filed May 20, 2004 now abandoned, which claims the benefit of U.S. Provisional Application No. 60/471,709, filed May 20, 2003.

FIELD OF THE INVENTION

The invention relates to a gene encoding an organic cation transporter, OCT6, and its use as a target for the treatment of hematological malignancies, and in particular, leukemia. The invention further relates to screening methods for identifying agonists and antagonists/binding partners of OCT6 transport activity.

BACKGROUND OF THE INVENTION

The lipid bilayer of the cellular membrane insulates the intracellular milieu from exposure to hydrophilic compounds. Unlike lipophilic compounds that can diffuse through cellular membranes, water-soluble compounds usually require specific transport mechanisms to gain access to the intracellular space. The regulation of the traffic of polar compounds in both directions across the cellular membrane is a complex process involving several large families of transport proteins.

Most often in cancer research, drug transport is thought of as a mechanism of cellular drug resistance, as drug efflux pumps such as the products of the MDR1 and MRP genes have been shown to be mechanisms of resistance to lipid-soluble anticancer drugs. However, drug transport is a two-way street, and mechanisms also exist for pumping drugs into cells. For polar, water-soluble anticancer agents, drug uptake, and not drug efflux, is the critical determinant of cellular drug accumulation.

Most cancer chemotherapy employs drugs that are lipid-soluble that can easily penetrate the cell membrane of cancer cells. One advantage of using lipid-soluble drugs is that they easily gain intracellular access to different types of cancer cells, so many cancer cells appear to be initially sensitive to these drugs. The disadvantage is that cancer cells learn to increase the activity of drug efflux pumps in the cell membrane to pump lipid-soluble drugs out of the cell, resulting in drug resistance.

In contrast, potential water-soluble anticancer drugs may not survive the preclinical screening process since there is a great deal of variability in the expression of drug transport genes in different types of cancer cells. Variability in transport gene expression may result in variability in accumulation of polar, water-soluble drugs. One approach to more effectively utilize water-soluble anticancer drugs is to identify which of the dozens of transport genes are actually expressed in tumors.

The importance of carrier-mediated anticancer drug uptake is exemplified in reduced folate carrier (RFC) mediated uptake of methotrexate (MTX). Methotrexate (MTX), a reduced folate analogue, is scavenged and retained in cells by mechanisms designed to secure folates from the environment. The major mechanism of MTX uptake at pharmacologic concentrations is the reduced folate carrier (RFC), an OAT transporter with a Km for MTX between approximately 0.8-26 μM. Decreased RFC activity has been observed in several in vitro models of transport-mediated MTX resistance (Biochem. Pharmacol. 11: 1233-1234, 1960). Once rodent and human genes encoding proteins with RFC activity were isolated, the molecular explanations for decreased RFC activity emerged. RFC1 transfection into the transport-deficient $MTX^R$ ZR75 cell line resulted in a 20-fold increase in 6-hour MTX uptake and a concomitant 250-fold increase in sensitivity to MTX relative to control cell clones, showing that the RFC1 gene reconstitutes RFC activity and has a significant impact on MTX cytotoxicity (Moscow, et al., Cancer Res. 55: 3790-3794, 1995).

In different cell lines, MTX transport deficiency has been ascribed either to mutations in the RFC gene or in decreased expression of the RFC gene product. Several studies have demonstrated that RFC1 gene expression is an important determinant of sensitivity to MTX. In in vitro studies, we have found that RFC1 RNA levels correlate with MTX sensitivity in a panel of non-selected cell lines, including breast cancer cell lines (Moscow et al., Int J Cancer. 72: 184-190, 1997).

A plethora of genes with the ability to transport MTX out of the cell have been reported, including MRP1, MRP2, MRP3, MRP4, the organic anion transporters hOAT2 and hOAT3, and the mitoxantrone-resistance protein (BCRP/MXR). However, despite the multitude of MTX export genes, clinical studies have shown a relationship between the expression of RFC1, the mechanism of MTX uptake, and prognosis in Acute Lymphoid Leukemia (ALL) and osteosarcoma. As a result, RFC1 expression and MTX uptake are now implicated as determinants of clinical sensitivity in several types of tumors. Thus, the role of RFC1 in mediating sensitivity of its cytotoxic drug substrates has become a prototype that illustrates the potential role of transporters, like OAT and OCT genes, in determination of anticancer drug selectivity and toxicity.

However, there is a need to identify additional channels, or transporters, that are found in specific cancers, to enable the targeting of different cancers with anticancer agents that are substrates for those transporters.

SUMMARY OF THE INVENTION

The present invention is directed towards a membrane protein that functions to transport hydrophilic substances across cellular membranes. The protein, OCT6, is a new member of the organic cation transporter (OCT) family (SLC22 gene family). Tissue distribution of this protein is distinct from other OCT protein family members; being detected in leukemia, leukemia blast cells and CD34+ cells.

In one aspect, the present invention provides a novel target for hematological malignancies such as leukemia, an OCT6 transporter.

In another aspect of the present invention there is a method for screening potential substrates that selectively bind the OCT6 transporter. The method involves contacting a cell which overexpresses an OCT6 transporter gene with a test compound and determining whether the test compound is a substrate for the OCT6 transporter.

In another aspect, there is a method for screening potential anti-cancer agents in a cell overexpressing an OCT6 transporter gene. The method comprises determining viability of a cell which expresses OCT6 transporter gene incubated in the presence and absence of a test compound and identifying the test compound as a potential anti-cancer agent if there is cellular influx of the test compound and cell death.

In another aspect of the invention, a test kit is provided for screening candidate drugs for hematologic malignancies comprising a mammalian cell line or cells which overexpress OCT6, a control substrate and a detectable substance.

In still another aspect of the invention, there are immunogenic compositions for treating hematological malignancies. In a preferred embodiment, immunogenic compositions for treating leukemia comprise a substrate that binds selectively to a leukemia cell expressing the OCT6 transporter gene. In another preferred embodiment of the invention, the substrate comprises an antibody that selectively binds to the OCT6 transporter protein. Preferably, the OCT6 transporter protein allows cellular uptake of the substrate which then causes cell death. In one embodiment the substrate is cytotoxic and in another preferred embodiment the substrate is coupled with a cytotoxic agent.

In still another aspect, the present invention provides a method for impairing a leukemia cell comprising contacting the cell with a cytotoxic OCT6 transporter protein. In one embodiment the substrate is a cytotoxin and in another embodiment the substrate is coupled to a cytotoxic agent.

In yet another aspect, the present invention provides a method for treating hematological malignancies comprising administering to a subject in need thereof an immunogenic composition comprising a substrate that binds selectively to a cell expressing the OCT6 transporter gene. In a preferred embodiment the OCT6 transporter protein allows cellular uptake of the substrate which then causes cell death. In another preferred embodiment the substrate is cytotoxic. In another preferred embodiment, the substrate is coupled with a cytotoxic agent.

BRIEF DESCRIPTION OF THE DRAWINGS

FIG. 1. B. is a dendrogram showing phylogenic relationship between OCT6 (SEQ ID NO:2) and other OCT and OAT proteins, including, OCTN1 (SEQ ID NO:4), OCT3 (SEQ ID NO:5), OCTN2 (SEQ ID NO:6), OCT2 (SEQ ID NO:7), OCT1 (SEQ ID NO:8), OAT5 (SEQ ID NO:9), OAT4 (SEQ ID NO:10), OAT3 (SEQ ID NO:11), and OAT1 (SEQ ID NO:12).

FIG. 2A-F. is the CLUSTLAW alignment of OCT6 and other OCT and OAT proteins. The bottom row represents areas of consensus.

DETAILED DESCRIPTION OF THE INVENTION

Figure 1A:
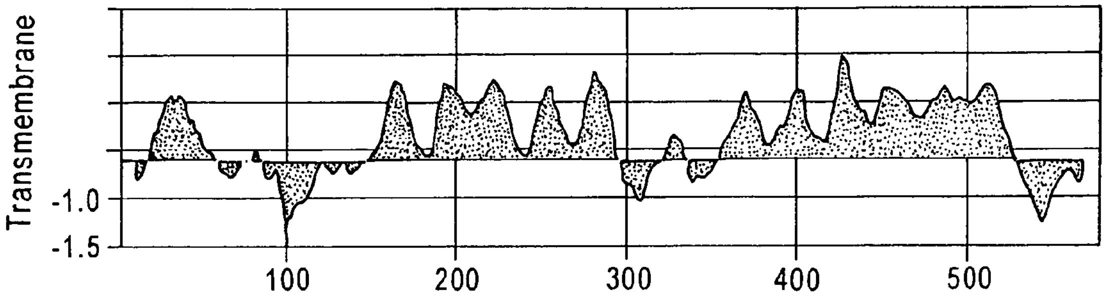
FIG. 1. A. shows the predicted hydropathy profile of OCT6.

The present invention is based on the discovery and isolation of a new member of the SLC22 gene family (the OCT family of proteins) that is unusual for its distinct pattern of tissue distribution. Rather than the typical high levels of expression in liver, kidney or placenta, high levels of RNA for this transporter were found in some leukemia cell lines, in CD34+ cells, and in circulating leukemia blast cells.

All patents, patent applications and literature cited in this description are incorporated herein by reference in their entirety. In the case of inconsistencies, the present disclosure, including definitions, will prevail.

OCT Family

Two families of proteins involved in maintaining homeostasis of charged organic compounds are the organic anion transporters (OATs) which carry the SLC21 designation and the organic cation transporters (OCTs), which carry the SLC22 designation (See Table 1). OATs and OCTs each have characteristic patterns of tissue expression, with predominant expression in a tissue involved in the transport of xeriobiotics, i.e., liver, kidney or placenta.

TABLE 1

| | Organic anion and cation transported genes | | |
|---|---|---|---|
| Gene Family | Gene Name | Locus Link | Alternative Names |
| SLC21 | SLC21A1 | 6577 | |
| | SLC21A2 | 6578 | PGT |
| | SLC21A3 | 6579 | OATP, OATP1, OATP1b, OATP-A |
| | SLC21A4 | 28237 | OAT-K1, OAT-K2 |
| | SLC21A5 | 28236 | OATP2, OATP-2 |
| | SLC21A6 | 10599 | LST-1, OATP-C |
| | SLC21A7 | 28235 | OATP3, OATP-3 |
| | SLC21A8 | 28234 | LST2, OATP8, SLC21A8, OATP-8 |
| | SLC21A9 | 11309 | OATP-B |
| | SLC21A10 | 28233 | OATP4 |
| | SLC21A11 | 28232 | OATP-D |
| | SLC21A12 | 28231 | LOC51737, OATP-E, POAT |
| | SLC21A13 | 28230 | OATP5, OATP-5 |
| | SLC21A14 | 53919 | OATP-F |
| SLC22 | SLC22A1 | 6580 | OCT1 |
| | SLC22A2 | 6582 | OCT2 |
| | SLC22A3 | 6581 | OCT3 |
| | SLC22A4 | 6583 | OCTN1 |
| | SLC22A5 | 6584 | OCTN2, CDSP, SCD |
| | SLC22A6 | 9356 | NKT, OAT1, OAT-1 |
| | SLC22A7 | 10864 | NLT, OAT2, OAT-2 |
| | SLC22A8 | 9376 | OAT3, OAT-3 |
| | SLC22A9 | | OAT4, OAT-4 |

The OAT and OCT carriers result in increased cellular accumulation of their respective substrates, despite the fact that they are carriers that mediate facilitative diffusion. For carriers, the degree of intracellular accumulation may not exceed the extracellular concentration. However, the presence of the carrier allows uptake in comparison to no uptake in the absence of the carrier, and drugs that bind an intracellular target or which are chemically modified in the cells, e.g., by phosphorylation or polyglutamylation, may be eliminated from the substrate pool and not available for transport back across the cellular membrane.

The first five members of the SLC22 family of transporters, OCT1, OCT2, OCT3, OCTN1, and OCTN2, have been characterized as organic cation transporters. The uptake of many cations, such as tetraethylammonium (TEA), N-1-methylnicotineamide (NMN), choline, procainamide, amantadine and morphine are mediated by these polyspecific transporters. In general, these transporters are potential-dependent, but independent of sodium and proton gradients. These genes are all characterized by the presence of 11 or 12 transmembrane domains, as predicted by hydrophobicity analysis, and all have a large hydrophilic loop between transmembrane domain (TMD) 1 and TMD2.

OCT substrates are shown below in Table 2. Tetraethyl ammonium (TEA) is the classic substrate for OCT transporters. In addition, OCT1, OCT2 and OCT3 transport 1-methyl-4-phenylpyridinium (MPP). Compared to OCT2, OCT1 has a higher affinity for some cations (for example mepiperphenidol and procainamide), a similar affinity for others (for example, decynium 22 and quinidine), and a lower affinity for corticosterone (See Koepsell et al., Ann. Rev. Physiol. 60: 243-266, 1998.). OCT3 is an electrogenic transporter for TEA and guanidine. Other physiologic substrates for OCT transporters include dopamine, histamine, epinephrine and norepinephrine, acetylcholine and 5-hydroxytryptamine (Burckhardt, et al., Am J Physiol Renal Physiol. 278: F853-66., 2000.), suggesting an important role for these transporters in the central nervous system, in addition to their role in hepatic and renal clearance. Interestingly, despite its cationic nature, recent studies have identified cimetidine as a selective inhibitor, but not a substrate for several organic cation transporters, including rOCT1, rOCT2, rOCT3, hOCTN1, and hOCTN2.

TABLE 2

OCT Substrates

| Common Name | Gene Name | Cell Type | Substrate | KT (uM) |
|---|---|---|---|---|
| OCT1 | SLC22A1 | HeLa | TEA | 229 |
| OCT1 | SLC22A1 | Xenopus | MPP | 14.6 |
| OCT2 | SLC22A2 | Xenopus | Norepinephrine | 1900 |
| OCT2 | SLC22A2 | Xenopus | Histamine | 1300 |
| OCT2 | SLC22A2 | Xenopus | Dopamine | 390 |
| OCT2 | SLC22A2 | Xenopus | Serotonin | 80 |
| OCT2 | SLC22A2 | HEK293 | MPP | 16 |
| OCT2 | SLC22A2 | HEK293 | Dopamine | 330 |
| OCT2 | SLC22A2 | Xenopus | Amantadine | 27 |
| OCT2 | SLC22A2 | Xenopus | Memantine | 34 |
| OCT3 | SLC22A3 | HeLa | TEA | 2500 |
| OCT3 | SLC22A3 | HRPE | MPP | 47 |
| OCTN1 | SLC22A4 | Fibroblasts | L-Carnitine | 6.6 |
| OCTN2 | SLC22A5 | HEK293 | L-Carnitine | 4.34 |
| OCTN2 | SLC22A5 | HEK293 | L-Carnitine | 4.3 |
| OCTN2 | SLC22A5 | HEK293 | D-Carnitine | 10.9 |
| OCTN2 | SLC22A5 | HEK293 | Acetyl-L-carnitine | 8.5 |
| OCTN2 | SLC22A5 | Xenopus | L-Carnitine | 4.8 |
| OCTN2 | SLC22A5 | Xenopus | D-Carnitine | 98 |
| OCTN2 | SLC22A5 | JAR | L-Carnitine | 3.5 |

OCT1 and OCT2 are predominantly expressed in the kidney and liver. These transporters are located on the basolateral surface of renal tubules and, therefore, play a role in the removal of organic cations from the blood. OCT3 is most abundantly expressed in placenta. In addition, other tissue-specific roles have been implicated for these transporters. As noted above, OCTs may play a role in transport of endogenous neuroleptic substrates, and OCT3 has been implicated in the disposition of cationic neurotoxins and neurotransmitters in the brain (Wu, et al., J Biol Chem. 273: 32776-86, 1998). Dhillon et al. (Clin Pharmacol Ther. 65: 205, 19996) used RT-PCR followed by functional transport studies (TEA) to identify OCT1 expression in a human mammary epithelial cell line (MCF12A). Further, the OCT1 gene has been shown to be up regulated in lactating mammary epithelial cells.

The OCTN1 gene, cloned from a cDNA, shows sequence similarity to organic cation transporter genes, which is highly expressed in kidney as well as trachea, bone marrow and fetal liver. Recombinant OCTN1 expressed in mammalian cells exhibited saturable uptake of TEA that was pH sensitive. Several others suggest that OCTN1 is a renal proton/organic cation antiporter functioning at the epithelial apical membrane. The uptake of pyrilamine, quinidine, verapamil and L-carnitine were increased by expression of OCTN1 in *Xenopus* oocytes.

Another OCT protein family member, OCTN2, cloned from a human placental trophoblast cell line, is expressed widely in human tissues including kidney, placenta and heart. OCTN2 is more closely related to OCTN1 than to OCT1, OCT2 and OCT3 (Biochem Biophys Res Commun. 246: 589-95, 1998). Transfection of OCTN2 has demonstrated its role in the transport of TEA and carnitine. OCTN2-mediated transport of TEA is sodium independent, whereas transport of carnitine is sodium-dependent. The role of sodium in OCTN2-mediated carnitine transport not only involves the electrogenic gradient, but the presence of sodium also alters the affinity of OCTN2 for carnitine. Germline mutations of OCTN2 result in primary carnitine deficiency, a syndrome of progressive cardiomyopathy and skeletal myopathy. The symptoms associated with this syndrome are thought to result not only from generalized carnitine deficiency from decreased renal carnitine reabsorbtion, but also from inability of cardiac and skeletal myocytes, which ordinarily express OCTN2, to accumulate carnitine. This syndrome demonstrates that tissue-specific OCT-mediated transport is essential for accumulation of required cations in specific tissues.

The present invention identifies a new transport protein in the OCT family, OCT6, preferentially expressed in leukemia cell lines, leukemia blast cells and CD34+ cells. The cell surface localization and the transporter function of the OCT6 gene product suggest its usefulness as a target in the diagnosis and treatment of hematologic malignancies.

As used herein, the term "antibody" refers to an immunoglobulin molecule with a specific amino acid sequence evoked in by an antigen, and characterized by reacting specifically with the antigen in some demonstrable way.

As used herein, the term "carrier" refers to a diluent, adjuvant, excipient, or vehicle with which the compositions of the present invention are administered.

As used herein, "compound" refers to any agent, chemical, substance, or substrate, whether organic or inorganic, or any protein including antibodies, peptides, polypeptides, peptoids, and the like.

As used herein, the term cytotoxin" or cytoxic agent includes any specific substance, which may or may not be antibody, that inhibits or prevents the functions of cells, causes destruction of cells, or both.

As used herein, the term "derivative" refers to something produced by modification of something pre-existing; for example, a substance or chemical compound that may be produced from another substance or compound of similar structure in one or more steps.

As used herein, the term "fragment" refers to a part of a larger entity, said larger entity comprising by non-limiting example, an antibody, compound or substance.

As used herein, the term "leukemia blast" or "leukemic blast" refers to lymphoblasts, the abnormal immature white blood cells associated with leukemia.

As used herein, the term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced.

As used herein, the term "pharmaceutically acceptable carrier" refers to a carrier that may be administered to a subject, together with one or more liver protecting agents and one or more mushroom powder or extract of the present invention, and which does not destroy the pharmacological activity thereof and is nontoxic when administered in doses sufficient to deliver a therapeutic amount of the compound.

As used herein, the term "substrate" refers to a substance, compound, agent, antibody or derivatives and/or fragment thereof, acted upon by the OCT6 transporter protein (e.g., a substance that is taken across the cellular membrane by action of the OCT6 transporter protein).

Figure 1B:
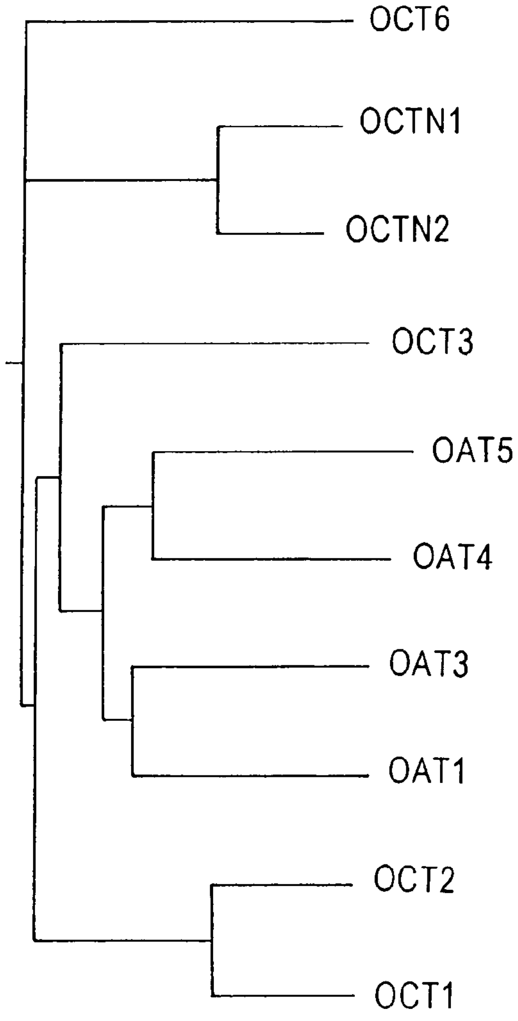
Figure 2D:
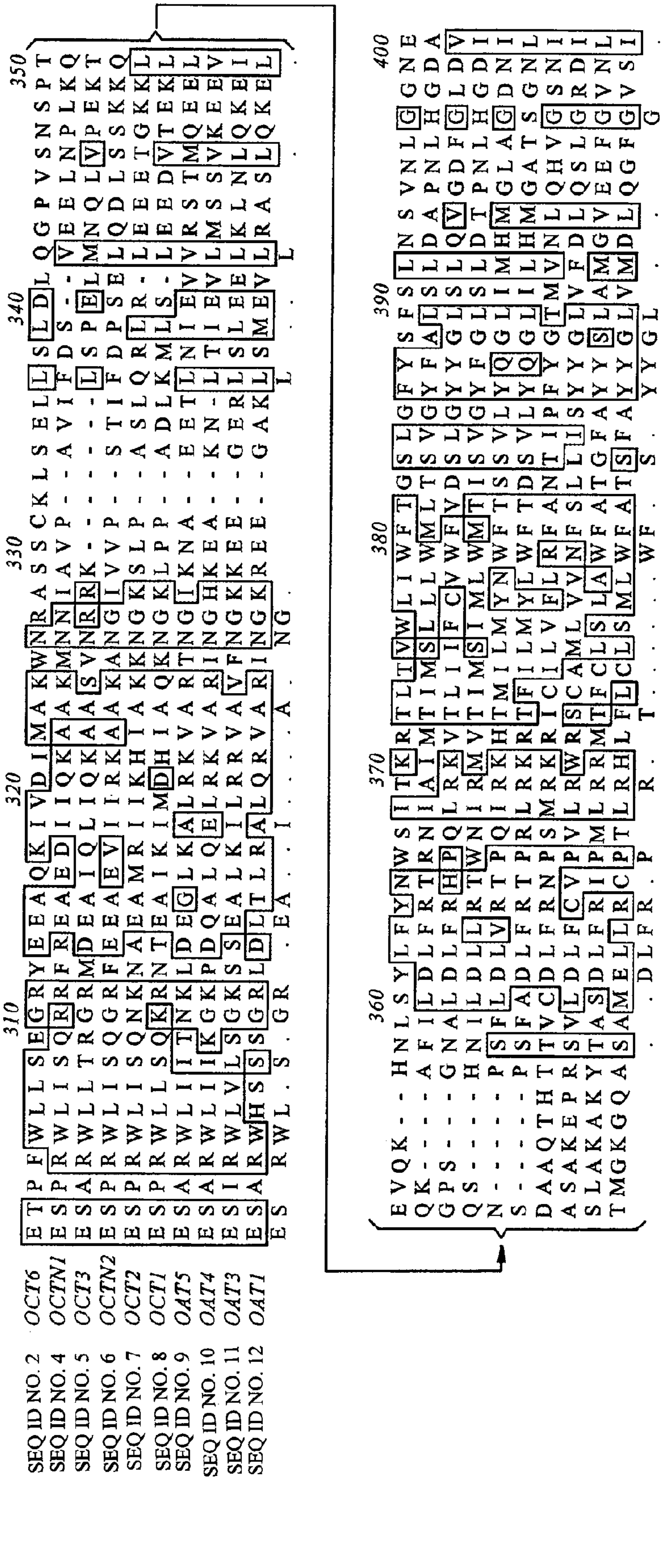

OCT6 (SEQ ID NO:1) was first identified as a potential OCT gene by assembling and sequencing ESTs as described in Example 1 (amino acid sequence of OCT6 is SEQ ID NO:2). The gene sequence proved to be identical to the recently submitted cDNA OKB1 (GenBank AF268892) submitted by M. Okabe and T. Abe, incorporated herein in its entirety. It is also contained within the submitted BAC clone CTA-331P3 (SEQ ID NO: 3) (GenBank AC002464) located at chromosome 6q21, incorporated herein in its entirety. The gene has a predicted protein structure typical of transport proteins with two groups of six transmembrane domains separated by a hydrophilic region (FIG. 1A). CLUSTALW alignment produced a dendrogram showing the phylogenic relationship between OCT6 and other OAT and OCT proteins (FIG. 1B). This dendrogram suggests that the distinction between OAT and OCT genes, based on functional studies, obscures the common origin of both families of transporters. The actual CLUSTALW alignment of these genes is shown in FIG. 2 and demonstrates multiple regions of conservation among all of these genes.

Next, according to the methods described in Example 3, quantitative RT PCR analysis of the expression of OCT6 was performed, along with the expression of other OCT genes, in 50 cell lines. The results are shown in Table 3. The two highest expressing cell lines for OCT6 in this panel were two leukemia cell lines, HL60, a human promyelocytic leukemia cell line, and MOLT4, a human acute lymphoblastic leukemia (T-cell) cell line. There was only a low level of expression detected in most of the other cell lines.

TABLE 3

OCT expression in 50 cell lines of the NCI Drug Screen

| No. | Cell Line | source | OCT1 | OCT2 | OCT3 | OCTN 2 | OCT6 |
|---|---|---|---|---|---|---|---|
| 1 | CCRF-CEM | Leukemia | 0.7 | 0.7 | 0.2 | 0.1 | 5.7 |
| 2 | HL-60 | Leukemia | 0.5 | 1.3 | 0.0 | 0.4 | 716 |
| 3 | K-562 | Leukemia | 1.4 | 1.2 | 0.2 | 1.4 | 5.2 |
| 4 | MOLT-4 | Leukemia | 0.1 | 1.1 | 0.5 | 0.6 | 46.8 |
| 5 | RPMI-8226 | Leukemia | 2.8 | 2.0 | 0.1 | 3.7 | 6.02 |
| 6 | SR | Leukemia | 1.9 | 1.1 | 0.0 | 0.3 | 2.6 |
| 7 | A549/ATCC | Lung cancer | 1.7 | 1.2 | 161 | 4.3 | 1.2 |
| 8 | HOP-62 | Lung cancer | 0.8 | 4.8 | 0.6 | 2.4 | 4.1 |
| 9 | NCI-H226 | Lung cancer | 4.8 | 0.5 | 0.1 | 21.1 | 4.8 |
| 10 | NCI-H23 | Lung cancer | 0.5 | 0.7 | 0.0 | 0.3 | 5.2 |
| 11 | NCI-H460 | Lung cancer | 0.7 | 1.0 | 0.0 | 1.7 | 1.8 |
| 12 | COLO205 | Colon Ca. | 4.9 | 5.3 | 30.9 | 2.2 | 3.6 |
| 13 | HCC-2998 | Colon Ca. | 1.5 | 1.0 | 0.0 | 2.6 | 5.4 |
| 14 | HCT-116 | Colon Ca. | 1.7 | 2.1 | 0.1 | 2.8 | 9.7 |
| 15 | HCT-15 | Colon Ca. | 0.9 | 1.7 | 0.1 | 3.5 | 4.2 |
| 16 | HT-29 | Colon Ca. | 1.9 | 1.2 | 18.1 | 1.5 | 1.5 |
| 17 | KM-12 | Colon Ca. | 0.6 | 1.0 | 12.2 | 0.7 | 2.1 |
| 18 | SW-620 | Colon Ca. | 1.0 | 2.6 | 40.4 | 1.9 | 3.7 |
| 19 | SF-268 | CNS Tumor | 0.4 | 0.8 | 0.0 | 0.9 | 2 |
| 20 | SF-295 | CNS Tumor | 0.5 | 1.2 | 0.2 | 1.1 | 2.5 |
| 21 | SF-539 | CNS Tumor | 0.5 | 0.6 | 2.3 | 0.2 | 5.3 |
| 22 | SNB-75 | CNS Tumor | 0.8 | 1.8 | 0.0 | 0.6 | 2.3 |
| 23 | U251 | CNS Tumor | 0.8 | 0.9 | 0.0 | 0.6 | 7.4 |
| 24 | LOCIMVI | Melanoma | 2.9 | 2.1 | 0.1 | 0.4 | 3.6 |
| 25 | MALME-3M | Melanoma | 1.5 | 1.5 | 0.0 | 2.3 | 3 |
| 26 | M14 | Melanoma | 1.9 | 1.4 | 0.0 | 1.9 | 4.7 |
| 27 | SK-MEL-2 | Melanoma | 2.1 | 1.9 | 0.0 | 2.2 | 3.9 |
| 28 | SK-MEL-5 | Melanoma | 2.6 | 1.5 | 0.0 | 1.9 | 2.7 |
| 29 | UACC-257 | Melanoma | 3.2 | 3.6 | 0.0 | 1.1 | 5.4 |
| 30 | IGROV1 | Ovarian Ca. | 4.9 | 5015 | 17.9 | 1.8 | 2.5 |
| 31 | OVCAR-3 | Ovarian Ca. | 1.4 | 0.1 | 0.0 | 2.2 | 14 |
| 32 | OVCAR-4 | Ovarian Ca. | 2.6 | 1.4 | 0.0 | 8.9 | 3.4 |
| 33 | OVCAR-5 | Ovarian Ca. | 3.5 | 2.7 | 105 | 10.0 | 4.8 |
| 34 | OVCAR-8 | Ovarian Ca. | 1.1 | 1.0 | 0.0 | 0.8 | 1.6 |
| 35 | SK-OV-3 | Ovarian Ca. | 3.9 | 1995 | 9.2 | 8.5 | 9.8 |
| 36 | A498 | Renal Ca. | 2.2 | 13.4 | 180 | 4.7 | 1.3 |
| 37 | ACHN | Renal Ca. | 1.1 | 1.1 | 0.7 | 1.2 | 1.1 |
| 38 | CAKI_1 | Renal Ca. | 3.5 | 2.5 | 4.8 | 1.8 | 2.8 |

TABLE 3-continued

OCT expression in 50 cell lines of the NCI Drug Screen

| No. | Cell Line | source | OCT1 | OCT2 | OCT3 | OCTN 2 | OCT6 |
|---|---|---|---|---|---|---|---|
| 39 | RXF-393 | Renal Ca. | 1.7 | 1.2 | 3.0 | 0.6 | 1.2 |
| 40 | TK-10 | Renal Ca. | 3.6 | 5.0 | 16.8 | 2.5 | 8 |
| 41 | UO-31 | Renal Ca. | 4.4 | 1.6 | 31.2 | 1.2 | 2.3 |
| 42 | PC-3 | Prostate Ca. | 2.1 | 0.8 | 9.6 | 3.3 | 4.7 |
| 43 | DU-145 | Prostate Ca. | 1.1 | 1.1 | 3.4 | 1.6 | 3 |
| 44 | MCF-7 | Breast Ca. | 0.8 | 1.8 | 0.0 | 10.4 | 3.5 |
| 45 | NCI/ADR-RES | Breast Ca. | 1.4 | 1.3 | 1.1 | 2.0 | 2.1 |
| 46 | MDA-MB-231 | Breast Ca. | 1.2 | 0.4 | 3.9 | 4.8 | 1.8 |
| 47 | HS578T | Breast Ca. | 1.0 | 1.5 | 0.0 | 1.2 | 8.3 |
| 48 | MDA-MB-435 | Breast Ca. | 1.9 | 0.6 | 0.1 | 0.7 | 2.7 |
| 49 | BT-549 | Breast Ca. | 1.2 | 0.8 | 0.1 | 0.3 | 2.6 |
| 50 | T-47D | Breast Ca. | 0.7 | 1.1 | 0.1 | 4.2 | 8.7 |

Figure 3A:
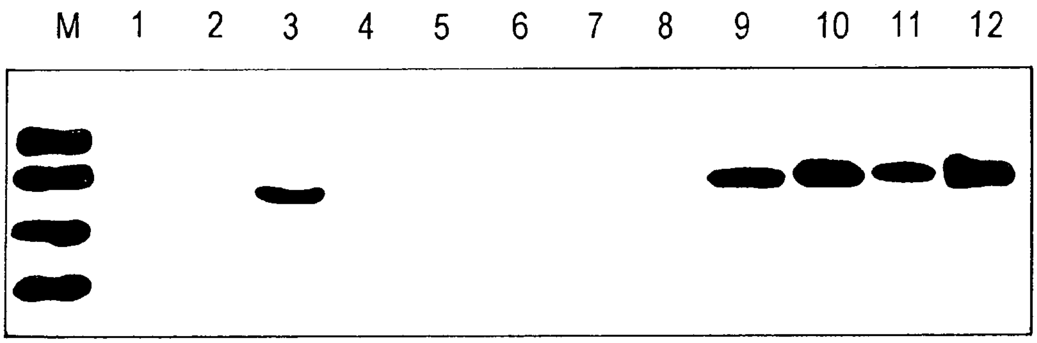
FIG. 3. shows the normal tissue distribution of OCT6 RNA determined by RT-PCR using a cDNA panel. Only 1000× (highest) cDNA concentration is shown. Panel A. 1, salivary gland; 2, thyroid; 3, adrenal; 4, pancreas; 5, ovary; 6, uterus; 7, prostate; 8, skins; 9, peripheral blood leukocytes; 10, bone marrow; 11, fetal brain; 12, fetal liver. Panel B. 1, brain; 2, heart; 3, kidney; 4, spleen; 5, liver; 6, colon; 7, lung; 8, small intestine; 9, muscle; 10, stomach, 11, testis; 12, placenta.
Figure 3B:
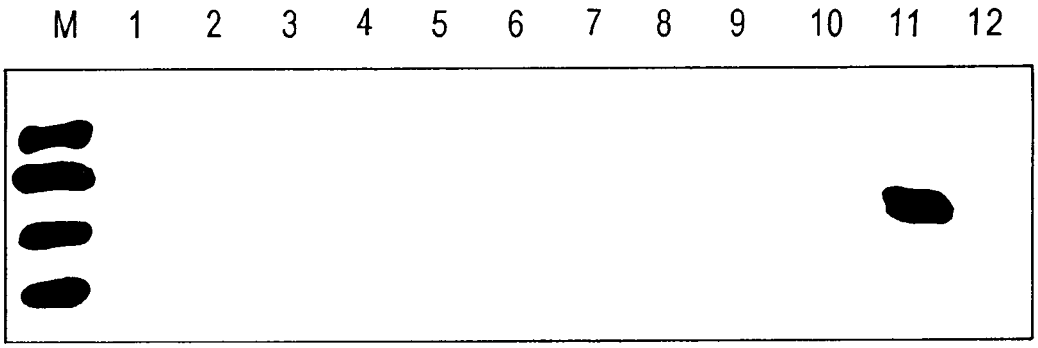

OCT6 is unique among the known members of OCT and OAT genes because of its pattern of tissue distribution. The pattern of expression of the OCT6 gene in the 50 cell lines suggested that its expression might be restricted to hematopoietic tissues. The restricted pattern of expression observed for OCT6 also suggests that therapies using OCT6-specific substrates are unlikely to have widespread toxicity to normal tissues. Therefore, we examined OCT6 expression in a cDNA panel representing a wide cross-section of normal tissues according to the methods of Example 4 (FIG. 3). This study revealed that OCT6 RNA levels are highest in testis and fetal liver, with lower but detectable levels in peripheral blood leukocytes and bone marrow. Since fetal hematopoiesis occurs in the liver, it is possible that the fetal liver sample may have included both hepatocytes and hematopoietic cells. OCT6 RNA levels were also barely detectable in pancreatic and adrenal tissue. Unlike other OCT genes, expression was not detectable in liver, kidney or placenta.

Figure 4:
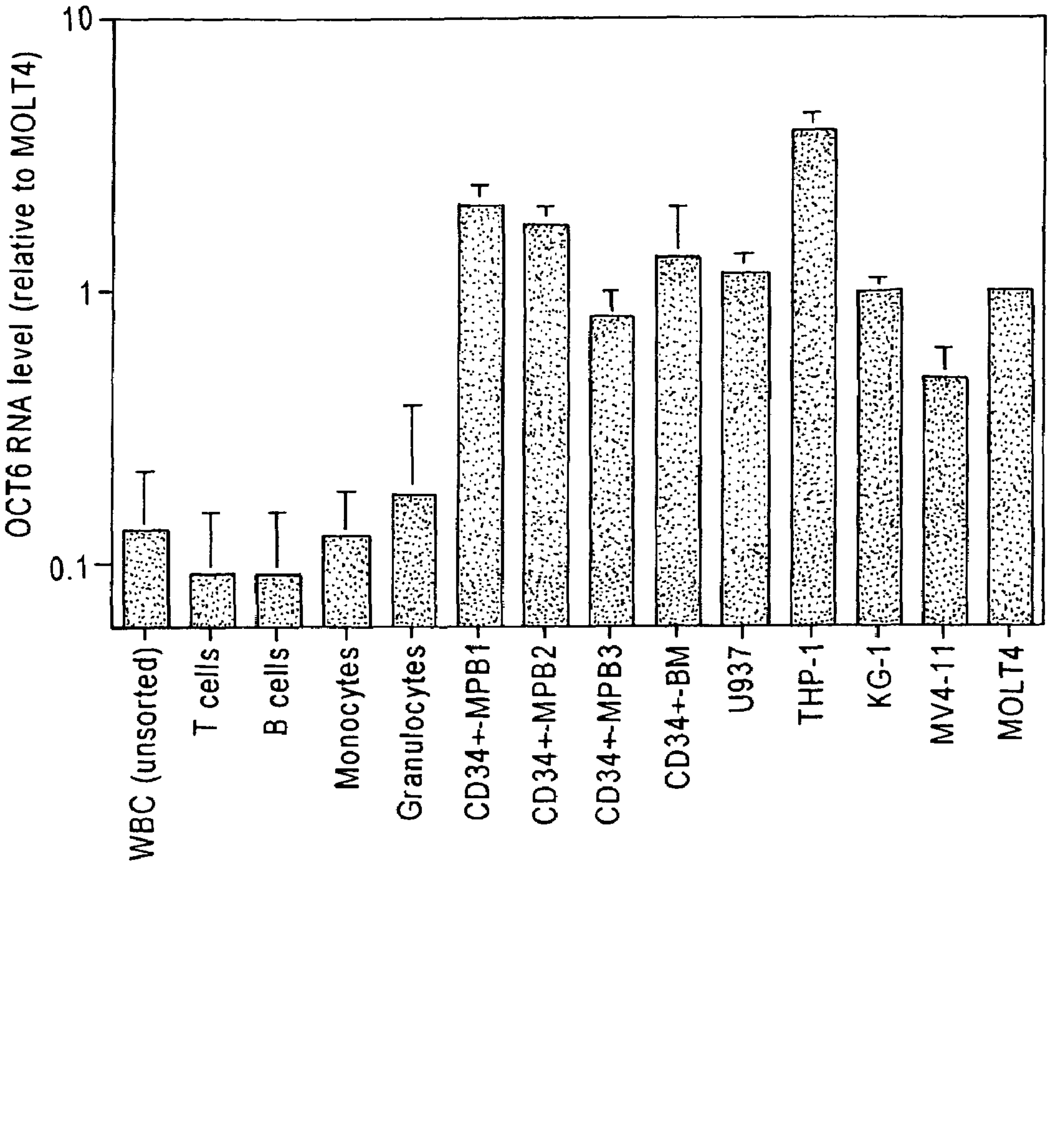
FIG. 4. shows quantitative RT-PCR for the transporter gene OCT6 performed with RNA extracted from peripheral blood leukocytes, CD34+ cells and additional hematopoietic cell lines. Fresh discarded buffy coats that were twice sorted by FACS using CD14 (monocytes), CD15 (granulocytes), CD3 (T-cells) and CD20 (B-cells). Purities of 99% or better were obtained. For peripheral WBC and sorted subsets, the average±SD represent pooled results from samples from 2 individuals performed in triplicate or quadruplicate. For CD34-selected mobilized peripheral blood (MPB), the results from each of 3 individuals are shown. For CD34-selected bone marrow (CD34+-BM), the results are from one individual. OCT6 levels were normalized to the expression of actin RNA, as a control for equivalence of mRNA template. The units, in log scale, are arbitrary and based on a standard curve of OCT6 RT-PCR in serially diluted HL60 RNA. Unity is defined as the level of OCT6 RNA found in MOLT4 cells.

To determine whether OCT6 RNA expression in hematopoietic cells was lineage-specific, leukocytes were sorted from discarded buffy coat specimens by flow cytometry, and purified subpopulations were examined for OCT6 RNA expression according to the methods described in Example 5. OCT6 expression was also examined in a population of CD34+ cells. As can be seen in FIG. 4, the expression of OCT6 was highly enriched in CD34+ cells in comparison to the other cell populations. Also, significant levels of OCT6 expression (relative to MOLT4) were found in other hematopoietic cell lines: U937, a human histiocytic lymphoma cell line; THP-1, a human acute monocytic leukemia cell line; KG-1, a human erythroleukemia cell line; and MV-4-11, a human biphenotypic (B-cell and myelomonocytic) leukemia cell line.

Figure 5:
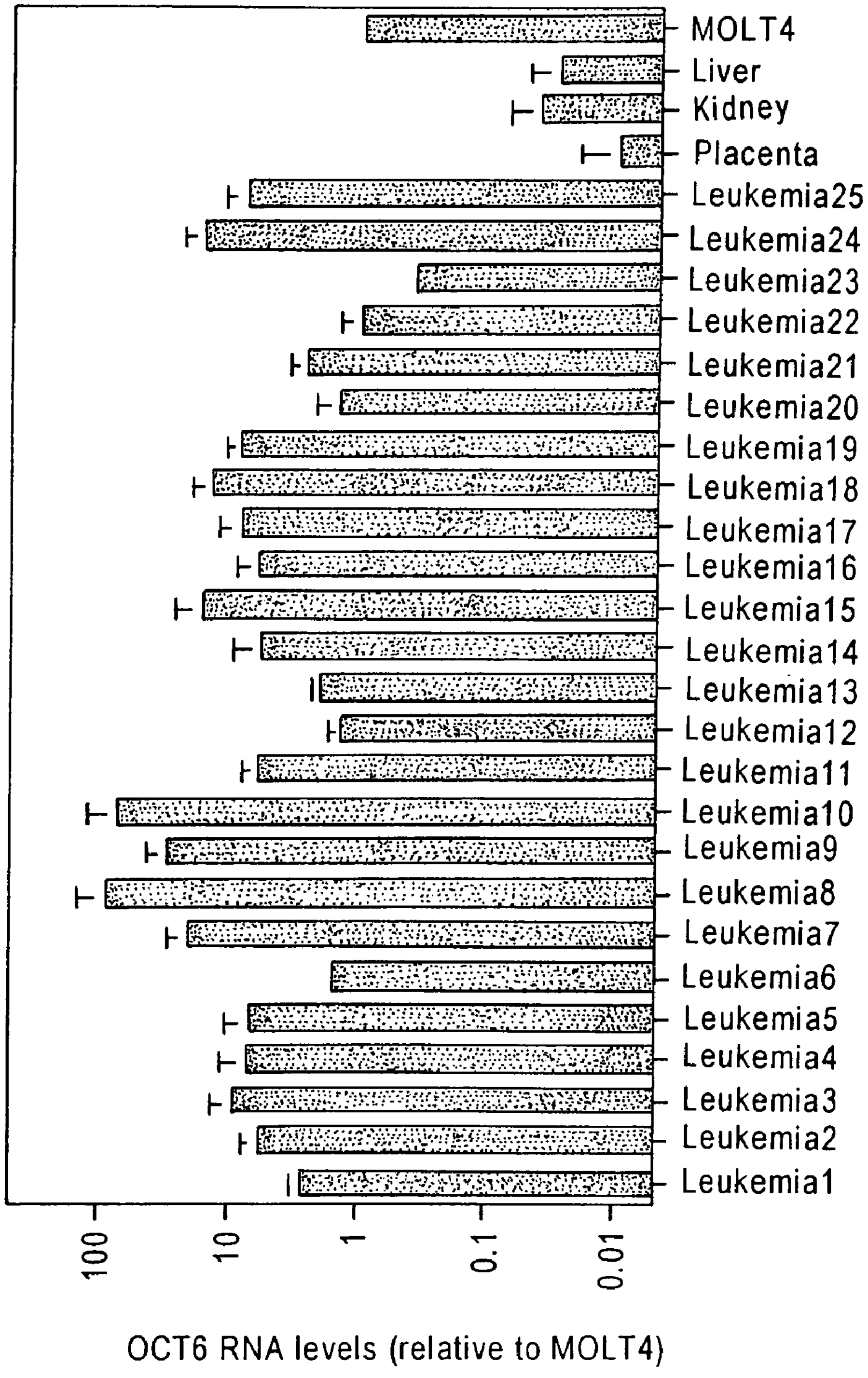
FIG. 5. shows quantitative RT-PCR for the gene OCT6 using RNA extracted from leukemic blasts obtained from patients at the time of initial diagnosis. OCT6 levels were normalized to the expression of actin RNA, as a control for equivalence of mRNA template. The OCT6 RNA levels in placenta, liver, kidney and MOLT-4 cell line were determined concurrently and shown for comparison. The units, in log scale, are arbitrary and based on a standard curve of OCT6 RT-PCR in serially diluted HL60 RNA. Unity is defined as the level of OCT6 RNA found in MOLT4 cells.

The high levels of OCT6 RNA in some leukemia cell lines and CD34+ cells also raised the question as to whether this gene was highly expressed in actual leukemias. To address this issue, the RNA levels of OCT6 in 25 samples of peripheral leukemic cells were measured according to the methods set out in Example 6. The FAB classification of these samples are shown in Table 4. These results are shown in FIG. 5, and demonstrate that the majority of specimens contained RNA levels for OCT6 that exceeded the level found in MOLT4 cell line, the second highest expressing cell line among those examined, and exceed by orders of magnitude the levels found in placenta, kidney and liver.

TABLE 4

Phenotypes of leukemia specimens

| Sample Number | Description |
|---|---|
| 1 | CML, blast crisis |
| 2 | CML, blast crisis |
| 3 | CML, stable phase |
| 4 | CML, probably stable phase |
| 5 | CML, accelerated phase |
| 6 | ALL |
| 7 | ALL |
| 8 | AML |
| 9 | ALL |
| 10 | ALL |
| 11 | ALL |
| 12 | AML |
| 13 | AML |
| 14 | AML |
| 15 | AML |
| 16 | ALL, biphenotypic |
| 17 | ALL, biphenotypic |
| 18 | AML |
| 19 | AML, M2 |
| 20 | AML, M2 |
| 21 | AML, M4 |
| 22 | AML, M4 |
| 23 | AML, M1 |
| 24 | AML |
| 25 | AML, M4 |

Due to the OCT6 protein's location on the cellular membrane and its function as an intracellular transporter, the OCT6 transporter protein has been identified as a therapeutic target. Basic principles of cellular pharmacology suggest that increase in intracellular accumulation will lead to increased intracellular effect. For anticancer drugs, this principle has been studied extensively in the context of lipophilic drugs, which require no specific mechanism for cellular uptake, and export pumps such as the product of the multidrug resistance gene, MDR1, whose overexpression of MDR1 leads to increased cellular resistance by decreasing intracellular concentrations of drug (Moscow, J. A., Schneider, E. S., Ivy, S. P., and Cowan, K. H. Multidrug resistance. In: H. M. Pinedo, D. L. Longo, and B. A. Chabner (eds.), Cancer chemotherapy and biological response modifiers. Annual 17. New York: Elsevier, 1997). The same principle applies to charged, hydrophilic drugs of the present invention, except that the determinants of sensitivity depend on uptake as opposed to efflux. As such, cells overexpressing an OCT6 transporter are likely to be highly sensitive to cytotoxic OCT6 substrates.

Drug Screening

Accordingly, the present invention provides methods for screening potential substrates of, and potential therapeutic agents against hematological malignancies like leukemia that overexpress, the OCT6 transporter. In particular, potential therapeutic agents are screened for the ability to be a substrate recognized by an OCT6 transporter protein. Preferably, potential substrates are screened for the ability to confer cytotoxic effects on a cell overexpressing OCT6 transporter protein. More preferably, agents are screened for the ability to preferentially cause cellular uptake into, and cell death of, cells overexpressing the OCT6 transporter. Most preferably, the agents are screened for the ability to cause cell death of cancer cells such as leukemia overexpressing the OCT6 transporter as compared to normal cells.

A method for screening potential substrates of the OCT6 transporter protein comprises providing a cell or cell line which expresses OCT6 and a test compound, incubating the test compound and cell line and analyzing the cell or cell line to determine if there was a cellular influx of the test compound. Analysis of the cell line to determine whether cellular uptake of the test compound occurred can be accomplished by any means known in the art. For example, a test compound can be tagged with a detectable label prior to contact with a cell and then observed under microscopy or by other means for its location. Non-limiting examples of labels include green fluorescent protein, alkaline phosphatase, horseradish peroxidase, rease, f3-galactosidase, CAT, luciferase, an immunogenic tag peptide sequence, an extrinsically activatable enzyme, an extrinsically activatable toxin, an extrinsically activatable fluor, an extrinsically activatable quenching agent, a radioactive element or an antibody.

A method for screening candidate anti-cancer agents comprises determining the viability of a mammalian cell which expresses OCT6 incubated in the presence and absence of a test compound and identifying the test compound as a potential anti-leukemia agent if there is a cellular uptake of the test compound and cell death. Analysis of cell viability can be accomplished by any means known in the art.

It is well known in the art that viability of a cell can be determined by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. The most common dye used in the art for determining viability is trypan blue. Viability of cells can also be determined by detecting DNA synthesis. Cells can be cultured in cell medium with labeled nucleotides (e.g., $^3$H thymidine). The uptake or incorporation of the labeled nucleotides indicates DNA synthesis and cell viability. In addition, colonies formed by cells cultured in medium indicate cell growth and is another means to test viability of the cells.

Identification and/or observation of cells undergoing apoptosis can be another method of determining cell viability. Apoptosis is a specific mode of cell death recognized by a characteristic pattern of morphological, biochemical, and molecular changes. Cells going through apoptosis appear shrunken, and rounded; they also can be observed to become detached from culture dish. Thermophological changes involve a characteristic pattern of condensation of chromatin and cytoplasm which can be readily identified by microscopy. When stained with a DNA-binding dye, such as H33258, apoptotic cells display classic condensed and punctate nuclei instead of homogeneous and round nuclei.

The hallmark of apoptosis is the endonucleolysis, a molecular change in which nuclear DNA is initially degraded at the linker sections of nucleosomes to give rise to fragments equivalent to single and multiple nucleosomes. When these DNA fragments are subjected to gel electrophoresis, they reveal a series of DNA bands which are positioned approximately equally distant from each other on the gel. The size difference between the two bands next to each other is about the length of one nucleosome (i.e., 20 base pairs). This characteristic display of the DNA bands is called a DNA ladder and it indicates apoptosis of the cell. Apoptotic cells can be identified by flow cytometric methods based on measurement of cellular DNA content, increased sensitivity of DNA to denaturation, or altered light scattering properties. These methods are well known in the art and are within the contemplation of the invention.

Abnormal DNA breaks are also characteristic of apoptosis and can be detected by any means known in the art. In one embodiment, DNA breaks are labeled with biotinylated dUTP (b-dUTP). Cells are fixed and incubated in the presence of biotinylated dUTP with either exogenous terminal transferase (terminal DNA transferase assay; TdT assay) or DNA polymerase (nick translation assay; NT assay). The biotinylated dUTP is incorporated into the chromosome at the places where abnormal DNA breaks are repaired, and are detected with fluorescein conjugated to avidin under fluorescence microscopy.

Kits

The present invention provides kits that can be used in the above screening methods. In one embodiment, a kit comprises a substantially isolated polypeptide comprising an OCT6 epitope which is specifically immunoreactive with only test compound(s) that are substrates of the OCT6 transporter protein. Binding of a test compound to the OCT6 epitope is indicative that the test compound is a OCT6 substrate. In another embodiment, a kit comprises a cell line that overexpresses an OCT6 transporter protein. Binding and/or cellular uptake of a test compound via the OCT6 protein is indicative that the test compound is a OCT6 substrate. Preferably, the kits of the present invention further comprise a control compound or antibody which does not react with the OCT6 transporter protein. In another specific embodiment, the kits of the present invention contain a means for detecting the binding of a test compound to an OCT6 epitope and/or cellular uptake of a test compound. For example, the test compound may be conjugated to a detectable substrate such as a fluorescent compound, an enzymatic substrate, a radioactive compound or a luminescent compound, or a second antibody which recognizes the first antibody may be conjugated to a detectable substrate.

The detectable substance may be coupled or conjugated either directly to the test compound (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Further non-limiting examples of detectable substances include various enzymes, prosthetic groups, fluorescent materials, luminescent materials, bioluminescent materials, radioactive materials, positron emitting metals using various positron emission tomographies, nonradioactive paramagnetic metal ions, immunogenic tag peptide sequences, extrinsically activatable toxins, extrinsically activatable quenching agents, or antibodies. Non-limiting examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

Immunogenic Compositions

The present invention also provides immunogenic compositions for the treatment of hematological malignancies. Non-limiting exemplary hematological malignancies include, but are not limited to, Hodgkin's disease, leukemia such as, acute lymphoid (lymphocytic or lymphoblastic) leukemia (ALL), acute myeloid (myelogenous or myeloblastic) leukemia (AML), acute lymphoid leukemia, biphenotypic (ALL, biphentoypic), acute undifferentiated leukemia (AUL), chronic myeloid (myelogenous or granulocytic) leukemia (CML), erythroleukemia, granuloxytic leukemia, lymphoma, monocytic leukemia, myleoma, myelomonocytic leukemia, myelodysplastic syndromes, non-Hodgkin lymphoma, pro-granulocytic leukemia.

According to the invention immunogenic compositions for the treatment of hematological malignancies comprise a substrate recognized by an OCT6 transporter protein. Preferably, the substrate is a compound that binds selectively or specifically to a OCT6 transporter protein. In a preferred embodiment, the compound binds selectively to the OCT6 transporter protein encoded by a nucleotide sequence of SEQ ID NO:1. The compound may be a cytotoxin or coupled or conjugated with a cytoxic agent. Preferably the cytoxin or cytotoxic agent is a chemotherapeutic agent.

The present invention also provides pharmaceutical compositions. Such compositions comprise a therapeutically effective amount of a compound, and a pharmaceutically acceptable carrier.

Cell surface proteins like the OCT6 transporter can be utilized in antibody-based targeting strategies. In still another aspect of the invention, antibodies can be developed by known methods in the art against the external epitope of OCT6 transporter protein. In a preferred embodiment, antibodies are substrates of the OCT6 protein. The antibodies may be polyclonal antibodies or monoclonal antibodies.

Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties).

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate, such as, for example, a linker known in the art, using techniques known in the art. (See, for example, U.S. Pat. No. 4,741,900 for metal ions which can be conjugated to antibodies for use as diagnostics according to the present invention.) Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}Bi$. Non-limiting examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response such as inducing cell death for the treatment and prevention of hematological malignancies like leukemia. The therapeutic agent or drug moiety is not to be construed as limited to classical chemical therapeutic agents. For example, the drug moiety may be a protein or polypeptide possessing a desired biological activity for inducing cell death. Such proteins may include, for example, a toxin such as abrin, ricin A, pseudomonas exotoxin, or diphtheria toxin; a protein such as tumor necrosis factor, a-interferon, .beta.-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Therapeutic Treatment

The present invention is further directed to methods for preventing and treating hematological malignancies such as leukemia. According to the invention, hematological malignancies comprise without limitation, Hodgkin's disease, leukemia such as, acute lymphoid (lymphocytic or lymphoblastic) leukemia (ALL), acute myeloid (myelogenous or myeloblastic) leukemia (AML), acute lymphoid leukemia, biphenotypic (ALL, biphentoypic), acute undifferentiated leukemia (AUL), chronic myeloid (myelogenous or granulocytic) leukemia (CML), erythroleukemia, granuloxytic leukemia, lymphoma, monocytic leukemia, myleoma, myelomonocytic leukemia, myelodysplastic syndromes, non-Hodgkin lymphoma, progranulocytic leukemia.

Methods of treatment of the present invention comprise administering to a subject in need thereof an immunogenic composition of the present invention. The compositions may be administered with a pharmaceutically acceptable carrier.

Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate. etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of hematological malignancies can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Various other delivery systems are known and can be used to administer a composition of the invention, e.g., encapsulation in liposomes, microparticles, microcapsules, recombinant cells capable of expressing the compound, receptor-mediated endocytosis (See, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (See Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

EXAMPLES

The following examples are presented for the illustrative purposes and it is to be understood that the present invention is not limited to those precise embodiments, and that various changes and modifications can be effected therein by one skilled in the art without departing from the scope and spirit of the invention as defined by the appended claims.

Example 1

OCT6 Nucleotide Sequence Identification and Analysis

OCT6 was first identified as a potential OCT gene by assembling and sequencing ESTs. BLAST searches of human ESTs in GenBank data base identified AI040384 (654 bp), AA033971 (714 bp) and H70190 (474 bp) sequences from three fetal liver IMAGE clones, 1656502, 429904 and 212935 respectively. IMAGE clone 1656502 (3', insert 1337 bp) ended the predicted 3' stop codon, whereas IMAGE clone 429904 (5', insert 996 bp) and IMAGE clone 212935 (5', insert 966 bp) aligned with the 5'-coding region. All clones were obtained from the IMAGE Consortium through the American Type Culture Collection (Manassas, Va.). Each clone was sequenced in both directions. The sequences were determined using ABI Prism™ 377 DNA sequencer (Perkin-Elmer). Our assemblage proved to be identical to the recently submitted cDNA OKB1 (AF268892) submitted by M. Okabe and T. Abe. We have dubbed this gene OCT6 as OCTN1 and OCTN2 may be considered as OCT4 and OCT5 respectively.

The OCT6 gene (SEQ ID NO:1) is also contained within BAC clone CTA-331P3 (SEQ ID NO:3) (GenBank AC002464) located at chromosome 6q21. It is divided into 6 exons that span 42 kb on the human genome, from nucleotide 79,570 to nucleotide 120490 on CTA-331P3.

The gene has a predicted protein structure typical of transport proteins with 2 groups of 6 transmembrane domains separated by a hydrophilic region (FIG. 1A). The large hydrophilic region between TMD1 and TMD2 is typical of OCT and OAT genes and is presumed to be located on the outside surface of the cell membrane. The OCT6 protein contains potential sites for N-glycosylation and phosphorylation, which will be described below in Methods. Of interest, the protein sequence also contains a 22 amino acid leucine zipper motif, starting at amino acid 146, suggesting that there may be a physical interaction between OCT6 and ion channels or other membrane-associated proteins.

CLUSTALW alignment produced a dendrogram showing the phylogenic relationship between OCT6 and other OAT and OCT proteins (FIG. 1B). This dendrogram suggests that the distinction between OAT and OCT genes, based on functional studies, obscures the common origin of both families of transporters. The actual CLUSTALW alignment of these genes is shown in FIG. 2 and demonstrates multiple regions of conservation among all of these genes.

The hydropathy profile analysis, multiple sequence alignments of amino acid sequences using CLUSTALW and the phylogenetic tree were all produced with MacVector software.

Example 2

Molecular Cloning of OCT6

BLAST searches of human ESTs in GenBank data base identified AI040384 (654 bp), AA033971 (714 bp) and H70190 (474 bp) sequences from three fetal liver IMAGE clones, 1656502, 429904 and 212935 respectively. IMAGE clone 1656502 (3', insert 1337 bp) ended the predicted 3' stop codon, whereas IMAGE clone 429904 (5', insert 996 bp) and IMAGE clone 212935 (5', insert 966 bp) aligned with the 5'-coding region. All clones were obtained from the IMAGE Consortium through the American Type Culture Collection (Manassas, Va.). Each clone was sequenced in both directions. The sequences were determined using ABI Prism™ 377 DNA sequencer (Perkin-Elmer).

Example 3

Quantitative RT-PCR of OCT6 RNA Levels in Cancer Cell Lines

Total RNA isolated from 50 cell lines used in the NCI drug screen program was provided by the Developmental Therapeutics Program, NCI. Quantitative RT-PCR for detecting OAT-X transporter gene expression was performed by using a Roche LightCycler, which uses real time fluorescence detection for quantitative measurement of PCR products. A gene-specific primer pair was designed with Oligo 4.0 software and purchased from Integrated DNA Technologies, Inc. (Coralville, Iowa) (F: 5'-GGCACATTTATTCACCAAGACCAG-3') (SEQ ID NO: 13) and (F: 5'-TGTGGACCTCAGCAG-CATTTGGAT-3') (SEQ ID NO:14). The specificity of the PCR reaction was confirmed by directly determining the DNA sequence of the PCR product. First, cDNA was synthesized from total RNA using SuperScript First-Strand Synthesis System (GIBCO/BRL) in a 20 μl volume following the instructions supplied by the manufacturer. The cDNA treated with RNAse H for 20 minutes at 37° C. and stored at −20° C. Then, 2 ul of cDNA reaction was amplified in a standard PCR reaction condition, using 0.3 μM primer concentration, with the addition of SYBR Green I Dye. After 30 seconds denature at 95° C., the amplification reaction proceeded through 45-50 cycles of 95° C. denature for 0 second, 62-65° C. annealing for 10 seconds and a 72° C. extension for 40 seconds, with slopes of 20° C./s, 20° C./s and 2° C./s, respectively.

Fluorescence was acquired during each cycle after heating to a temperature just below the product melting temperature. Quantification was performed using the LightCycler analysis software. The log-linear portion of the standard amplification curve was identified, and the 'crossing point', a threshold of relative fluorescence, was determined as the best fit through the log-linear region above the background fluorescence (noise) band. The quantification of PCR product then was derived by plotting fluorescence data in the log linear region of each sample to determine a calculated number of cycles needed to reach the fluorescence crossing point. The calculated number of cycles required to reach the crossing point is proportional to the amount of target RNA in the sample. The relative amount of product was described in arbitrary units by interpolation of the data using a standard curve of a series of dilutions of a standard cell line RNA. The quantitative measurement of each gene in each cell line was normalized to the relative amount of actin RNA in each cell line, as a control for equivalent cDNA loading in each sample. The results represent the average of 3 independent determinations performed in duplicate.

A melting curve analysis was performed with positive control RNA prior analysis of the cell lines to enhance sensitivity and the specificity of the data. Amplified products usually melt quickly at a temperature characteristic for the products. The fluorescence signal was acquired at a temperature just below the Tm of the specific PCR product and above the Tm of the primer dimers. All specific PCR products displayed a single, sharply melting curve with a narrow peak. In addition, PCR products were confirmed for specificity and correct size by visualization of the LightCycler products on a 1% agarose gel.

Example 4

Tissue Distribution

First strand cDNAs derived from 24 adult and fetal tissues (RAPID-SCAN gene expression panel, OriGene Technologies, Rockville, Md.). The PCR primers used in this study were the same as used in the quantitative RT-PCR studies. The PCR reaction samples were denatured at 94° C. for 30 seconds, annealed and extended at 64° C. for 30 sec for 35 cycles. The PCR products were then visualized on 1% agarose gels.

Example 5

Cell Sorting

All human specimens were obtained in accordance with institutional IRB guidelines. Leukocytes from fresh discarded buffy coats were isolated after RBC lysis with ammonium chloride and labeled with lineage specific antibodies (CD14, monocytes; CD15, granulocytes; CD3, T-cells; and CD20, B-cells), and isolated using a FACSVantage flow cytometer. Each population was sorted twice to ensure purities of at least 99%. CD34 cells were obtained from discarded aliquots of G-CSF-mobilized peripheral blood stem cell collections from cancer patients. For each sample, the PCR results represent the pooled average of cells from 2 individuals performed in triplicate or quadruplicate.

Example 6

OCT6 RNA Levels in Leukemic Blasts

Total RNA was extracted from leukemia specimens using QIAGEN RNeasy midi kit. 150 ng of total RNA were used as a template for the first strand cDNA synthesis with the Oligo (dT) primer using the super script system (GIBCO BRL) according to the manufacturer's protocol. Quantitative real-time RT-PCR was performed using an iCycler thermal cycler with methods similar to those described above for the Roche LightCycler. The results represent the average of 3 independent determination performed in duplicate.

Although illustrative embodiments of the present invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method of screening candidate substrates of the organic cation transporter 6 (OCT6) comprising:

a. providing a test agent;

b. providing mammalian cells or a mammalian cell line which express OCT6;

c. incubating the test agent with the cells or cell line; and d. determining whether the test agent is a substrate for OCT6, wherein the mammalian cells or mammalian cell line provided in step b, are leukemia cells or a leukemia cell line, respectively.

2. The method of claim 1 wherein the test agent is coupled to a detectable substance.

3. The method of claim 2 wherein the detectable substance is selected from the group consisting of extrinsically activatable enzymes, prosthetic groups, fluorescent materials, luminescent materials, bioluminescent materials, radioactive materials, positron emitting metals using various positron emission tomographies, nonradioactive paramagnetic metal ions, immunogenic tag peptide sequences, extrinsically activatable toxins, extrinsically activatable quenching agents, and antibodies.

4. The method of claim 1 wherein the step of determining whether the test agent is a substrate for OCT6 comprises analyzing whether the test agent is located intracellularly.

5. The method of claim 1, wherein step (d) comprises determining the viability of the cells or cell line.

6. The method of claim 5, wherein the viability of the cells or cell line is determined by applying a dye to the cells or cell line, wherein incorporation of the dye by the cells is indicative of death of the cells or cell line.

7. The method of claim 6, wherein the dye is trypan blue.

* * * * *

SEQUENCE LISTING

```
<160> NUMBER OF SEQ ID NOS: 14

<210> SEQ ID NO 1
<211> LENGTH: 1734
<212> TYPE: DNA
<213> ORGANISM: Homo sapiens

<400> SEQUENCE: 1

atggggtccc gccacttcga ggggatttat gaccacgtgg ggcacttcgg cagattccag      60

agagtcctct atttcatatg tgccttccag aacatctctt gtggtattca ctacttggct     120

tctgtgttca tgggagtcac ccctcatcat gtctgcaggc ccccaggcaa tgtgagtcag     180

gttgttttcc ataatcactc taattggagt ttggaggaca ccggggccct gttgtcttca     240

ggccagaaag attatgttac ggtgcagttg cagaatggtg agatctggga gctctcaagg     300

tgtagcagga ataagaggga gaacacatcg agtttgggct atgaatacac tggcagtaag     360

aaagagtttc cttgtgtgga tggctacata tatgaccaga acacatggaa aagcactgcg     420

gtgacccagt ggaacctggt ctgtgaccga aaatggcttg caatgctgat ccagccccta     480
```

-continued

```
tttatgtttg gagtcctact gggatcggtg acttttggct acttttctga caggctagga    540

cgccgggtgg tcttgtgggc cacaagcagt agcatgtttt tgtttggaat agcagcggcg    600

tttgcagttg attattacac cttcatggct gctcgctttt ttcttgccat ggttgcaagt    660

ggctatcttg tggtggggtt tgtctatgtg atggaattca ttggcatgaa gtctcggaca    720

tgggcgtctg tccatttgca ttcctttttt gcagttggaa ccctgctggt ggctttgaca    780

ggatacttgg tcaggacctg gtggctttac cagatgatcc tctccacagt gactgtcccc    840

tttatcctgt gctgttgggt gctcccagag acaccttttt ggcttctctc agagggacga    900

tatgaagaag cacaaaaaat agttgacatc atggccaagt ggaacagggc aagctcctgt    960

aaactgtcag aacttttatc actggaccta caaggtcctg ttagtaatag ccccactgaa   1020

gttcagaagc acaacctatc atatctgttt tataactgga gcattacgaa aaggacactt   1080

accgtttggc taatctggtt cactggaagt ttgggattct actcgttttc cttgaattct   1140

gttaacttag gaggcaatga atacttaaac ctcttcctcc tgggtgtagt ggaaattccc   1200

gcctacacct tcgtgtgcat cgccacggac aaggtcggga ggagaacagt cctggcctac   1260

tctcttttct gcagtgcact ggcctgtggt gtcgttatgg tgatccccca gaaacattat   1320

attttgggtg tggtgacagc tatggttgga aaatttgcca tcggggcagc atttggcctc   1380

atttatcttt atacagctga gctgtatcca accattgtaa gatcgctggc tgtgggaagc   1440

ggcagcatgg tgtgtcgcct ggccagcatc ctggcgccgt tctctgtgga cctcagcagc   1500

atttggatct tcataccaca gttgtttgtt gggactatgg ccctcctgag tggagtgtta   1560

acactaaagc ttccagaaac ccttgggaaa cggctagcaa ctacttggga ggaggctgca   1620

aaactggagt cagagaatga aagcaagtca agcaaattac ttctcacaac taataatagt   1680

gggctggaaa aaacggaagc gattaccccc agggattctg gtcttggtga ataa         1734


<210> SEQ ID NO 2
<211> LENGTH: 578
<212> TYPE: PRT
<213> ORGANISM: Homo sapiens
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (268)..(269)
<223> OTHER INFORMATION: Xaa can be any naturally occurring amino acid
<220> FEATURE:
<221> NAME/KEY: misc_feature
<222> LOCATION: (274)..(275)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid

<400> SEQUENCE: 2

Met Gly Ser Arg His Phe Glu Gly Ile Tyr Asp His Val Gly His Phe
1               5                   10                  15

Gly Arg Phe Gln Arg Val Leu Tyr Phe Ile Cys Ala Phe Gln Asn Ile
            20                  25                  30

Ser Cys Gly Ile His Tyr Leu Ala Ser Val Phe Met Gly Val Thr Pro
        35                  40                  45

His His Val Cys Arg Pro Pro Gly Asn Val Ser Gln Val Val Phe His
    50                  55                  60

Asn His Ser Asn Trp Ser Leu Glu Asp Thr Gly Ala Leu Leu Ser Ser
```

-continued 65 70 75 80

Gly Gln Lys Asp Tyr Val Thr Val Gln Leu Gln Asn Gly Glu Ile Trp
85 90 95

Glu Leu Ser Arg Cys Ser Arg Asn Lys Arg Glu Asn Thr Ser Ser Leu
100 105 110

Gly Tyr Glu Tyr Thr Gly Ser Lys Lys Glu Phe Pro Cys Val Asp Gly
115 120 125

Tyr Ile Tyr Asp Gln Asn Thr Trp Lys Ser Thr Ala Val Thr Gln Trp
130 135 140

Asn Leu Val Cys Asp Arg Lys Trp Leu Ala Met Leu Ile Gln Pro Leu
145 150 155 160

Phe Met Phe Gly Val Leu Leu Gly Ser Val Thr Phe Gly Tyr Phe Ser
165 170 175

Asp Arg Leu Gly Arg Arg Val Val Leu Trp Ala Thr Ser Ser Ser Met
180 185 190

Phe Leu Phe Gly Ile Ala Ala Ala Phe Ala Val Asp Tyr Tyr Thr Phe
195 200 205

Met Ala Ala Arg Phe Phe Leu Ala Met Val Ala Ser Gly Tyr Leu Val
210 215 220

Val Gly Phe Val Tyr Val Met Glu Phe Ile Gly Met Lys Ser Arg Thr
225 230 235 240

Trp Ala Ser Val His Leu His Ser Phe Phe Ala Val Gly Thr Leu Leu
245 250 255

Val Ala Leu Thr Gly Tyr Leu Xaa Arg Thr Trp Xaa Xaa Tyr Gln Met
260 265 270

Ile Xaa Xaa Ser Thr Val Thr Val Pro Phe Ile Leu Cys Cys Trp Val
275 280 285

Leu Pro Glu Thr Pro Phe Trp Leu Leu Ser Glu Gly Arg Tyr Glu Glu
290 295 300

Ala Gln Lys Ile Val Asp Ile Met Ala Lys Trp Asn Arg Ala Ser Ser
305 310 315 320

Cys Lys Leu Ser Glu Leu Leu Ser Leu Asp Leu Gln Gly Pro Val Ser
325 330 335

Asn Ser Pro Thr Glu Val Gln Lys His Asn Leu Ser Tyr Leu Phe Tyr
340 345 350

Asn Trp Ser Ile Thr Lys Arg Thr Leu Thr Val Trp Leu Ile Trp Phe
355 360 365

Thr Gly Ser Leu Gly Phe Tyr Ser Phe Ser Leu Asn Ser Val Asn Leu
370 375 380

Gly Gly Asn Glu Tyr Leu Asn Leu Phe Leu Leu Gly Val Val Glu Ile
385 390 395 400

Pro Ala Tyr Thr Phe Val Cys Ile Ala Xaa Asp Lys Val Gly Arg Arg
405 410 415

Thr Val Leu Ala Tyr Ser Leu Phe Cys Ser Ala Leu Ala Cys Gly Val
420 425 430

Val Met Val Ile Pro Gln Lys His Tyr Ile Leu Gly Val Val Thr Ala
435 440 445

Met Val Gly Lys Phe Ala Ile Gly Ala Ala Phe Gly Leu Ile Tyr Leu
450 455 460

Tyr Thr Ala Glu Leu Tyr Pro Thr Ile Val Arg Ser Leu Ala Val Gly
465 470 475 480

Ser Gly Ser Met Val Cys Arg Leu Ala Ser Ile Leu Ala Pro Phe Ser
485 490 495

```
Val Asp Leu Ser Ser Ile Trp Ile Phe Ile Pro Gln Leu Phe Val Gly
            500                 505                 510

Thr Met Ala Leu Leu Ser Gly Val Leu Thr Leu Lys Leu Pro Glu Thr
        515                 520                 525

Leu Gly Lys Arg Leu Ala Thr Thr Trp Glu Glu Ala Ala Lys Leu Glu
    530                 535                 540

Ser Glu Asn Glu Ser Lys Ser Ser Lys Leu Leu Leu Thr Thr Asn Asn
545                 550                 555                 560

Ser Gly Leu Glu Lys Thr Glu Ala Ile Thr Pro Arg Asp Ser Gly Leu
                565                 570                 575

Gly Glu

<210> SEQ ID NO 3
<211> LENGTH: 123805
<212> TYPE: DNA
<213> ORGANISM: Homo sapiens

<400> SEQUENCE: 3

aagcttgtcc aacccatggc ccacgggcca catgtggcct aagatggctt tgaatgcagc     60

ccaacacaaa tttgtaaact ttcttaaagc attgagatat ttttgcaatt ttcttttta    120

gctcatcagc tatcgttagt gttagtgtat tttatatgtg gtgcaagaca attcgtcttc    180

ttccaatgtg gcccagggaa gccaaaagat tggacacccc gtgagatctt ctaggcgact    240

ggcccccagt gaaattgtga tcacggagga tagtagagtc ccggtagtac acataggaga    300

tgttccacaa actccatatg atcagcaccg ttttcgggag gccccacact gtgccgaaca    360

tcatgaatca gtgagggttt aggaagcaca tcaacctccc agtgtttggg agctgctgtt    420

ttaagaaggt cccgtttacc attctactgc ccacatgaag agtgaagact aatccgtgga    480

caggatgcct ctccagtcta gctgtgcccc gctccctctt tctcatctaa atcgaaccct    540

tttcctgtgg attgagatga aaagtccttg aacgcaccac cttgtgctgc taggtcagtc    600

tagacaatat taagtcacat ccattaagtt ttccttaaag aaaatgtttg aaatatttct    660

tccttcagtt cgatactaag tgtattttgc cacaagacac ttcctgatga cccaatttca    720

ggtccccatt cttttatcta tgtgagaatt ctccactttc agactctgct taatttaact    780

ctctctgaaa atgtgcaagt tcataaaaga aggtgaaata attactacgg tacatacaaa    840

gaggtgaaca tttcttttt atgtacaaat tgtgtgttac cccaagtgga ctttcctggg    900

cccgcctcct ccttctgtcc caggatcctg gcccagctct gtcccccaat gaactgcaga    960

ggtagagggg taaagaagag cagttgagtg gctcagattg ctgcctgaac tctggaccga   1020

ggagcaatca cgagtaaccc caaaaactgc ccattggttt gcgcactcat agcatgaaaa   1080

caagttccgt tcttttgtgc tgtcctggaa catcagccag ctcttaagtc acgttgcccg   1140

gattcatgtg ctcctgcaat gaaaggccct attgtcaaca aggctggtca acaaggcaaa   1200

gcaaagtttg acccgtgcat caaaacctgg aacatcctga cttgttacgt gctgagaaat   1260

gtgtgcttag tattgtatta aagtaaatgg ggaggggcag tgtctttaaa aatacccaaa   1320

gcaaagaaaa atagatacta tctgctcaat gtcccagagt agaagttttt aaaatgacct   1380

gagaaatagg tttattgctt tcattgcttc cttccttctt cttcctcctt ctctgacatt   1440

tggccctcct ctctaaaaac ttcccctcat agtgacccca ggctcctgtt gggaagtctc   1500

acccactgtg tgggtgaaca agcaaagcaa ctgttaaaag tgttcagata acatggacaa   1560

aaaacacatg gaaaagctga tatcgagttc cattgggttt ggagtggttc ttgcgggcaa   1620
```

-continued

```
aggatgcagt gagctgaaca tacattaaaa atacaaaccc ttaagagctg actgggtaag   1680
acttaagccc agtatctttc agagatgagt gtctaggtgc atcacccaga tcttagcctg   1740
cctgagtgta ccagtgaacc tgcccaggtt ttagtttcct tttctataaa atgatagctt   1800
ggttctgatg atcttcaggc tcccttggga ggtccttgag gcttcagctc aaaccctagc   1860
tctgctatct acctcttctt ggtgctgaga ttccatgata tccttcaatt attgtgggac   1920
tgacttagta gaaggcatca gagggaatgg aagcctctac attatcaatg cagaaattga   1980
ggcaagaggc caacattatt gcacaaaaca tggcagatgt tggaatgaag aagacagtga   2040
gacacaggca gcaacagagc ctccttaatc tctgacccaa aagagtcttg acttgaagtt   2100
ccccaagctc cttcttttct cccaggcact cactgctttc aaagcgactt caatctcaag   2160
ttgggagatg tggcccagtt cagggtctgc cgcagactca ggcaccatcc cttctcctat   2220
ctcagtttct tcactggcaa atggaaggta tacaattaga tgatttttaa agccaagctc   2280
agagctaaca tccacaattc caggaattcc aggaaatgca cactaaaact aaggttctga   2340
aacaagtaaa aaaacagacc aaatgttcga accaacgatt ttcagacatt ggagcacagg   2400
tggcacagga aacaagtgag gtgagtcctg tgattgcccc agcttgctgc ctggagagac   2460
tttccaggcc atggaacagg gacatggaat acaggtggag cacagccata tccctgtgta   2520
gaaggatggg gctggggtcc cagggacact tgtgcaccta gaactcacag gagagaatac   2580
tggagagaag aaagctgcac acggagagaa ctctgggctc tgcagagtgt catctttggg   2640
tcttcagcaa agtattgatc agcacatgca tgtgaggaaa agaaatgagg ccagaaaaag   2700
aatcacccaa aaagattaga gggaaccatt cctagagctc ccaccagcca gagaatagcc   2760
cctgtggcca ccaaccacag ttgaaaacct tctaattcat cgggcactga gtagaacact   2820
ctgagtattg tctcagtaat gcagcccaat tcagcttact ctaaagtctc ctgtggtccc   2880
tcctgacaag gcttaaaagc aagtcttggc tggcacggtg gtgcgtgcct gcagtcccag   2940
ctatccagga gggtgagggc tgaggcagca tgacgactgt tcaagccagg agttcaagac   3000
cagcctgggc aacatagtga gattctgtat cttttttttt tttttttttt tttaaaaaaa   3060
aaggccgggc acggtgtgtc aaccctgtaa tcccagcact ttgggaggcc gaggtgggta   3120
gatcatctga ggtcgggagt ttgagacaag cctgaccaac atggagaaac cctgtctcta   3180
ctaaaaacac aaaattagtc gggcgtggtg gcacaggcca gtaatcccag ctactcgcga   3240
ggctgcggca ggagaatcgc ttgaacctag gaggcagagg ttgcagtgaa tggagatcgc   3300
gcatcgctgt ccagcctggg caacaagagg gaaactccat ctaaaaaaca aaacaaacaa   3360
acaaacaaaa aacaagtcat gaaaggatcg aactgttttc aagtaaatta actgtgttct   3420
agaacaacac tcaaaagttt ttttgtgtgt ttgtttgttt tttaaagaat atccaggcca   3480
ggcatggtgg ctcacaccta taatcccagc actttgggag accgaggaag gtggatcact   3540
tgaggttagg attttgagac cagactggcc tcaaacatgg tgaaactctg tgtcttctaa   3600
aaatacaaaa attagccagg tgtggtgggg gaggtgctgt agtcccagtt actcaggagg   3660
ctgaggcagg agaatcgttt gaacctggga ggaagaggtt atactgagct gagattacgc   3720
cactgaactc cagcctggga gacaaagtga gactccgtct caaaaaaata aaaagaaaaa   3780
gaatatccag cactcagcaa gataaaattc aagcaagaga aacatgaagg aaattataac   3840
aagacacatc ataatcaaat tgctcaatac cagtgataaa gagaaaatct taaaattaac   3900
aacaggaaaa aaattatgtt agaaacagga gaacaaagat aagaatggca gcagagttca   3960
```

-continued

```
tgtcagaagc aagcaagtga gaagacagag gaacaataat ctttaaagta atcagagaaa   4020
aatattgtca acctagaatt ctaggttttt gggtgttttt tttttttgt ctttcacatg   4080
aaatggccac taattctata cccagcaaaa atgtctttca aaaacaaatg caaaatactt   4140
tttcaaacat acaaaagctt aaaaaatgat cctctgagga cctatactat aagaaatgtt   4200
aagggatgtc cttcaagcag aaggacaatg ataccagata aaattctggc tctacaaaaa   4260
gaatgaagag ttctggaagt ggaacttcaa ctactctaaa catgcaacaa gctatgaatg   4320
gggagtcttt ctgtggaggc ttccaggacc caaaagtgag gacagagaag tactctttgc   4380
ctgagctgac acccaccaga gctgagaacc aaggattcct aagaggtgac atatgtggct   4440
gtgttaccgc caactccacc ttctacccag taagactggg aaggagggag agagagaaat   4500
aagtctaagg gtcactggag cacaggacgt gtgaggagag gggacttcct gcccttcctg   4560
tggttatggg aaatggggtg gctgtgcttt cctccctagt aaggttctaa taaaatgatt   4620
ccacaaatat tggaatgtaa agtagctccc ctgttggaca tttgattagg aaaaggattt   4680
gctggcttat tcatacatca ttagggatag aggagggtct tggagaaaga agaaagggca   4740
caaagaagag ctgcaggggc agtctgaact cacccagttg gtcagggcca gaaaacgcat   4800
ttcctgcagt tcaagtggat gctacttaga aggcagctgg atttgttcca tccctacccc   4860
aacagggttc tctctcctat ttaccgggga gctcaaagag tccgtagagt acatatccag   4920
tcatgggagt tgaggggcat ggaggtggtt gagcctggat ttaccatatc cgtgccctgc   4980
aagtctctct aaaagaaccc agatgtgtct tccagagaag gctagcacgt cgatgcctgc   5040
ctcacagcca gtcccagtgg gacaccgcta gagagaaggc taccactaga gagaaggcta   5100
ccactagaga gaaggctacc gctgccctgt tagtttacga ccctctgccc tttctctgtc   5160
ctacctctca gcccagcgca ctagaggaac tatttcccaa agcggaaagc gagagtggag   5220
gagtgtccca gaaatagacc tccctcattc agggtccagg tccaagcttg cactggaccg   5280
ggagagggca gtggcgctgg gagatgaggt gagagtagaa tcgtttggaa ttaatgtttt   5340
aaagtggact gagggttaat acctgaaaac agtggtaaaa ttttggaccc gcccaagatg   5400
taattaacag atctgctacc ctctggataa ggttgagcac atttgaaagg gcttcagaaa   5460
atgaaaaagc cttttctgtc tttaagaaaa caaacaaaca aaaaaaaaca aaacaaaaga   5520
acaaaaaacc tgtcttcccc caacaggcac aattacattt gtaaagatgg ttcccagcag   5580
atggtgaggt gctaatgagt cccaggaggg gctcaggaga aaactcacct tcaccacctt   5640
gctcctggtg actcccagca cacctggtcc agcctttcct ctgcagctgt tttttagtgc   5700
atggcctgtc ctcctggaag gaaaactgga gagcgtgacc tgatccaggg agcaaaggct   5760
tcatgtgccc tgtggccttt ttcagcatgg ttagcggggt gggactctgg gcccactctc   5820
aggtttgggg ccatcactag gtcctggcag ctgcagtcca ggctggcccc acaggaggcc   5880
acaggcggtg gctccacctg aggagaaggt ggcatgtggg taccccacct ggctctcccg   5940
ggaagggccc ttggcaacat ccgcagcagc ttggctccac cccagttgca gtcttgacat   6000
ttggttattt tctattcttt ttactctgca aataatacat gttcgttata caatcaggta   6060
gaatgtacaa ataagcaaat aaataaacaa atacttctca taatctcact accaaacagc   6120
cactgttaat aacatttttg tgtatttcct ctaagatcga gtatgaaata tttatatata   6180
tacatatata tatgtatata caaacaaaat ggattaatat tccatacgca tatgtgggac   6240
atttatattg tttacaactt tctgttatct taaataaggt gtgatgaaca cctttactca   6300
taattttttg tgcataattt ataattcctt cgaataactt cccaaaagga agctatacca   6360
```

-continued

```
gggaagttgc aagtttttaa actctagtag ctgaatttct agctagtagt ggtggaggag   6420
gaggaccttg agaaggaggt ggaggcatgg gaggagctgg gcctcagggg aggctcggga   6480
ggctgctcct ctcctttgcc tccttcggtt tccctgttta atccttccct ccgttctcag   6540
gctcctcttc ccctggtctt ctctttcatc ctttaattcc ttcacccttt gccccttctg   6600
ctatttcaac tctggatttt tcctccagtg ctcaaacctc attctgttcc attgaatgtc   6660
cctcattgaa tgtcgctcac tgcttggcct gccttcctac ctgtgtcccc accaggctcc   6720
ctgtggtgac cccgtggtgg cagcgtggac ttcctgccct ctcaggtttg tgtcctgcag   6780
ggaagagtga aggtcttttc tagtggctcc cacaatgccc tagggactct ctgattggct   6840
tggtgtaggt cacatgccca tctctgaacc aatgactatg cccgatcttc actgtggcct   6900
catctgggcc acctggtgga tccctggagt tgggatgaag cctcacccag cccacaggaa   6960
gtaaaagtgg gggcagagga gggcccttgg atgaaggtcg agctctgttc tgggaatagt   7020
gggaatatcc ttgaggcatt catctcccat agacagtgaa actctccttg cctatggaag   7080
gatatgacaa acgtgaagat tttgctttta aatgtaagaa ttgtcagtgt catacctaag   7140
aaatgacgga aaataatatt aaaaatttaa gagtgttaaa atagatcaac tgcaaacgtg   7200
tgttcccagg acacaaatct gaagggtata cattaactaa tagacgggtt atttttcttt   7260
aaagaaaaat cccttatatc ttatatatac acaagggatt cttaaggaag gacaacctag   7320
tcttcctttt cacccaaaat ttacagtgtt aaaaataatt ttatggccgg gtgtggtggc   7380
tcacatctgt aatcccagca ctttgggatg ccgaggtgga aggatcactt gaggtcagga   7440
gtttgagacc agcctggcca acatgctgaa accccatttc tactaaaaat acaaaaatta   7500
actgggcttg gtggagcact tctgtaatcc cagctattca ggaggctgag gcaagagaat   7560
catttgaaac tgggaagcag aggttgcagt gagccaagat tctgccactg cactccagcc   7620
tggcgacaga gtgagtggga ctccatctca aaaaaataaa ataaatagat gaataaataa   7680
ataaataaat aaataaataa ataaataaat aaacaatttt actattaact gagaaccttt   7740
tcagtgccag atcctgagct aggctcttga tgtgttgtta tttttaatcc ttacaacaac   7800
tctacaaagc aatcttagta ctcttcattt ccaaaggagg aaaaagaggc tgagagagat   7860
tgtataacct tccaacagtg acagcactag tagtgcccac caagtggtca agcccaggtt   7920
gtatgtaccg gagtgccctt cttggctaag aaaacctaaa attccctaac ttgtgtttgg   7980
ctgaatttct gagggctttg agtgcccaga gtgctcctgc tgcttcaaaa gctgcagctt   8040
cagctgcttt tgaacatctc agcgactgca gggacagaaa tagcactaag tggaaaaagg   8100
atccaaaaga agaatctaaa acttcagcta ttatatagac acaaagatat actacttagg   8160
tctttccaaa tggatgaaag gatgccacac ctaggttttc caaagaattc attccttttg   8220
gtgtggctga actggtgaga tgtaggggct tcttaaaagc attctgatgt catctcctgg   8280
taaagcctag ggcttgggaa ctgaaatgta caagaaataa acatgcagtg aaacacctga   8340
gagtctatcc tctttgtgtc tcccatcatt tctgcaggct gaagtttcca tttaattttt   8400
gcatcacatc tttagcacta ttggacatcc tagaaacctc attcacaaga tttcaagttt   8460
gaagtgatag tgtttgctac cagagcccct tttctgtcaa agaaattaga agcaggaagg   8520
ttgatgcatt cccccacagg tgagtcacca agaaaatgtt tgagtcttca aaaggcgatg   8580
gttccactct tagctggtga attccatgag catacaaagc tctgtttgta accctgtcac   8640
agaagaagaa tctgggatgt gttttttatt tggtacagga aataagaggt ggatgattcc   8700
```

-continued

```
agtttgtgga atttgacagt cttctgttca gtcagtatct cttattttgt tatgcttatt   8760
ttaacagaaa gaaaagaggt cttttagaat aatgtgaaac tcacactctg catggggaca   8820
ggtaaggagg gaagcctggg atgtgtgcag agaaaaggca gcatggctgt ttgactggag   8880
caaaggaaat gtggcatggg ggtggaggga cagggccacc tcagggagca ttgaaggttc   8940
agccatggag ttcaggcttt attctcaaag tagtgggagt taatgaaggt ttttgactag   9000
atgtatcaga attgtgtttt ctgtttgttt gtctgtctgt ttgtttgttt gtttgtttga   9060
gacagagtct ctctcagttg cccaggctgg agtgcggtgg tacgatctca gcttactgcg   9120
atctctgcct cctgggctta agccatccat cttcccaccc cagcctcccg agtagctggg   9180
gtcacaggtg catgccacca agtctggctt atttttgtac tttttttttt tttttttgt   9240
agaaaagggg gtttcgccat gttgtccagg ctggtcttga gctcctgggc tcaagtgatc   9300
cacccacctc agcctcccaa agtgctggga ttataggtgt gagccactgt gcctggccag   9360
aactgtttta gggagaacaa tttattaaca atataggaaa tagaacagaa acagagggtg   9420
gacataggca agcctgtgag atgtctacta tagagtccca ggctgacact ggaaggcagg   9480
cgttagcatc aagagtcaga atggaaaaga cgtcaggagg gagaagctac tatagagatg   9540
gaagttatgg gtcagagtgg ataacgaagg acaagatggt gctgcactgg gtgactgcat   9600
gggtggtggt gctgtgtaca gattggggcg aacgtggagg aagcacaagt gttgaaagaa   9660
gggatcatgg gtccactttt gaacatactg agtttgaggt ttcaatagga catctttgta   9720
gggatgcgta gaagacagtt ggaaatacaa atgtggattc agagacaagt ccagccttca   9780
gtggaactca gacaagtcca ggaagatgag gaggaagggg gctagagaaa tagtagagga   9840
agggggctag agaaatagta gagaaaggaa aggacagaga tctgcgaagc tgagggagga   9900
gttttaagaa aagggtgggc caggtgtggt ggctgtaatc tcaacacttt gggaggccaa   9960
ggcacagggg gatcacttga ggccaggagt ccaagaccag cctgagcaag atactgagac  10020
cacatttcta caaaaaaaaa aaaaaaaaaa aaaaaaaaaa agttatctgg ggcagtggtg  10080
ggcacctgta gtcccagcta ctcaggagac tgaggcaaga ggcttgcttg agcccaggag  10140
gtcgaggctg cagtgagcca tcataccact gcactccagc ttgggtgaca taatgagacc  10200
ttgtctcagg aaaaaaaaaa aaagagtggt gtggttagca gtatctgatt tagtaaaggg  10260
ctgagaaggt tgaggatgga cactggcaga ctttggcttt taccctcatc cctgtccagt  10320
aagagttctc tcaattccaa acatttaaaa gtgagtggga atcattaatg gaaccataca  10380
tttcaaaatg attaaaatgg aaaattctat gttatatttc tctataaatg agtaaatgag  10440
agaaaaacat taacatttaa aaaaatcata ttgttctcta catgtttctg tatgcttaaa  10500
acataataaa ttgctttgaa aagtaagtgg taggtcaaaa acagaagtat tgatacaaac  10560
cacactttgg agaaatgtga tagctaagtg aaggagggaa agcatgagtg actcagctta  10620
acgggtaaca ggaaagaaag aacttgtttt ttcgtttgtt tcgatgaggc aacttgttta  10680
tctttctggg ggccatcgct tacccaccag ctgcccccta cctttgttcc cgccttcatt  10740
gtggagtctc acactcaact caacctggaa acaactcaac ctagaaacaa cacggtgaag  10800
gtgagactga agatgggggc caggtggtgg gtaagtgatg gcccccaaaa aggtacgtcc  10860
acgtcctagc tcctggaact gtggatgtga ccttatttag aaagaggatc tttgcagagg  10920
taattcataa ggatcttgag atgagatcat ctggattatc caggtgggtc ctgaatccaa  10980
tgacaagtgt ccttataaag ggcagaagag gagaagacag agagaatagg aggagcccat  11040
gtgaagataa aggcaaagtt ggcagcgatg cagccacaag ccaaggaaag ctgggtatca  11100
```

-continued

```
ccaaaagctg gaaaggacag gaaggattct cccctagagc ctttggagga agcatggcac  11160
agctgacgcc ttgatttcag acctctgccc tctcagaacc gtgggagagt gtatttctgt  11220
ggtctgcagc caccatattt gttgtggtga tttgttaaag cagccctagg aatctaacag  11280
gggtggggag cttggccaca gtctgaggtc ctgagcagtg gggctgtgtc tcaggcttct  11340
cattttccac accccacccg gggccaacac aatcatttat tatgagttta ttcacttggg  11400
gcttaaattc acaggacagt atttctctca tagtgataac tttgtcttca tttttttcct  11460
gtctcgttcc cagtgggttt tagaaaatcc acagatattt tatttctttt taaatttttt  11520
tctcacactt ttaccccaga agatagaaag tcaacaaata ttttcgtact gatatctttc  11580
tcttttactt tcatttttta agctgggaca ttggcgccag cggggcccag ggcttgcaag  11640
gggagctcct ccctggagtc ccactcctgc cctggcacac agaccaggtg acggggggcc  11700
tgtgaccgag cagggcagca tgtggcaaag ggcagggtgc cagggagacc tccctctgat  11760
aactgctgtg catttgagct gctgatgggg attgtcccaa cccttctaag ggtcatgagg  11820
tgtcagctct cagcaaccag ggagactgga ctgcacaggg gacctcaggg ccaggcacct  11880
gaggaatggc gatccctgtc ttccccctga ctctgcctgg gtggagatag gtgttgctct  11940
ggctgagatc ctcctccaag ccagacctga ggttctattt ttgaggacca aaggaggtga  12000
gggatcttgg tctagggaga gctgacatag ctgccctccc tcctgtgcct gggaaacatt  12060
tttccttggg gactttcaag gtgtaagaac ctccaggagc cgctccagtc ctcttgtgtg  12120
ctgttgtctg gcagccctag gggagactgc tgggcagggt ggccctggga gagactgcag  12180
cagggttctg cgctgccaac actgtcactt cccagccacc cagacccagc ctcactggtc  12240
ctggtgcctg cctttctctt ccatcttccc cgggccagcg aggcactgag tcctttgctt  12300
ctttctcact tcatgcacct ctgcccttct ttctcgagct ggcttgccca agagtcctta  12360
tctggaacct ctggtctttg tacctcctgg cctgccctca gctgctccgt tgcctgggtc  12420
ccagtgcttg cccaccatat tcaggggaca tcctggactc cttggccacc acccagaccc  12480
ttctgtattc tgctcccccct aatacctcct ggtctctgca tgaacctccc actctgacca  12540
cactgcactg ttgtttcctg gacacacggc acccactcct gcctccatgc tcctgcttcc  12600
tccacctgga atgccctctc tgctgaccta ccacacactc ctttaagaac gaactttcct  12660
tcttccccca tagagccact tccacttgct ccaggccaca gagttctctc tcccgtgaca  12720
gtttccttcc tgtgcaatag tatcgcctct ggaacttcct cacctgccac ctggtgctgc  12780
tacatgtcca cgtatgtatg tacgctttca ttcattcttt ctttctaaca tttgttctga  12840
aaaaaataca tcatgtgcca ttatgcacca ggctctagaa tataaagatg agtaaaacct  12900
agtccctgag ttctagacgt ctccaggtgt ggtgtgtatg ctgcgtgcct cccactggct  12960
cttccagatc cagcctctgc tctgctcatg ccctgggcaa aatggcccaa agccaaaaca  13020
agcaaactgg ttcccctata accaaaccag acagcttggg gcctggcagt gccaggggag  13080
agctggcatg agcagggcag aggctgactc gtatggcgcc atccacaggc cccattgccc  13140
tctggcttct ggtgggctgt ggctagggag cccccccag gagagcagag gttgaagctg  13200
caggggctgg attcccctgc acctcgctgt ggggtcaccc tgtcggctgt gtcacgattc  13260
ctgttagttc ccactctgct gtctctggat ctagtgcctg ttcccttcac cctcaggcca  13320
ggggtggagc cctcccccca gcccccaacc ccataccctg ctcacacctt tgcaaatagc  13380
gtctttacta aactctccca agtgtctata tgtgccattt cctttccgcc cagcaccctg  13440
```

-continued

```
agtgaaagtg ttttgaaacc agggagaagc tggaggacag aggcacataa ggtgccgagg  13500
acaggagaga ctgcacactc tttgtagctt tcacacaacc agagtccagt gcacagagtg  13560
cgtactcatg tctacaaaag acacttcact cttcttaatt caacccatat cccactctag  13620
tgcccatgtg gatcttttta tcattgcagg atgaccaaag tcattaaaac ttcgtaaaaa  13680
gcctgcttta gtgaagagct tctggcgacg gcctttgaat ctgtgcccct gagggctcca  13740
gggcaggact ccaactggtg gtgtaagact tgctgtcctg atgtgggtgg cagttgctag  13800
aagagggact gtttcatttc attagcagtg aagtgtgctg tcagccggca gtgatagcca  13860
tgggacaaga tgcaacccaa tctgactctg aaacatcctg tcctagccac cgctgagctc  13920
ttccccctta gggggtcgcc agaagagtat tgattggaca aggagagaga gccctcttga  13980
agaggaatgg tgctaaagtc aacctgaagc cttctgaaaa ttcagcggcc ctagaactgc  14040
cccaaatgct atttactgca aagcagaatt ctgtatccag aggggttgtc ctggactcca  14100
ctcaagaggt ttagctttta aagagcctaa aggattcctg gcttatctgt tgggtgagtg  14160
tgagagtcag atcccaaagg attatatgat atgatggatg atttagcacg ctgcttcaca  14220
ggaatttaac agaaatataa gattgctcag ctggagcaga attgtctaag agacaaacct  14280
ttttaaaacc ccactaatgt ataacctcaa gccacaactg gattcaatta ctgcgtggaa  14340
agaaaggcat tttcttataa agccactctg tttccgtgcc tggctgtgag ctgggtcagc  14400
catgacaaag ataagcttgt gtgttgtttt tggttgtttt tcctttcaag ctcttcccct  14460
ggcactgcca ggccccaggc tgtttggatc ggttgtgtgg aggccagttt acttgttttg  14520
gctttcagcc tttctgttca gcattgatga tagaagagtg ggcctgtgtc ctgcgtggcc  14580
agtgatgggc tatcagcatg gcttggtggt ggcaccatgc ccaggtgccc cttaggaggc  14640
acacaatgtt tagaagccac acagtttgtg aggaaggtga acattctaag gaaggagact  14700
ggcagagatt gtaggggact cgagaggggt ctgggcacag aagggtctgc gtattgacat  14760
tctcaaatat taatacaaat acctaacatg tggagtgctt actctctcta ggccctgtcc  14820
taacagcttt acatatatta cttcatttaa acctcccaac aatcctgtga agtaaatgtt  14880
attattatat ccactttaca gacgaggaaa ttgaggaaca gaagggtaca tagtttgccc  14940
aaggtcacac agtaagtagc tgagggccca cgtgcttgat cactccattg tcaaagagta  15000
tgggacagaa actttaaaac catgacatgt gcatttatgc agacactaaa tatttttaca  15060
gtgttcttta ttcattattt tccttaacat agtatattaa tacctgaaag gcatatttgt  15120
actgttatat agcatgtttg aaatcacaag aatggaaaga cccatttggt tcagtctgcc  15180
ttggggaaga taagaatata tatatagaaa gacctagcca gtgcaataag gcaagagaaa  15240
gaaataaaag tcatccaaat aggaaagcaa gtcaaactac ctctcttcac tgactgtatg  15300
attctatact tagaaaaccc tgaagactct gccaagaggc tactagaact gatcaatgat  15360
tctagtatga tttcaggata caaaattaat gtacaaaaat cagtagtatt tctatacact  15420
aaaaatatct agactgagag tcaaataaaa aacacagtcc tatttacaat agccatgaac  15480
aaaatgaaat acctaggaat acagctaacc aaggaggtaa agatctctac aaggagaact  15540
acaaaacact gctgaaagaa ctcagagatg acaccaataa atggaaaaac attccatgca  15600
aatgggttgg aagaatcagt atcattaaaa tacccctact gcccaaagca atttacagat  15660
tcaaagctat tcctatcgta ttaccatgtt attcttcaca gaattagaaa aaactattct  15720
aaaattcata tggaaccaaa tagccaaagc aatcctaagt aaaaagaaca aagccagagg  15780
catcactcta cctgagttca aactatacta taaggctaca gtaaccaaaa cagcatgata  15840
```

-continued

```
ccagcacaaa aacagacaca tagaccaatg gaacagaata gaaagctcag aaacaaagct  15900
gtgtgcctac aaccatctga tcaacaaggc tgaccaaaaa aaaaaaaaaa ggactttcta  15960
ttcaataaat gatgctggga tagctggcta gccatatgca gaagaataaa actagaccct  16020
tacctttcac cgtatacaaa agttttctca agatggatta aagatttaaa tataagacct  16080
caagttataa aaatcctaga agaaaaccta ggaaataccc ttctcaacat tgaccttgac  16140
aaataatttt tggctaagcc cttaaaagca attgcaacaa aaaacaaaaa ttggcaagtg  16200
ggacctaatg aaatgaaaga gcttctgcac agcaaaagaa accatcaaca gagtaaaaca  16260
gacagcctac agaatgggtt gcaaaatatt ctcaaactat gcatgtgaca aaggtctaat  16320
atccagaatc tataaagaac ttaaatcaac aagcaaaaac caaataactc cattaaaaat  16380
gggcaaagga catgaacaga tacttctcaa aagaagacat acaagcagcc aacaaatata  16440
tgaaaaaagt tcatcatcac tgatcatcag agaaatgcaa atcaaaacca cagtgaaata  16500
ccatctcaca ccagtcagaa tggcttctat gaaacagtaa aaaacaacag atgctggtga  16560
ggctgtggag aaaagagagt gcttatacag tgttgatgag aatgtaaact agttcagcca  16620
ctgtggaaag cagtttggag atttctcaaa gaacttaaaa cagagctacc atttgaccca  16680
gcgatcccat tattgggtat ctacccaaag gaaaacagat cattatacca aaaagacaca  16740
tgcacctgta tgttcatcac agcactcttc acagtagcaa agacatggaa acaatgtagg  16800
tgcccatcag cagtggactg gataaagaaa gtgtggtgca tatacaccgt ggaatactat  16860
actgccataa aaaagaatga aacatgtcct ttgcagcaat gtggatggag ctggaggcca  16920
taatcctaaa tgaattaatg ctggaacaga aaaacaaata cccgtgtcct cacttataag  16980
tgggagctaa acattgagca cacatggtca taaacatgcg gacaacagac actgtggact  17040
actagaggga ggagggaaga agcaggatgt gggttgaaaa actacctatt aggcactatg  17100
ctcacaaact aggtgcaatg tgcccatgta acaaactggc atgtgtaccc cctgtatcta  17160
aaataacagt tgatattttt aaaaaagaat atatataaac atatatatta tatgtaaagt  17220
atatatattt tagggcctgg cacatgatac taatgactca tatggaaagc cagcgagctt  17280
tcataagata ttgcacacaa ggaaagttaa gaaccagctt gctgggctgt ctgatcacta  17340
gctcaggctt tctgcatgag cttggctttc tgataggaaa atccagggct ctgagcctgg  17400
aatgaacata tgtatggccc aagctccacc agcagcttaa ttcactgtga caattatcaa  17460
ttggttgcct ctcagctcca aattcaccct tcattactcg ctcttcgaga atgatgaggg  17520
ttaggctttg tcagcaggaa gtcctggagg gacattgtga gagaaaatgg ctgctcttcc  17580
tagttccagg gggcttgctt tctcaggctc ttgcagcctg gacagctttc tctgcagccc  17640
caggtggcca gcagcctgag atgccttcct gcagacagct tccctgggca cctccctgtg  17700
aatgacctct gccagatccc cctcaggaag ctttgcagta gggtgcacaa aatggggtac  17760
cgccccttgg atggcttccc tggcacccgc ttgggcagct ttgcagtggg tgccttccta  17820
agcactccag agacaggttt ctggacagcc tcagcagtga ggcccctcat gaacttttcc  17880
cccatcctga aagccctggc cagaccctct tccatgaggc ctggatctca gctcttcctt  17940
gaatgctcta tctcagtcct aggggagata gctgctgtct gtatcagcta ttcctatatt  18000
ctttagagct ctctttaccg gttactagcc agtctttcat cacttcaatc ccctgttact  18060
aatttgttat agttaatttt cttgtagaaa ttactgattt gtctcctgtt cagagtttag  18120
tacattcacc atattttttc agcccaccat ttaaaataaa aatgtaactc cctttacatg  18180
```

-continued aaaaacactg caagaaacat ggaagcaaca aaaacaatat gaaaacactt tcactattaa 18240
tttactaagt tagaagattc tatattctct ttcagttctt ggctatctgt ctgatttttc 18300
cgtatttgta acctgcgtgc ataattgagt ctgcactcta agtttatgag ttgactttag 18360
cttacgtaag cagtttgata gccctatagt ccccaagtag ccactggtca catagtcctt 18420
gcatttgtca tcaggcaagg caatataata ttccattttc ttcacgtgct caaatttgct 18480
aagctagttc ctgattgtgg gatacatggg ttggttcatg cttttccata ttacaaaaag 18540
cacagatcaa aatattttg ttcaagttgc atcaacccca cctaattttt tctcttgttt 18600
cttcctttct cgattctcta acagttgggc tcacatattt tcccaccgat agacaagaga 18660
ttaccagaaa aggggtgagg aatccagaga gaatgtctgc ataagaagga gggtggagat 18720
ttcttactga actaaaggct tcaagaattg gcaaatacct gctcagtaag tatctcctgc 18780
caggaaaaga accagtctca gaggtggagg cagaggggaa tcattggttg gagaggagga 18840
atttagactt gggaagcaag gtcgttctag agatcaagac tgtcttttct tcagtctctc 18900
atagtgtaac ctgtgactaa tgcattagtc atactgagca cgtggaaact acacaatata 18960
cactagaaaa acattttagt tctcaagaat agcctcaaaa tcagacaatg cctgaagtaa 19020
ttgagagtgg gaagcacatt gtgcaagtga ttactgctct ctgacatttt aaaccaccaa 19080
taactcaatt gtttcctgaa ttcccagaga gtcagagaac atgaaaaaac cttctttgtc 19140
actcagtgga gtaaatgtta atctcatact taaatctttt tctttttcac ataaaagtgt 19200
tcctggtata aagcccagaa agaagcttaa gcatagcacc ccctgtattg ttcattttct 19260
tgttcataca taatgtttac ctggaaattc tttatttcac acttattctt aaaagtaatt 19320
ttgctgagtc tccaaacaac tgttttcaaa attttcttcc atttttctga cttggaatca 19380
ctagaaatta aaactgtgct tttcttaaag ctctataaac tgaagctagc aacttaaact 19440
tcgggagaaa caatagcaac atatgtaatt aatatatata tatatacaac ttttgtgcct 19500
gcctgatgat gtatggactt ctcagaaagt tcacttgaac acccgattcg agccacaatc 19560
cagaaaaatc tgtcaggttg ctactgcaac ctgaagatgc ttgagagact ctagaaaaac 19620
tagtctatca actgctccag gacattcacc tttgctttcc ttctgtttct gtagaaatgc 19680
ctcctattaa agatctgttt gcctgcatca tatatagtgg cccaccctgt ctgcaatgcc 19740
acctcctaga atgagacaca gctgtttaac tgatctattc tcaggactaa gagactgact 19800
aaagaagata cgaggatgat atatttaaat ttgctctttt ctgttccttc caatttgtct 19860
ttccatttct ttgtctatct ctaacaagct ctaaaacaaa tttctccaaa gctatctgct 19920
tgtcttttaa tatgtgaatt tttttaagtt tcaaagtgat gactgaaata tttcacccca 19980
aaatatggct ccctggtata gtgagtatgt tgaattcaac acccttagag atcaacaagc 20040
actagaagag gcttttccca cctacataaa gataggaatg atccaccgag gagaacaatt 20100
gctcttgttc tcctccgtta tctcattatc cattacagga aagaagacca agaatgtaac 20160
cacacctgaa cggaaccttt ttgagataat gactgtctct aaggatcatt tacattccaa 20220
gaactactta caagttaatt tctgctccct gatccaacca ttttccctgg tgatcattta 20280
ttgcccctca atacaattat tctcctcccc attcccataa cccattctat ccggattcaa 20340
gcccccattc tttctgtaac ctcaagatag caggtaagct gctgtaccac attgagaagt 20400
tgggtcttca ttctgaaggt tcccatgtgt acacactaaa taagtttgta taccttttcc 20460
cctatttatt attattattt ttgagacgga gactccctct gtagcctagg ctggagtgca 20520
atggcgtgat cttggctcag tgcaacctcc acctcccagg ttcaagcgat tctcctgcct 20580
cagcctcctg agtagctggg attacaggtg cccaccacac ctggtgaatt tgtatatttt 20640
tagtagagat ggtgtttcac caagttggcc aggctggtat cgaactcctt acctcaaatg 20700
atccacctgc ctcagactcc catagtgctg ggattacagg cgagcaccac cgtgcctggc 20760
catctattcc cctatttttt ttttaaagta gttttgctgc acatgcaatt ctcatttatt 20820
ttcgcttatc actttgaaga tattgttcca caattgtcta gtttctgttg ctgtataaag 20880
gtatgttgct aataattttt gtagatgatc tgtcattttt ctgctttaag atctttctga 20940
gtttagcatt ctgcaatttt attactatct tttgcagact gggtgtggat tttaaaagct 21000
ttatcttgca tggtatatgg tgtgcatctg taactgccca gtaagttctt cttgcctgct 21060
gcccagatag agccaattta tcaagacagg agaactgcaa tggagaaaga gtttaattcg 21120
tgcagagttg gctgaatgga agagtttaat acacatagag caggctaaat ggaagactga 21180
agctttatta ttactcacat tagcctccct gaaacacagt cttgcaggca gggggctagg 21240
gaatggggag tgctgattgg ttgggttgag gatgaaatca cagggagtcc aggctgtcct 21300
cttgctctga gtcagctcct ggatggtggc cacaagacca gaggagccag tttactggtc 21360
tgggtggcgc cactggatcc atcagagtgc agagtctgaa aaatattcca aacaccaatc 21420
ttagatgtta ttcacaaaag caattagaag gttaggaatc tggtgccctc tggctgtata 21480
actcctaagc cataatttct aatcttgtgg ttaatctgtt agttttacag aggcagtttg 21540
gtccccacac aaggaggagg tttgtttcag ggaggggctg ttatcgtctt tgtttcaaac 21600
tataaactaa attcctccca aagttagttc agcctatgcc caggaaggaa gaggggcagg 21660
ttggaggtta aacgcaggat ggagtcagtt aggtcagatc tctttcactg tcataacttt 21720
ctcactgttg taatttttgc aagggtagtt taactttcta tatctgggaa ctcatctctt 21780
atcagttctg gaaattctct tttattatct tttttaatat tggtttttca tctattttct 21840
ctagtctttt ctgccactcc tattatatta aatcttattc tatcctctat gtcttgaccc 21900
ctctttgatg ttctatcttc ctgtctcttt gtgttatatt ccaggtaatt tcttcagata 21960
tattagttaa ataattctct tttcagttgt ttcttatata ctgtttaatt tggtcattga 22020
gtttttaatg tcaacaacta tatttttcat ttataaatgt tttacttggc tctttttcaa 22080
atctgcctgg tcatatttca tagtatctgg gttacttcca tacatttatg atctcatctt 22140
ggatttcttt aaatatttcc tatacaacac ttggtatgca tgattttgca tttaaaatgc 22200
actattttgc atttaataat tctaatacca aagtcttggg agtgtaaatt tattgtttat 22260
tatttttgct ttcttttcca tatgctggct tattctcttg ctgtttggtg gtggtctttg 22320
atcctgaaca cattgtgctt gatcactggg agtcttgggg tcctaagttg aagttatgta 22380
ctccagaaga ggttgtcact tgcttcttcc atggcccaga ggactggttg agcctccttc 22440
aggggtcatg gtttacagtg ggagacctga agttgacttt tgcaccttgt aatgggcttg 22500
gggcttagtg tcagattttg tcccacactt accttttagc tctttcctgg atttcagctc 22560
actgccattg tttctttgct tggagagttt gtttgccatt gctgcaagcc cagctgcgca 22620
ttaaaaaaca tgttgtatcc agaatgtagt agaattatag caggaggcct tcaaaggatc 22680
agttttgtca gaatagtgag aatggatggt gtgtgttcgt aatgttcaag gcatatgaac 22740
acaactgcaa gaattagaca ggcacaagta ggtgtagccc acacttcaaa attttagaaa 22800
caataagaca tagacatagg aaagaactag agcacatttc aaagctctat ctctctttct 22860
ctgtctgcat ctgtctatct atgtctatat ctacagctgt atcatctaaa tgtcctcaca 22920

-continued

```
tgtaatacaa aggtagagat gggtgaagaa ctgataccca gagtaagtgt aggatttcct  22980
ttaagggcct gaagctggta ctcagggtgg aggaaacagc atgaacagag gcactaggag  23040
ggaataagta tgggatcatc tctgtgtctc tgtttataac aagggccttg cctcactgtt  23100
atccttctgg cttcataatt gcagaattta gctagtaatt ttgtatacaa atatcccttt  23160
tgagagtccc ctataatttc cttatttaca atatggatgc ccattaaagt cctcatagtc  23220
ttatcaggtg gcttttacat gtggacaatg taaggactgt attatttact cctttgatga  23280
tcatggtagc tagggtgctg aaatcaatca agcaacagca tctcagagag atgcaccttg  23340
tttcctactt ttgcatgcaa agttgctgtt ttttcctttc attgtccact tattgaggtg  23400
gggtttgaga gttctggttt ctgtctttta acactaaaat caccgctgac ttgtccatca  23460
agtcagcaaa gtctttcctt ggtacagcaa agtctgtctg gctcaacctc catctgggcc  23520
tgtggcattc tactgaactt tgtagttttc tctattcttc aaaacaaaac tatctgaaac  23580
agggtctact tctgggttgt aaattagttg tagaaaatct gggctctgaa caaaaaccac  23640
atttgaaagc acatgtcttc tcttttattg gcttttgctc taaaaagcaa aggctgaaaa  23700
acagctgtta gctgtttata gagtattttt tatttaagtg ttagacaata gctgttttct  23760
tctccactta caatggcaca ttttttctca ggccagttaa gtcctctctc ggtgtggccc  23820
tgggtatttg tatgcacctc ctccctttcc ctaggtttct caggagacta agggttgttg  23880
ttttttttctt cctttcttca gtttctggtt tttggttttg aattcagact ttggtctctc  23940
agaatagatg gctgaattta gtcccaggcc agaatccttc tgggccaact ctacacaggt  24000
attcacagaa gacactctag aggaagcttc tataggtgca aagtgttgat ggtttgtggc  24060
tagatggcat gggcagaatt agatatagac gtagttattg ctctctattc tcgagccctg  24120
aacatcgttg gtttgctttc ctctattagg aattcagaag atagtgcttt ccaatcccct  24180
catcctggaa cgtgctctga ggacactgcc attgctcatt atcctcatgg tcccaagcaa  24240
gcaagatcag cagggctcag ggacatattg cacatgagtg aaaacactcc ctagcctgca  24300
aaaggaacca gccaaaatgt ttttcagcac tcttgtgctg tgtgctgcca tagcaattcc  24360
tactatataa gacaatggta acaccatcaa gttacatgtt ataccaggtt ttcctgggat  24420
tttatttgcc tgcagtctgc ctccttttaa tcaatttctg ttctttcaga tcatcaactt  24480
gtattgattt acatatgggg gaatagtcta acctgtgatt tctggaaaag acagcttctt  24540
atacctcact aagaagacac aggggctggt tatatctccc tgagatctta gacattcaaa  24600
tcctgcctaa cgaacatgag ccccttcatt tacccatcca tcacaccatg ggctgggcca  24660
cctctaaacc agtttctagg acttgggaat tttttttgtt tttttagaca aggactcact  24720
ctgccatcca ggctgaagtg cagtgtcaca atcacagctc acagctcact gcagcctcta  24780
gctccccagg ctcaggtgac cctcccacat cagcttccca agtagctcag gtgacaggaa  24840
tgcaccacca cacccaggta atttttgtat ttttagtaga gatggggttt cgccatgttg  24900
cccaagcttg tctcaaactc ctgggttcaa gcgatcctcc cacctcagcc tccaaaagtg  24960
ctgggattac aggcgtgagc caccacacct gatgaacttg ggaattctta caaggtgaca  25020
ccagggaagc actgcaagct tgttagaaac tgcctttgca aaacttataa tggtgagaaa  25080
attatgacag tgaaagagat ctgacctgac caacttcgtc ttgcctttaa cctccaaact  25140
gccctggtca ttcctgggca tgggccaagc taactttggg agaattttag tttatagttt  25200
aaatgataat aactcttccc aaaatgaaac tgcctttata aaactaataa aagttcacaa  25260
gtttaggatt atgagaggga tttgaattct gctaagatgt aggcataaag gattatcagc  25320
```

-continued

```
catcattcca gaggtcacca gatttgtaac ttccccaatt actcctataa ataacctcac  25380
tattgtagcc cttttgagat gtttttccag acttttgtat ttctgatgac tggatgactc  25440
cacctggacc cgagactcat gactcaccca gtcctgtggc cccacccaga agtggactca  25500
gagcaagagg accattttcc acaccccaat gagtgcatcc ccaaccaatc agcagcacct  25560
gttccctagc cccctgacca ccaaactctc cttgagaaac cgtagcctcc aaattttctg  25620
ggaggctgat ttgagtaata ataaaacttt ggtctcctat gtagctggct ctatgtgtat  25680
taaactcttc ctctattgca attcccctgc cttggtaagt cggctttatc tgggcagtgg  25740
gcaagaagaa ttcactgggt gttacatgtt gaaataaata tatacctgga taacagacaa  25800
gctttgtacc cttcacagag actctaggaa tttgcaaatc tatagtgaca atgccacctc  25860
caatccccca acaaccctcc ccaaagtact cctccgtctt attctgcatc acacataact  25920
aaacacattt tgctcttatt taataaggga aaaacacatt gtgattgttg cttttagaat  25980
agttggtcca aattagataa ttagaaaaat agttcccata gatgtaactc aaaacagtag  26040
gtttgtatga cactatttca aaaacaagtt ttgtggttaa aataatacct ccctttggga  26100
gataagagtt ttggcatatt aaaggctcca agaagtcctg tgacaaagac attttgtgga  26160
actctgtttt cacaggacat ctattaacct ctctcagtac agtcatgagg aaaacatgtc  26220
ctgaaatctg tcttgaagtt caaattttca gcatcctcag gcatattcac ccaccgggaa  26280
tcctggtttc agctgcccca tcctgctgct gccctctctc cactgatcct caccgactcc  26340
ctttgtttat gggacagggc tcaataatgg ggaagatcag ggtcccacac actttctcag  26400
agcttaaact aagaggggag gggagctgac ggtggaggga aaagctgcct cttctccatg  26460
attgtcctca cccaccctct tgcctacagg gggctgcttc tcttgtgtgg cacatttgct  26520
ttcactatta ataactgtat agttattttg ccatcctatt ctagttgtgg accagttgga  26580
gcggggcata gacataatgc gtgaagaagg atgctgaccc acagctattc ttccagaaaa  26640
aggcaggcac ccccaaagta caaggggaag ggcacttccc cttagccagg tggaggctgg  26700
catggaacat aaagtcttag ttgaaatgga tatggcaacc acaaggaaac atgtgacttt  26760
gcaaagagag acagatggac agtgactcag acaactgtac cataccagaa gcacaccagc  26820
ttcctgagca cagaaacatc catctccagc ccagcgatag aaatgtttgt aaaacagtgt  26880
aacaagattc tgcccagttt cccactaggt gtccggggaa atgggtggct ggaggataaa  26940
gaggaggagg aggaggaaac aggcgcgttc tggccagtaa ttctctcaaa cgggatgagt  27000
attgttgcca gcaggacttc tcaaaggaag gtatcttagt tcaggctgtc ataacaaaat  27060
gccatagact agggggctta caaacaacag aaatttattt ctcacagttc tggaggctgg  27120
tacccccaag atcaaggtgc cagctggttc ggtgtgtggt tagggccttg atcctcatag  27180
atggccaaat tctcactgta acctcacaag gcggaagggg tgaggggtct cttggggcct  27240
gttttatggg gacactaatc ccattcatga gggcttttta cgacctaaca acctcccaac  27300
ggctctgcct cttaataccg tcattttgag ggttaggatt tcaatatacg aatttgaggg  27360
ggacacaaat attcaggtca tagcagagag tgacttccat ttgtcaatga aaccagactg  27420
tgtacgtatc actcttgcca tccataccat ggtttgcatg tgatgttggg caacaggttt  27480
atttggctac attcatgccc acatccacta gacatgcaca ctcttcccaa ggagagggaa  27540
aaaaaagcta gaaactggtt atgtaacaat cattagtttt atagctgagt aagttatgaa  27600
taatagtgct ttcagcgatt tcattaccaa tctgccccca ggagcaagat gaagctgata  27660
```

-continued

```
aaatatttat gggctagtaa atttttttcta ctaatttgca aggctataat aaaatccatg  27720
aacttgatgg cctgcaggaa acataacaag aactaggaat gtagagtaat ttggagctag  27780
aaagcctctt aaggccctac aggaaatgac tcccagaaag cagatgaatc acagtatttt  27840
aaacagaaaa taatgatgtt atgtttgtac ttaaccagtt atagcctgag aacaattttc  27900
cacaaggaaa ttgtggaaat ttcctgctct ccattatttt tgccttaaga aataaaatta  27960
attcaagtat ataaaaaaca atattcaaat aaaaacaatt actggaacac agtgtatcct  28020
gtaatgaata tgaactttta ggattgtaat tgttaagaaa ctacagtata cacagtcaca  28080
ttgtgccctc ttgtggcaga aatattgttg tgctccgagg acacgccctg gtgtatttta  28140
ttcagtaatt aatcaggttt gtttggggga agtcagttca agtgaaaaga tggtttgcag  28200
aaggtagttg gcaaagagtt gtttctgggg cactctagag ggtgcacacc tggaaggggc  28260
cgttcttagc caggggagca gctgtcaaaa ggtttcctga tgttttaaca catgctaaga  28320
aatacccatc acagaatgct gcttcaattg tctgtctaat gttacacttg ctcatttaaa  28380
atattttatt actagttatc ctcatctata aataacagta attgctatta tttagtgaaa  28440
caggcagttg atgcacagta tctcatttaa tctcaaaact ataaggtaat ataaggaaac  28500
tgaagatcgc agatattaac taatgctgta gtttacctaa ctagtaaatg gaagagctgg  28560
gatttgattt aacttcccat gtttccataa gcctatgcac tttccattct gccaagctga  28620
ctctctagac aaatatttcc tgaatactga atacatgtga gactctgttg ctgggtcccc  28680
tggaattgac aaggtgtaag taatatactc ctatccttca ggaacttatg gcgtaaatag  28740
ggaaataaaa acatacacgc aaaagaaact gccatacgag gcagcataca aggaatatcc  28800
atgtagaact tttttttttt tttttttttt gagacggagt ctcgctctgt tgcccaggct  28860
ggagtgcagt ggagcgatct tggctcactg caaggtccgc ctcccggatt cacgccattc  28920
tcctgcctca gcctaccgag tagctgggac tacaggggcc cgccaccacg cccagctagt  28980
tttttgtatt tttaagtaga gatggggttt caccatgtta gccaggatgg tctcgatctc  29040
ctgacctcgt gatccacccg tctcggcctc ccaaagtgct gggattacag gcatgagcca  29100
ccgcgcccgg ccatgtagaa ctatttttta aacaaataca caaaagatct gtatagtcat  29160
gtacacttct ccccttcaga gcagtagagc tatatacttt ctgcagttac tctcctattg  29220
cttttggatt tgagtgtgag caggacttgt ggcttgcttc taagccatag aatacggcaa  29280
agctgttggg atgtgtgtga ttatgtgtga atacatgatt atgttacata agatattagt  29340
acccatcttg ctggggtctc tttctctctg gctttgagga agcaagtgat tacgttgggg  29400
aacacgtggc aaagaactgt gtgggtggtg tctaggagct gagggcagta tattgaagtc  29460
cttagtccca aaactatgag aaactgaatt ctgccaataa gtgcctctag ttgagcagta  29520
acattgttac tcaacaatag ataactagta catttatctt ttaaagtttt ataattttaa  29580
atcttgcatt taggtctttg atctatttca agttgctttt tgcttttttt tttttttttt  29640
gagacagagt gttgctctgt cactcaggct ggagtgcagt ggcaggatct cagctcactg  29700
caacttgcaa ctctggggtt gaagtgattg ttgtgccttg gcctcctgag tagctgggat  29760
tacaggcatg caccacccat gtccagctaa gttttgtatt tttaatagag atgtggtttc  29820
accatgttgg ccaggctggt ctccaactcc tggactcaag caatctgccc accttgggct  29880
tccaaaattc tgggattaca ggcatgagcc accatgcctg gcctcatttc aagttaattt  29940
ttatagatgg tgcaagtttc ccactgtcag gtacaggctg acattctctt tttttttttt  30000
tttttttttg actttttttct ctttttggca tatgggtatc caattgttcc aataaccaat  30060
```

-continued

```
gttgcaaata tatcttttgt ccactgaatt gccttggcat ctgtattagt ctgttttcac  30120
gctgctaata aagacatacc cgagactggg aagaaaaata ggtttagtgg actcacagtt  30180
ccatgtggct ggggaggcct cacagtcatg gtggaagttg aaaggcactt cttacatggt  30240
ggtggaaaga gagaacgaga gaagcgaaag cggaagcccc ttataaaacc atgagatctc  30300
atgagactta ttcactacca cggaaacatt acgggggtaa ctacccgcat gattcaattc  30360
tctcccaccg ggtctctccc acaacatgtg ggaatttatg ggagtataat tcaagatgag  30420
atttgggtgg ggacacagag acaaaccata tcaaagtctt tgtcaaaaga caattggcca  30480
tatatatgtc tatttcactg caacctgcac ctccggggtt gaagtgattc ttgtgcctca  30540
gcctcctgag tagctgggat tacaggcacg caccaccatg tccagctaat ttttgtattt  30600
ttagtagaga tgtggtttca ccatgttggc cagcctggtc tccaactcct ggacccaagc  30660
agtccaccca ccttgggctt ccaaagtgct gggattacag gcatgagcca ctgtgtctgg  30720
cctcatgttt ctaggctctc tgctcagctg atctatgtat ctgcctttat gccagtgcac  30780
actgttttac ttattgtagc tttttaataa ttcccgaaat cagatagaat aagtcttcca  30840
acttcatctg ttcttttttc accaaagata tttggctatt ctagatgctt aacattttca  30900
taaaatatta gaatgcaagt tcattgccac gccagagcat ccccttttct gccctgttgt  30960
cccaggccaa gagccatagc ctctttgctt tagtttcctc aaccctggat aacctgtccc  31020
gtggctcaca atttcagggg acatgtgtca agctctctga gaggtttcct tgaagctcct  31080
cttcagactt atggtgagaa agtgtcatca cccctcacag ggtagcagca gctctcacca  31140
ggaactcttc ccgtaagccc actcccagtg gagttccaag gggagagcca cgagactgtt  31200
ttgtgccttc tatgtggcct gtattcttgg ccacttgcat tgaatgtctt catcttggtc  31260
tgtctcaaaa tttgctttgt gtccaatatt tatcacgtct tggtgtttca ctcaacactt  31320
ccaattcaat gttttgttac tcatctaaat ttaaatgtta cacgtttaga taatttcatc  31380
tagaattttt agttgtttta tagaggaagg gatgttcagg gagttgagtt tgcaatagtc  31440
ccagaaacgg aagtttgcaa ttatttgctt acccattatt gctgctattt tcttcctgtt  31500
accattatag ttatcgatca atcatatgga atgtacaaat tgtttctctg tagtgcaatc  31560
ttgtcacaga acacagaact atcctttttg gggaggcaga agaaatagag taatactttg  31620
ccttttgaat atattgggaa gaagaaaagt gctcagatct cagtaaaatc tgaacatttc  31680
taggtccttt tcaatactta gatgtagctc ttgtgagtac taagtactaa acctcccagc  31740
tggggaatgt tacatagcag catttaaatg ggagatgaac aatcttaacc acatgctggt  31800
tccgaggcac tttcctgcag aatgactata taaatccagg tgagtgcttg taaaacacac  31860
aattacaccc ccacagagtg gactgaaagc acgtagtcag gcaatgagca cagttaataa  31920
tatggctata aaagaaatac aggatctcct tcactttttt ttttaaagga aaaggccaat  31980
atttatgctt gaatgtcttt atagtttgag acacattttt tattaaaata aattaataca  32040
taattgatga tgtgtatata catatgtacc tttgtttggg gtcgatattt tttataacct  32100
tgtagtttaa acccagggga aaattttttta aactggtaat ttacttgagt tttaaaaacc  32160
tgatgatgag ggtaataatt aaaatagtag caatagcaat gtagtatatg ataaaggcag  32220
catttgaatc aatggagaaa aaatgggtta gtgtcactcc acagtcttgg gacaattggc  32280
aattatttgg aagaatgtaa tctatgtatc cttacctttt tctttctttc tttcttttt  32340
tagtcggatc tcactctgtt acccaggctg gggtgaagtg gcacaatcat agttcactgc  32400
```

-continued

```
agccttgacc tcctgggctc aagtgatcct cccgcctcag tctcccaaag tgctggaatt  32460
acaggtgtga gccactgctc cttgtgatct tactctttct accaataaaa attccagatt  32520
gtattagtct gttctcacac tgctataaag aactacttga gattgggtaa cttataaaga  32580
aaataggttt aattgactca tagttctgca ggctcaacag gaagtatgac tagaaggcct  32640
caggaaactt acaatcatgg cagaaggtca agggaagtat gcacacattt acaatggcag  32700
agcaggagac agagagcaaa gggggagatg ccacacactt ttgaacaacc ggatctcatg  32760
agagctcact cactagcatg agaacagtaa gggggaagtc tgccccatga tttaatcacc  32820
tcccactggg cccctcctct gacacgtggg gataacaatt caagatgagt tttgggcagg  32880
gacacagaac caaaccatat cacagatgaa gttttatatg taaaacacaa agaaacacaa  32940
acctaaaagc aacagaataa acccatatat atgtatgtgt acatatgtgc atgtgcacac  33000
atacatatat tcatgtactc atgtaaaaat tttgtagcac ccaagggtgt aaagtaaaaa  33060
ataaatgtcc ccttcttcac ccaaccttca tgttctattc ccagggagaa aacaagttat  33120
cagattcttg catgtccttc cagagatatt ctgtatatat ttaagcatat atgtgtatac  33180
ttttattaaa agacattcta ttggatagac aagattattc tattcacttt tttggcaaaa  33240
tattaatata ttgaacatct ttccacttag tacatattgt tctatcaact cattgttaat  33300
gattgcctag tatctcactg tatagaggca tcatatttat ttaaacactt tcctaaattg  33360
cgtttctcat atggcaatgt ttcatggtct tcccatatag cccatatgga tctcattatg  33420
ggagatacct ctaccttatt ttgtcctatt gcatactatt ccactctagg aatataccac  33480
aacgtattag tccattgaca ggttgtttcc aacttttctc tattacaaac aatagtttct  33540
agtacatgtc ctcttatgaa aatttcccta agacagcagt tctcatacag tcaaaggatc  33600
accttggcta tggtgttgag aatagccatg gcatcgggga tcaagaacaa aatcagtgac  33660
agtggcaggc cattgcaaat agtccagata agtgactaag tggcttgtac tagacagtgg  33720
tggcaaggat ggtggtgaca agtggttgga atggggcaca ttttggaggt aaggtaacat  33780
gatttcttga cccttaggtg tagagtgtga gcagaaaaga gacatcaatg aagattccaa  33840
agtttggggc ctaaacaacc aagaaaataa agttaccaat taccaagata cgggacactg  33900
ggagacgagc agctttgggg acaggatcca tgtcacaaaa tctgttttgg acatattaag  33960
gttgccaatc agacttccca gtgagatgtc aagaaactaa gaaagaagga aaagatccag  34020
gaacaggcac tgagaaaaag cagccagtga gacaggagga aaccaaggaa gcatagagtc  34080
ctggtttcca gggaaaggaa gtgatctaat ttcttaaatg ctgctgacag gtaaaataag  34140
agaagatgta caaagcacta caggaatcgg caaagtggag ttcaccgatg tggacaaaag  34200
cctgactggt gtaggttcaa gggaacatgg gagaagaaga attagagaca gtcattagaa  34260
ttacaactct ttggagagtt ttgctttaaa agggaacagg aggccgggcg cgatgactca  34320
cgcctgtaat cccagcactt tgggaggccg aggcgggcgg atcacgaagt caggagttcg  34380
agaccagcct gaccaatatg gtgaaacccc ttctctacta aaaatacaaa aattagccat  34440
gcgtggtggc gcgtgcctgt agtcccagct acttgggagg ctgaggcagg agaatcactt  34500
gaacctggaa ggcggaggtt gcagtgagct gagatagtgc cactgcactc cagcctgggc  34560
aacagaacga gattctgtct caaaaaaaaa aaaaaagggg gaacaggaaa aaagggacag  34620
tggcttgaag ggatgtatgt ggaatcaagt gaggatgcta agatcacacc attcttgtag  34680
gatgttggga gattccaagt cgagaggagg aaaatgcagg gaagaaaggc actaaggatt  34740
caactgagga ttgatgtcct tgagtatgtg agagaagcta gggatccagc gcacaggttg  34800
```

-continued

```
tagggctggc cttaggtagg agcacaagag tttgtccttc atagcaatgg gaaaacaaaa  34860
tacatgagca taaacgcagg agaggggtta aatgtagagc tgggaacgtg tagaagttct  34920
gtactgtttc tattttcatg gcgcaatagg aagttaggat cagctgagac cgactggcta  34980
ggtgatgaaa ggcggtcacg taaggggtga atgttaagtt ttgcctatga cgaaggacag  35040
atggtcacgg ttgtgccata gaagaacctg aattggcaag tgaagaccgt catgtcccct  35100
ggcaaggcaa gctggtaagc tgtcctagca aaccaaaaac caatgaagca taaggccagc  35160
tgggcggtgc ggtgccgggg agggcccctt tactgaacaa ctcccttaaa caccggctga  35220
gagccggcac taggctagga tggtgaggtg tgattgcggg tgagacaggc cacccccttct  35280
tcgactgggt aatctatgga gatatatttt tctgtaagaa taaatctgat ttttataatc  35340
gaaataactg gggggaaaaa gatgatatcc tcaggtatct ggtgagagca ggtagaagag  35400
agaagggagg ttgggagaac tgaagaatga atttgcagga aaatgggagg cacaattttt  35460
acagcttggg acacacatgc gctctcctcg ttaggatcaa ctctcctttt tacttgagtt  35520
atgcagagct agctgccaca cactgtgcta ccaggtgcct gggtggactt tgacaagtcc  35580
ctttatgtgc aaagcacgtc ctggaagagg tgctttctga ggccccagcc cacagcccag  35640
tgattctgcc acgggaccta tttttcctga gcaataatgg gagaagttgg tttttaaaat  35700
agacataaag aaaatccatc ccaaatatta accgttttta taaacctctt aagtcattct  35760
gtccctttcc tcttttatgt ttccaagtaa atccaagaag gtcatcatta aataagcccc  35820
aattataaaa gacatgctaa gacttagtgt gcttggccgc ctctgctctt tagccggcag  35880
taataaaaca atgaacccca gcaggactcc gttccaaatc atattctgca gttattgttc  35940
tgactccttt ctttcattat tgcaaacaga atcccactga gctcacacac tttcaaaacg  36000
actgtttccc cacactgcag aaagtggggc ggcatttttct aagagccgct attgttttcc  36060
catggcacat ttatatctca aaggtacatt acctaatgct tactgcacgt tatgattttc  36120
atttgcttct tataaatgcc cttccttaat gaatttttag aaagtacagt tttttgtcaa  36180
acgtttttct atcttttttt ttttttggat atttgattat ttctttattc cactggacac  36240
aaagcagtac ttggcaatca ttaattctag gcaaccacat caaagaagct gtattagcac  36300
tttctattaa ggtctcatta ctaaatagtt ggtaaaggca ataataatgt tttgttttct  36360
tgttctggcc ttacaaatat tcttattttc ccatgtattc ttgtatagtt caatgatatt  36420
taatcacaca gtgctaaaaa ttaagtgatt ctaagttttt tctgctgttg gaagaaattg  36480
gtatgtgatt gagcaaatca ttctgtattt tgtaagctgg gataaatctt gaagtgcttt  36540
tcttcatgat tgtaggtcta tctatcctta aagcttagta tgaattcttc gtatatctgt  36600
gcatgaataa ataactcaaa gtagttcaaa taacaaagaa acatattggt ttctataaca  36660
gaaaattcac aggtagttga actcagataa ggtctgatcc agaaaacaat gttatgtagg  36720
ataaaaatgt tataatgtta tatagaggac caggacattc attaatacaa atattaggct  36780
agtttttgag attgtgtgat ttttaaatac tatttgtcag catttgtttt ttttttttgc  36840
tgcaggtggg cgtgtgtcca catgtgtgca tctgaattgg tttgcaggtt ctgtgtgcct  36900
ctaccttcat gttgtgttct tttttaaaat tttaacatta tgtatatttt ttaaattaat  36960
taattttttt tctgagacag ggtctcactc tgttgcccag gctggaatgc agtggcacca  37020
tcaaagctca ctggggcctt aatctccctg ggctcaggca atcctcccac ctcagcctcc  37080
tgagtagctg ggaccacaag cgcatgccaa tatgcccagc tcatatttgt atgtatcgta  37140
```

-continued

```
gacatggggt tttgccatgt tggccaggct ggtctcaaac tcctgggctc aagagatttg  37200
cccacctcgg cttcccaaag tgctgggatt acaggcatta gtgatgctcc tggccctatt  37260
aatttttaa attgacaaat gataactgca tgtatttatt gtgtacatgt agttttgaaa  37320
tatgtaccta tggctgggcg tggtggctca cgtctgtaat cccagcactt tgggaggctg  37380
aggcaggcag attgcgtaag cgcaggagtt cgagaccgca ctggacagca tggtgaaacc  37440
ccgtctctac taaaatacaa aaaattagct gggtgtggtg gcacaggcct gtagtcccag  37500
ctacttggga ggctaaggca agagaatcgt ttgagtcctg gaggcggagt ttgcagtgag  37560
ccgagatcgc accactgcac tccagcctgg gctacagagt gagactccgt ctaaaaaaaa  37620
aaaagaaaaa gaaaaaaaga aatacgcgca tattgtggaa tggctgaatt gagctaatta  37680
acatatgcat tacttcacat atgtatttgt cagcttttta aaatgtgcaa aatattgtga  37740
tttcttttct tattctaaat aactttgtat ttataatttt taattttcta aaatggttcc  37800
cccaagttgt ataaacttta agtctcacaa aacctggatc tgtctctgct gagcaaaggg  37860
tgaggttgct cccagaggaa agattttgtg cacacgcagg agaaaggaca cctaatggca  37920
aaaacagggc atgaccagta aagttttaaa ccttttctga actttctttg ctttgaattc  37980
tgcctctatg aggctgataa attttttaat tggcaatgaa gctattttaa ggcagggatt  38040
atgtgttaaa cctctctggt tgtgcaccca gtaatcagcg aactaacttg tatggaagaa  38100
catattgata tattaacact tctttccagt acagtgattc aaagtgatta tacagtcgtc  38160
ccttggtata cacaagggat tggttccagg acctctccgc ctcacccacc ccctcaccta  38220
tataccaaat ccatgcatgc tcaaggcaag tcccacagtc agccatgtcg aacctgcaca  38280
taggagaact cagctgtctg tacaggtggg tttcatatcc ctcaagtact gtattttcaa  38340
tccacgtttg gttgaaaaaa atccacgtat aggtggatct gtgctgttca gacctgtgtt  38400
gttcaagggt cgactgtact ttttttact tgaacacata aaattttcat ggaggagtcc  38460
aaattccata aaggagttac atcataaact caaaaggctg tatagagaaa gattattaca  38520
acaatagcaa aacatgtttg cagaacaaaa caatgactca agtcttggac gtggacccac  38580
taatttcaaa taattatcta ttggctgcgt ctctagtatt tgttgaacag aactgcagct  38640
acagtaagaa atcttgcctg atgaaagatt atgattaatt taagaattgc taaatgtaac  38700
tcagtgtttt ctaacatcct tgaggagcat atatttgttt taaaggttaa tctggaaaat  38760
gagttttagg aaacgttaat gtgcatttac ttgggaggta aatagttaaa ttagactctt  38820
ccccttggcc tttccaggag gtttgggttt catgttaggt tttgctgtaa attgaaattc  38880
atttgcagtg agaaagcgtg ttgagaatgg attttgggat tttgtcaggt ttgtccagag  38940
actgttgtca ttggtctgga gagggaagga tcttactccc gtagaatctt tgtcttcttc  39000
cagaatgtcc tcatttggca gtactgggtg acacattggt acattattaa gtaactgtag  39060
tttgacctct tggagtttgt tgggaacaaa tccaaataaa ctggcatcta ccttctgttt  39120
gccttgttcg tgctttgctg tttgtcaaat cacctctctc agcagagtgt cctcttttt  39180
tttttttttt tagcagtgtc ccctggtaaa aaccaggggg ttgtttcaga atgaatctga  39240
ggtccagtta actgcaacat tctcttattc taggattctg ttttcaggaa cacagatact  39300
ttcagacaaa tgttaaaagg cttggttaac atgggaaata gttcctcaaa acttagaggt  39360
taaagtactg tactgttaaa gaagttaaag tactgatttt aaacttttct agaaatttct  39420
gggaacaagt agtgtttttc aagatttctt agagggaaga gacctttctt ccctaccagc  39480
agtctgtcca tcctttcaga caatcatttt ggattaagga tatttaagta agtggttagt  39540
```

-continued

```
gtgcttcaga atacctgggg tttattaaac acaggtgtat gcattgtcat atattgtgaa  39600
catctttcca tgttaataaa tatgcaacta ggccaccatt tttactttaa ttttaaaatt  39660
atatattatt ggccaagcgc agtggctcac acccatcatg tcagcatttt gggaggccga  39720
ggctggtgga tcacttgagg ccaagagttc acggccagcc tggccaacat ggtgaaactc  39780
tgtctctact aaaaatacaa aaattagcca gctgtggtgg tgcacgcctg tagttccagc  39840
tactcaggag gctgaggcgt gagaattgct tgaacctggg aggcagaggc ttcagtgagc  39900
caagactgca tcactgtact cctgtctggg caacaaagac tctgtctcaa aaaaaaaaaa  39960
aaagaaaaaa tatacattat ttattacaga agtaataaca tcctagtata aaaacctcag  40020
acgattcagg gctgtatatt cccctatgcc aaaatatact tttcaatagc tgcatagtac  40080
tttcttatat agaaaacacc ataatttact taaccagtcc cctgtgaaca tttggccctt  40140
aagttgcttc ctttttgctt ttcttataaa taatactata ctgaaaatgc tgcacataga  40200
caattgcaca tttctctgat tatttcctca ttttaatacc cttgtgatta taggggtaat  40260
atactgtata cagtatttat tatagaaaat acaaaaataa taaaaatact tttatctgag  40320
gcaattagga ccagtagata gtcgattaac tgaaaaagtt ggtaaagcaa agaatcataa  40380
aaaaagaaat tttatgaaag acccagatga cttcaaagct atttgaattg tttcagagca  40440
taaaaagaga aaatacccaa gttattttat aggaagccaa cgtaacattg aaaacagtgt  40500
gcaacaatgt ttgcacagga aaattctaga caatctcatt tattaatatc agtacaacaa  40560
tctaacataa aatattagca accagacttc aacagcacgt caaaggataa taaaattaac  40620
aattagagtt tattacagga atgcaatgac cattcttttt tttttttttt ttttgagata  40680
gagtctcact cttgttgcct aggctggtgt gcgatggcac aatctcggct cactgcaccc  40740
tctgcctcct gggttcaagc gattctcctg cctcagcctc ctgagtagct gaggttacag  40800
gcacccacta ccacgcctgg ctaatttttt gtatttttag tagagatggg ggtttcacta  40860
tgttggctag gctggtctca aactcctgac ctcatgatcc gcccgcctca acctcccaaa  40920
gtgctgggat tacagatgtg agccactgtg tctagccaat gaccattctt tattttgaac  40980
tcttttatta cgacatgaga aaattaatat tatcttttca gcaggtacta agaaggcatt  41040
tgatacaatc cagtattcat tcctggtgaa aacttcgtaa accagcagta ggtggatact  41100
ttcggcatga gtaaatatat ctatcttagt ctaaaaccta gcattgagca taatggagaa  41160
tggaggaaca ccatatgttt ccattaaagt cagaaacaag gcaaaggtgt ccaggcacac  41220
tgcaattatt taacattatt ctgcagatac tagctaattc aattagataa aagaaactag  41280
gcatcaatta aaaaaagagg aagtggccag gcgtggtgat tcatgcctgt aatcttagca  41340
ctagttgagg tggatggatc acttgagccc aggagttcaa gaccagcttg agcaacatgg  41400
caaaacccat ctctactaaa cataagaaaa ccgagatggg aagatcacct gagcccgggg  41460
agattgaggc tacagtgagc catgatgctg ccaccgcact ccagagagac accatctcaa  41520
aaaaaaaaag tcacataacc atcatttgca gatgatatca tgatatatct ggaaaactta  41580
aaaagagtca tctgaaaaat tatgtcaaac aatatgggaa gtaatttggc ttggtaaaaa  41640
taaataaata cagagaaata gtcttttact ttttgacaga gtctcactct gtcacccagg  41700
ctggagtgca gtggtgtgat cttggctcac tgcaacctct gcctcccagg ttcaagcgat  41760
tcttatgcct caacttccca agtagctggg attacagaca tgtgccacca cacctggcta  41820
atttttgtac ttttagtaga gattaggttt caccatgttg gccaggctgg tctcaaactc  41880
```

-continued

```
ccggcctcaa gtgatttgcc cgccttggcc tcacaaaatg ctgggattac aggtgtgaac  41940
caccacacct ggcccagaaa tagcctttta aatacaaaaa caataatcag tgagtagatg  42000
gaatagagga tcctacttac attgtagctg aaaaagtaga ttaagcttaa gagaaatata  42060
gaagttccag ttcaaaaaca tttaaaccct actgagaaat acaggagaga atgtgaacaa  42120
ttggaaggtt ctgcttttga gtagaaagac tcatcataat catgtcaact gtctttattt  42180
taatgcaatc tcagtaaaaa ctctgtaagg agtttttttt tttttttga gaccaattaa  42240
ggtgcctctc aagtattaaa gcatattatt atataaaacc agaataattt atgtagcaca  42300
gtgctgacat attataggca gcttgacaga acagggtata aaatcctgaa atgcatatca  42360
gacatcgttt atgatatata ctgttgtttt gcaatatgat aacggtgcat ttcaaataca  42420
gaaggaaaaa gtggattact tagttaatgg aagtgagaaa aaccagatac tctctggaaa  42480
taagttgaat tcatatttta catcttatac caaaatacat ttcagatggg tccaatattt  42540
aaatacagga agtaaagaga agtagaagaa aatatggaat gttttcatca tgaaatgggg  42600
aagaaatttc tgagcataat atgaaaccca gaagaaaaga aaagaaaaat ttgatcaatt  42660
ggactatata ataataaaat aattcaatat gacaaaaaca accataagga aagtgaaaat  42720
tcaaacaaca gactgggggg aagtatacaa tttccatcat atataaaggt tttatattcc  42780
ttatataaaa aactcctaca aacagtgaac aataccaaca accaacagaa aaatgaaaaa  42840
aaaaaaaaag agatgtgaac tgtagaagaa aagcacaata gggtcttaag catatgtaaa  42900
gatgctcaat tacatacata agaaagtatg agaaaataca aactataaag tagtaacatt  42960
ttacatgcca atttggcaaa tctcaaaagt ttgctaacat gctgtgtagg tgaaagtgag  43020
agaaaaataa acagtattac aacatactga atggagtgta aattggcaca atgattatga  43080
agagtaattt tgcaatatcc atcaagatta tagatataaa tatactttca cccagcaatt  43140
cacttctggg aatttagcca acaatagctc tcacatgtgc aaatagcaca tattattatg  43200
gcaaaattat tcatggtagc tttatttgta attgtgaaag actggaaaca atccaaatgt  43260
tcaacaatag aagtttggtt acaatgtttt tggttactgt ttcttttttt aaataatgga  43320
aaaatattgt gcaactattc agaaagagaa atatagtggt ttgaactgtc ctctaagaga  43380
gtagagtgag ttgcagaacc atttgtgtaa aacaaagaag gaaataaata tattgatttt  43440
tttgcttatt tatgcataaa atatttctga aaggatatcc aaatacttta gttagctggg  43500
gctgccataa caaaatacca tagtctaagt ggtgtaaaca acaaaaattt atcttctcac  43560
agttctggtg gctggaagtc caaaatcagg gtgccagcat ggttgggttc tgttgagggg  43620
gagagagtat gaaagctctt cagtgtcttt tcttcttctt tcttcttgtt cttgttcttc  43680
ttgttcttgt tcttcttgtt cttgttcttc ttgttcttgt tcttgttctt cttcttcttc  43740
ttcttcttct tcttcttctt cttcttcttc ttcttcttct tcttcttctt cttctccttc  43800
tccttctcct tctccttctc cttctcctcc tcctcctcct cttattcttc ttcttttctg  43860
agatggagtc ttgctctgtc actcaggctg gagtgcagtg gcgcaatctt ggctcactgc  43920
aacctccgtc tcccgggttc aagcaattct cgttcctcag cctcctgagt aagctgggat  43980
tacaggcgtg tgccaccaca cccggctatt cttttggtat ttttattaga gaccaagttt  44040
caccatgttg gcccggctag tctggaactc ctgacttcag gtgatctgcc tgcctccgcc  44100
tcctaaagtg ctaggattac aggcgtgagc cactgcactc ggcccagtat cccttcttcc  44160
aaaggtacta atcccatcat gagggtctca ccctcatcag ctcatccaaa cctaattacc  44220
acccaaagcc ttcatctcca aacaccatca cactgtgaat tagggcttca acatattaat  44280
```

-continued ttgaggagga cacaattcag tccacagtac caagttattt gatcatagta gttgctgctg 44340
ggcccaggga agaaagcaag atgtaggaga atagaattgg aaaggtgatt tttcattgtt 44400
tgctctttgt acctctgtaa ttctctatct gatatcaacc gagtgtccaa caattcaatt 44460
caattctgac ccactgtgtc actgaccaca tgttcttgga ctctccatag aaagtaacat 44520
gaggctgaaa gagtttttcc agataagact tcattggagc ttatgcccag acaggaaggc 44580
agcatgagag agagagagag agagacactg gggtagatta tgcaggttga agggtagggt 44640
atgcaggtca gcattatctg cttaggatgg ttatcttgtg taatggacca cctggtggtc 44700
tggccagcag caacaaggct gtaatccatt gttcagcatt ccttcccagg tgggacactc 44760
cacaaccttg gtttgatgtg tagatttcct aagggcaatt cctagaattc tttaagtaaa 44820
aggcatagtt aaacattatg taggaggagc cacatcccat tcctattcta cctcatatat 44880
acttagggtt actgtcagat tccataagtt aaagagctca gccccacaaa accgcctcaa 44940
cttcagatgc tggtcttaag tcatgggcca ctcatacttt tttttttga gatggagtct 45000
ctctctgtcg cccaggctgg agtgcagtgg cacgatctca gctcactgca acctccgcct 45060
cccgggttca agcgatttgt ctgcctcaga ctctcgagta gctgggatta caagcatgca 45120
ccaccatgcc cagctaattt ttgcattttt agtagagaca gggtttcacc atattagcca 45180
ggctggtctt gaactcctga cctcatgatc cgcccatctc agcctcccaa agtgctggca 45240
tgagccactg cgcctggccc catacttctg actagctata gattggtgat tcccatgaat 45300
ccctcctcat tttgagtatt ttgctagaat gtcccccaga actcaagaaa tcattttact 45360
tatgtttacc agttttttat aaaggacaca agtgaacagc cagaggaaga ggtacagagg 45420
gtaggaccca gcagggtccc aagagcagag gcttctgtcc tgtggagttg gagccagcca 45480
ccctcccagc gtgggttgga tgtgttcacc agcccaggag ctctccaaac cctgttgtta 45540
aggggttttt atggagtttc ttacataggc atgattgatt aaatcactgg ccaatggtga 45600
tccgattcaa tttccagccc cttttccctt tctagaggtt ggagagtgaa ggttccaatc 45660
atctaatcaa gacttggtct ttcaggagaa gggcccctat cctcaagcta tccagaggtc 45720
ctccaggagt cactttatta gcataaactc aggtacagtt gaaaggggct tgttatgaac 45780
agtaaaagat gctccaattt tccctatcac agaggaaaac tccaagtgtt ttaggagctc 45840
tgtgtcatga accagggaca aagactcagt atatattttc tattatattt taccacagtg 45900
ttaaggaaaa ggggtcctga tctacaccca aagggagggt tcttgaatct catgaaagaa 45960
agaattcaag gtgaatccat acagtgaagt aaaagtaagt ttattaagaa agtaaaggaa 46020
taaaagaatg gctactccat aggcagaaca acccttgggg ctgctggttg cccattttta 46080
tggttatttc ttgattatat gataaacaag gaatgaatta ttcatgagtt ttccggggaa 46140
aggagtggca attcctggaa ctgagggttc ttccccattt tggaccatat agggcaactt 46200
cctcatgttg ctatggcatt tataaactgt tatggcacta gtgggagtgt cttttagctt 46260
gctaatacat tataattagt gtataatgag cagtgaggac aactagaggt cactttcatc 46320
accatcttgg ttttggtggg atgtagttgg ctttaccaca ttattttttc agcaaggtct 46380
ttatgacctg taccttgtgc agaccttcta tctcatcctg tgactaagaa tgactaacct 46440
cctgggaatg cagcccagta ggtctcagcc ttattttaac cagcctttat ttgagatgga 46500
gttgctctgg tttgaatgcc tctgacaaca gtaccttttg aattttgacc tatgtataca 46560
aacacacaca cacacacaca caaacacaga agtattaata ctgagtaata ctgagagttg 46620

-continued

```
gggggatgct cagaaagact gagttaccca agttcacata atttgccatg gtcagagatg  46680
gacctcaggt ttccttactt ctgtttgaag gttttttcca atatgctgtg attactttct  46740
catctctttg aagatgttta ctgctttcat gacttcagaa tgtctgagta ttctagtttt  46800
caatatctaa aggggaatcc tttagattta ggggcatggg ggccacttgt gggaggtcaa  46860
tgatatttcc tcacacatta atgcaatttt tctccaatat tcaatgcaag atatggtata  46920
tagagaggca accatgtata tcatgcaaat tgagaaagac ttggaaactg tcccatccaa  46980
aagtactcat ctattaatct gctcaaagaa atatgaaaga aaacttagaa gaaatcccac  47040
tactgtgtag tatctcttaa gtaaattgca aatatttcta ggagaagtgc tcttgaaatg  47100
ggagagttcc ctgaccaccc ttaaaggaca tgcaacaggg gtatggctca tgtgtttggt  47160
caccacacac tcaaacccct aacaggagtg ggagcacaca gcagggcagg cacaggagct  47220
ggggcgagtg ctttgaggct ccagccccat agcagcatct ggagtgggtg cctgtgactc  47280
ccaaaaccca agtgggcatg gcatgtgtta cagtgcactc ttttagcttt gatgtccaca  47340
gatggtgtaa gtgttaacca gctcagtgga tcctctgcct ttttgcaagg gcagagggcc  47400
agtgtgacag cttactgtat cccaagctcc tgtctaacat cccagaagaa tcaggtcaca  47460
catggacttg aagggtagtg aatgtggggg ttttatcggg tggtagaggt ggatctcagt  47520
gggatggatg gggagctaga agggagatgg tgtgggaaga tgatcttccc ttggagttta  47580
gatgctcttt ctcttctctg ccacatcatt ctgctgttct tctgctcttc tgttcatctt  47640
ctcatctcct tgtctgctca tctgcttctg gaacctgagg tctgtggttt atatgggtac  47700
aggatagggg ggtcaaaaga caacttttgg ggcatgaaaa caggaatgcc tgttcccatt  47760
tagggccatg agtatccagg cttgaggatg gggcctttgc tggggaacca ccctcttcta  47820
cccagtattt ctctgtctcc tgtccatatc actcttacac tgtcaacaac tattattaac  47880
tcctgaaaaa atgaatttat cagattccta cttgcaggtc agattctaac agcaggctcc  47940
tacagaaatg ggacaagtgg ttgatgaaga gtcaaattct gtaaaatatt ttaagagatt  48000
tattttgagc caactttgag tgaccatagc ctatgaagga gccctcagga ggtcctgaga  48060
acatgtgcct gagatgatta ggctgcagct tggttttata tattttaagg agacatgaga  48120
cttcaatcaa attcatttaa gaaatacatt ggaggccagg tgctgtggtt catgcctgta  48180
atcccagaac tttgggaggc tgaggtgggt ggattacctg aggtcaggag ttcgaggcca  48240
gcctggccaa atggtgaaac cctctctact aaaaatacaa aaattagctg ggtgtggtgg  48300
tgtgtgcctg taatcctggc tcctcaggct gaagcacaac aatcgcttga acccaggagg  48360
tggaggttgc agtgagccga gattgcgcca ctgcacactc cagcctgggc aacaacgtga  48420
gactctgtct caaaaaaaaa aaaaaaaaaa aaaaagaaat acattggttt ggtcctgaaa  48480
ggtaggacaa cttgaagcag gggtttccag cttataagta gattttaaaa ttttctggtt  48540
ggcagttggt tgagtttatc taaagacctg ggatcaatag aaaataatgt ttggattaag  48600
ataacaggtt gtggaggcca aatttcttat tggcagagga agcctgcagg tagtcggctt  48660
cagagagaat aggttgtaaa atgtttctta tgtgacttaa agtctgtgtt gatgttaatg  48720
ctggagaggt ataatgagcc atgtccaacc actacttccc atcatggcct gaaacaatct  48780
ctcagggtaa attttaaaag agccctggct gagtaggaag tccattcaag tggctggggg  48840
gtcttggaat tttttttttt ttttggttta caaagggata ataaattttg atttaaaaaa  48900
caaagcacct gaggggtggg ctcagtggct gatgcctata atttcagcat tttgggaggc  48960
caaggtggga ggatcacttg aggtcggcag tttgagacca gtctgtgcaa catagggaga  49020
```

-continued

```
ccttgtctct acacacacac acacacacac acacacacac acacacacac atgatctgag  49080
gatctttgtt tttttcttca aagacagggt cttactatgt tacccaggtt ggatttgaac  49140
ttctggactc aagggatctt cccatttcag ccttccaagt agataagact ataggcatgt  49200
gccaccacac gcattctctc ggttttgtca tctgtaaaac gagtgagctg gaccagtgtg  49260
tcctcagatt tccttccttc agagctctgt tctggctaaa tgatttttca aatcccttat  49320
ctcacttgca tcccatggaa aacctgggaa gggcaggaag gacaggggag actatttttc  49380
ttacttgtca gataaggaag ccaagattca agagttccat gatcaccagc tatcttaatc  49440
catttgagct gttatgacaa aatgccacag actgggtaac ttataaaaaa tcagaattta  49500
tttctcactg ttcttgaggc taggaattca aagatcaagg tggcagctga tgaggtctca  49560
gttcctctgc ttccaagaag gcaccttggg gcagtatcct acagagggga tgaatgctgt  49620
cccctcacat agtggaagag agaagaacaa aaaaggactg agtgctacat ggagcctcag  49680
ggctttaatc ccattcacaa aaaataatca cgtcttaaat gccacacctc tcaatactat  49740
cacaagaacc attacgtttc aacacatgaa ttttggagga gatcactcaa accatagcac  49800
caggcaagga gcctgtttag catgggcact taactccaag tttagtggcc tttccactgt  49860
ctcatacaca ttcattcgtc ttttgagtac aaggtattat gctgcgtgct ggggatgcaa  49920
aaccaaaaag ataagcctcc tgccctccag gggctgacag tggctggaga aaatgaatgc  49980
ttacagagcc tcatggtcag ctccctgctg gaaacagaga tggaggaagg aggacaaaca  50040
gtatcgggga cagagcaagt ttcctggaaa aggcccatca ctgaagctga acgaggaagg  50100
atgaataggt atttggtata aagaaaggga aggcctgtgc tctcaggaga caatatttca  50160
tccttaagtg ggatacttag ggtgccatgt cagttgtctg tggtagactg ggagacagaa  50220
acttttgggt agagggatct ttcaaccctt tttggttaag attgtttgtc actgctgaga  50280
ccagctcagt cagggagacc ctaacccagt ggcgctagaa gaattaaaga cacacacaca  50340
gaaatacaga ggtgtgaagt gggaaatcag gggtctcaca gccttcagag ctgaaagccc  50400
agaacagaga tttacccaca tatttattaa cagcaaacca gtcattagca ttgtttctat  50460
agatattaaa ttaactaaaa gtatccctta tgggaaacaa agggatgggc caaattaaaa  50520
taataggttg gactagttaa ctgcagcagg agcatgtcct taaggcacag atcgctcatg  50580
ctgttgtttg aggcttaaga ataccttttaa gtggtccgcc ctgggtgggc caggtgttcc  50640
ttgccgtcat tcccacaaac ccacaacctt ccagggtggg tgttagggcc attatgaaca  50700
tgttacagtg ctgcagatat tttgtttatg gccagttttg gggccagttt atggccagat  50760
tttgaggggc ctgctactaa catgtccccc ttctctgatg tgcaaatcaa taaactcaaa  50820
ggcagctttg tcacagtgag ctacttcttg caggagtcag gatccacatc tgcagactat  50880
acaaagacaa acaacacaga ttaaaagcac aatcatcatt gaaatcacag agcttccaag  50940
tgtttttatc aattttcagc tccttgaagc acaccagttc ctggcattaa ggtcaggtgt  51000
gcctgggatg ctttaaatat ttgttctttt aattttaaat ccttacgcta agctcctaga  51060
gtgggccata tcttttgagg ttgaggtgcc actatactgc catggttcca gataatagga  51120
actcttgcta tacttattat tatatctacc atctgaccgt tttgttcaga ccagctgaac  51180
atagtgtggc catggcacac agactgagag gtgcaatttg agctaaacat ccccttaggg  51240
gaccaactac taatgattcc ataggaatcg ttgtgcaaca cctctgcctg ttctgcaatg  51300
caatcttcct aaacaagtat gttcattttt tctaactggg tccaatcctg tttacaaata  51360
```

-continued ggtttttgag ggcagtatgc ctcaattata ggagcagatt gattatggta aatactgaga 51420
tcagaaagca tgtgtaactg tgtcataaag tgattgcatc caggcattat tgccagccaa 51480
gattgataaa tagacccagt aagtataatt gttctctgtg tcaccccttta ttgaaggaat 51540
actcatgaca gtggtgataa ccactatcat agctaccatt aaattattca ttgtgactgg 51600
ttgtcccgct ttcctcaagt tttcttccgc catctgtgac agcttcttga tctgtcccca 51660
ggtgggtgac tgtgttcaac gggagttact cattgacagt tggggtcctc ctcagcgtca 51720
gccttgacat ggctgcaact ggggggtcct tgggatcctc ccgaaatctc ttcctcagca 51780
tctggctcat gataaggttt tgagtgtctt gatggtatcc aaatttgctg ttgattttgg 51840
cctgtacccc aagttattat tttacctatt tcccaacttt ttgttatcag atctctccac 51900
caaatcagtt gttctgcttc tgtctttgca gctggtttct gtagatgctg ttcagttgct 51960
gatgacatct ggcctttggg caggctcaaa aaatttaaaa ttaataatgc taggttcagt 52020
tgcatctgtg ggggttccat attgtctgtc ttcccctttc tgcttttgca acttctgttt 52080
tagggagaga ttcattcttt ccactatggc ttgtccttga gaattgtatg ggataccagt 52140
aatgtgttta atattccaca tagagaaaaa tgtagctaga gcttggctag tatggcctgg 52200
ggtattatct gttttagtag aagctggaat gcccatcacc gcaaaacact gcaaaagatg 52260
acatttaaca caggcagaag actctcctgg ctggcatgta gctcagacaa agtgagaaaa 52320
ggtgtccaca catacatgta cataagctag tctcccaaac aagggaatat gtgtgacatc 52380
catttgccaa agtgaattag gttccagtcc tcgaggatta actcctcctc taaaagatga 52440
ggaatgtacc atttggcaag ttgggcatcg ctggataata tttttagctt ctttccaggt 52500
aatgctgtat ctgtgtttga gaccagaggc attaacatgg gttaaattgt gaaagtgtct 52560
agcattagat attgcattag caactaggtg atcagccatt tgattccctt cagtcaaagg 52620
tcctggaaga ggtgtatgag ccctaatgtg agtgatataa aaaaggtgca ttctactcct 52680
aactgctgtt tgcaattggg taaataaagt catcagttgt tcatctgtat gaaatcataa 52740
ctgagcattt tcaattaatt gtgtggagtg aactacgtat gaagaatcag aaatcacatt 52800
aataggcata tcaaaagcag tcaatacctc aattactgct acaagctctg ctttttgagc 52860
tgaaatatag ggcatctgga acactttact ttttgatcca gaataagaag ttttgctatt 52920
agtagaccca tctgtaaaaa cattttcagc accttcaatt ggtttaaatt tagttatttt 52980
agggagaatc caattagtta atttcaaaaa ctgaaacagc ttctttttag gaaagtgatt 53040
atcaacaata cccacaaagt cagctaaatg ggtttgccaa gtaagactaa ttataaaagc 53100
ttgctgtatt tgtgccttca tgagagggat aataattttt ccaggattat atccatgtaa 53160
tttaacaata caatttctcc caatccctat catagtagcg atttgatcta aataaggagt 53220
tagagtccat gaattagtat gtggaagaaa aagtcacttt actaagtcct gttcttggac 53280
gaaaacacta gtaggtgaat actgagttga aaaaaatagc aagtctagag tcttctctga 53340
atctattcta tttatttgag ctttatggac ttgcttctca atcagttgta actctgcctc 53400
agcctccttt gttaattgcc gagggctagt gagactagga tttcctctaa ggatagaaaa 53460
cagattactc atggcatagg taggaatgcc tagagcaggt cgtatccaat taatatcccc 53520
tagtaatttt tgaaagtcat ttaatgtttt cagttgatcc ctacgtatgg ttactttctg 53580
tggcacaatg gtagtgtcat ttactaaggt ccccaagtag gagtaaggag tagtagtctg 53640
aattttgcca ggagctataa ttaaaccagc atgagaaatc gaattttgca agtgatcata 53700
acattggagt aatatttcct gagtgggggc agcacaaagt atatatcatc catatagtga 53760

-continued

```
ataatttaac actgtgaaaa ttttttatga gtaggttcaa ttgcttgccc cacataggcc  53820
tggcaaattg tgggactgtt taacatgccc tgtgacaaca ctttccaata aaaacgctta  53880
gcaggctgca ggttgtttac tgcaggaatt gtaaatgcaa accattcaca gtcttgctca  53940
gctaagggga tagtaaagaa acagtctttt aaatctatga ctattaaagg ccaatttttt  54000
ggaattatag cagaagaagg caatcctggc tgtaatgctc ccataggttg tataactgaa  54060
ttgatagctc ttaagtcagt taacattctc catttacctg atttttttctt aattacaaaa  54120
actagagaat tccaagggga aaatgttgga gctgtgtgcc cattttctaa ttgttcagta  54180
actaatttct ctaaagcctc cagtttctct ttacttagca gccattgttc tatccaaatt  54240
ggcttatctg ttaaccattt taaaggtata gattctggag gcttaacaat ggcaaccatc  54300
aaaacttatt tcctaatctt tggcaggaac tttgattttc cgcttgaagt ggttctttca  54360
aaccttgcaa atttttttct agtcccatac aagggacata ccccatttca tccattgtat  54420
gttgacttca agggctatat aattgttctg gaattataac ttgtgttccc cattgttgta  54480
ataaatctct tccccataaa tttataggta cagaagttat aattggttga atagtcccag  54540
gttgtccatc gggcccttca caatgcaaaa tataaccact tggatatact tcaggggctt  54600
taccaactct acctatgtta aattgagtgg gttgaattcg ccacgtggac agccagtgct  54660
gcagagaaat gatcgaaatg tccactcctg tatctaccaa acctttaaat ttctttccct  54720
gaatggttgt ttcacaggta ggatgtttat cagtaatttg atttacccaa taagctgctt  54780
tgccttgttt atttgtgctt ccaaatcctc ctgttcgttt aatttcactt tttcccattc  54840
ccacatatgg cacgatcagg agctgtgcta tgcgctctcc cggctctgct ttccaggaaa  54900
cagaagtaga tataacaatt tgaatttccc cattgtaatt tgaatcaatg actcctgtat  54960
gtatttgtat ccccttttaaa cctaaactag accttcctaa aagtaatcct attgtccctg  55020
ctggcaaggg tccacagact cctgttggga ccttttgcag gggttcccca ggtagaaggc  55080
tcacagcttt tgtgcagcat aaatctactg tggcactact ggctgtggag agggacagac  55140
attgtacagg ggtgagggaa tggcctgagc tggaaatgcc ccagtttaga atggggccca  55200
ggatgggccc ctcatggcgt ttcccgaaat tgggttccct tctttatcaa acttagagtg  55260
acactgatta gcccaatgtt ttcacttttt acattttgga catatttcag gatcagcagt  55320
tttcttttct cccctgtctg acggcctgac tcgctgattt tttctacatt cttttttagt  55380
atgaccatgc ttcccacagt taaaacaagc tccaggaaat ggagtatttc ctttatccac  55440
tctcagtcct gccattgcat gtgctagcag agtagcttta tgcagattac ctctgatgcc  55500
atcacaggcc ttgatataat caactaaatg tgctttccct ctgataggtc gcagagcagc  55560
ctggcaattg ggattagcat tgtcgaaagc taataactgc agcactatat cctgagcagc  55620
caaatctgcg atcatctttc gaagagactc ctgaaaccga gctataaaat taatgtatgg  55680
ttctcttggt ccctgtttta tagcactaaa ggaaaggtat tgttctccac ctgaagtgat  55740
tttttcccaa gctctaatgc atactcctct aagctgctct atggcatcat cctgcatgac  55800
cacttgtgca tgtaaaccag cccagccacc aacccctaaa agttggtctg cagttatatt  55860
aatttgaggt tgggcctggg cattgtgagc agcctgaatg gtagcttcac ctgtccacca  55920
agttttaaat tgtaagaact gagcaagagt tagacaagct caagtaagag cgtctcagtc  55980
agtaggaatc atctgactgg aaacagcaac attctttaac agttccatta aaaaaggaga  56040
acgtggtcca tactgattta tagcttgttt aaattctttg agtaatttaa aaggaaaagg  56100
```

-continued

```
ctcaaatgta gctataatat ttccctgttg atctgggggc tgtattctaa cagggaactg  56160
ccaagcctct aaatcaccct ctcgtctagc ttactggatt cctgcctgaa tagaactaag  56220
agtggttgct caaggcgctg ctcgaacagt cactggggca actaattttt gcccagtgtc  56280
ctctggaaaa gaaagatctg gagggtcatt ttcttcaaaa taataaggag ggggtgcaga  56340
agggtaggga tgaacctctc cctcctttgc cactttagct ttagctggta aataaacatg  56400
ctctgtaacc tcttctgtta cttcgctata ctctatactc ttgttcctcc tcatcatcag  56460
tgtgaaaaag ttccaaggtg aaaccaacca gaccccacat ctgtcccatt gttaccctga  56520
cgcttctgag ctccccttct tactcaccac ggtgattgct ttaagagtac tcgggtatcc  56580
tccagctagt tttccattcc aactgtcgct ctggtgaccc tttgacctag atttgagccc  56640
ccacgatgga tgccacttgc tgagaccagc tcggtcgagg agaccctaac ccagtggcaa  56700
tagaggaatt aaagacaaac acagaaatat agaggtgtga agtgggaaat caggggtctc  56760
acagccttca gagctgagag cccagaacag agatttaccc acatatttat taacagcaaa  56820
ccagtcatta gcattgtttc tatagatatt aaattaacta aaagtatccc ttatgggaaa  56880
cgaagggatg ggttgaatta aaggagtagg ttgggctagt taactgcagc aggagcctgt  56940
ccttaaggca cagatcgctc atgctattgt ttgtggctta agaatgactt taagcggttt  57000
tccgccctgg gtgggccagg tgttccttgc cctcattccc gtaaacctac aaccttccag  57060
tgtgggcatt agggccatta tgaacatgtt acagtgctgc agatattttg tttatggcca  57120
gttttggggc cagtttatgg ccagattttg gggggcctgc tcccaactgt cactacccta  57180
ttaatgtctt tatcagattt tcagagtcat aggcaccttc taacttgctg ttctgccatc  57240
ccctatgtgg tctttatgca agaggctatg ttgtgaaaga ttgaagctgg cagacaaata  57300
ataggccatg ccataactac ttctttgggt ggtttatagt cggttttact tcccagatta  57360
tgaagagggg gattagcatt cctcttgaga ttgtcaaaag actcagtaac acacccaagt  57420
ttcaaaggcg aaacacaaga gcaaattttc atcactgctt taaaaaaatg tattgtggcc  57480
tctgcctggg ctgagggctc cgtggagcag ggacaggttg cttccaggta gcttcagtgc  57540
atcacattcc gcaaccgtct gcttcacacc ccagcccctt aagaaataca ctttggaagc  57600
agagctcgaa aaatttctct gttgccttcc tcagacctgc tccttatttt tttgataact  57660
ttggtcagtg tcactgtggg aagcagctag ctatctcgaa ggtgttagtt gttattcttc  57720
agctcactca cagacctgta aacacacaca cacacacaca cacacagatg cacacacacc  57780
tttcacctct ctactgatgc tggcagaacc catcttctgc tacattcttt gcatttctaa  57840
catcaacatg ttataacact caaggttcct aggccaaaat tttatccatt tcatgttctt  57900
tgaaagagac tgatagtagg tattccaggt cttttgcaca ttctacagat cccctgtttg  57960
tttctttttt ttatgctaag agggaaaaca tttcattcac tggaaccttt cttaattcac  58020
tgcatttgtt taggaaccaa tcctttcaaa actgctccag gtagagccct cagcaggtgt  58080
gcacgtgaaa tacatcagag aaagactgtg ctgtccagga taagagggaa acatgcatca  58140
ttttgaaaga gagtggggag ggagggaaag gcggaaaaga gggaggagga aagagagaag  58200
ctggaaaggt cagaccacca tcctgtcaga tactcaggct tgtaacctcc tctcccctcc  58260
tcacgtttat ttgctgaccc cagggagtag gttcccatag cctgtcattc ttctccatca  58320
ttgagtgaag ccctttattc tgtatctact atcatctctt taacctggat ggtgaatact  58380
aggctcccag agaatctttc tgccatcagc ttctccaccc tcctccactc tctgctacac  58440
cccattatca gaccaatctt ctgacagcac cactctggac aaaaacttca gtaagctccc  58500
```

-continued

```
cactgtccat taactaaagc tcagtagtct tggcctagaa ttcaaggctc ccctcctcct  58560
tgtggcccca actttattga cttatcacaa gccaggtact ctgttaaaag catctaaatg  58620
ttaatttgtc catctaaaat ccctttccag gaatgtgctt tctcccccac ttcctctccc  58680
agtctctgaa gtgttgcgct gctattgatg agagatgagc atatgatgca ggccagccag  58740
tcagagcatt tcacggcctg gctacaggcc agccaatcag aacccttcac agcctggcca  58800
tgggccagcc aatgagagct tttcacagcc tggccacagg ccagccaatc cgagcattct  58860
actctctgcc gccccaccgc cactctcagc tttctttctt tttttttttt tttttttttt  58920
gagatggagt cttgctctat cgcccaggct ggagtgcagt ggtactatct tggctcactg  58980
aaacctctgc ttcctgggtt caagctggtc tcctgtccca gcctccagag tagctgagat  59040
tacaggcaag tgccaccacg cctggttaat ttttgtattt ttagtggaga cagggtttcg  59100
ccatgttggt caggctggcc tcgaactcct aacctcaggt gatcttcttg cctcagcgtc  59160
tcaaagtgct gggataacag gcttgagcca ccgcgcccgg ccccatcctt agctttctga  59220
aatgtgatgt gtaggtgtgg tggagagggg gcttctctct tctgggtttg aaatctacac  59280
agagaagcag agaggagaag tgatggagaa tgagagagaa agggagacct gatgacactg  59340
tctctctgga tcccatggca cgtggggctt gttccacctc tggacttttc ccagagtgag  59400
tcaaaaacgt cccttgtttt cttcggcctg tttgagttgg gtttgctgtt acttgcagct  59460
gaagccatga agaaagtgtc ggaggcgagc gacgactatc tggacaggtg gcggggagat  59520
aaaagaattt accaagacag gccgggtgcg gtggcttacg cctgtaatcc cagcagtttg  59580
ggaggctgag gcgggcggat cacccgaggt caggagttgg cgaccagcct gaccaacgtg  59640
gagaaaccct gcttctttaa aaattcaaaa ttagccaggc atggtggcgc atgcctgtaa  59700
tcacagctac tcgggaggct gaggcagtag aatcgcttca agccgggagg cggaggttgc  59760
tctgagctga ggttgcgcca ttgcactcca gcctggacaa caagagtgaa actccgtctc  59820
aaaaaaaaaa aaaaaaaaat ttaccaaggc agttgtaggt agaaaaaggc agattcatta  59880
gagaaagtat gaaaatacct ttccaggaag caacgggcag gctcagcaga agaggcgctg  59940
actgcaaaga aacaaaggct tgctggaggt tttataggtt ggttctgagg ctgcagagtg  60000
tctcattcag tactgattaa cgccaaggtt gcagggagct aacttgcatt ttttcgtatc  60060
agctgaaggt ctggtgatag ctcggtgtag gaagattgtg agttatttgt gtaggagggc  60120
tgtgtgtcct ggagcatata gaaaggcaga cttgtagctt atctgcttct tctttttgct  60180
ttcccttgct cccaccagcc tgactccctt tccctaatta ggacgccaga gagagcactt  60240
aagagggcct atgtcatttg atcctcatga ccaccatgag gcaagactgt tagttcacca  60300
ttttgatggg gaagtgacac ctgagagata agccagtgcc caaggcctca cagtttttaa  60360
gtggtagaga cagaatttac agccaggcct ctgactccga ggctgctctc ttaacgatga  60420
gttccaaggc cttccaggaa aatgtacccg gtacttccta tgtgccgggc actaggctaa  60480
gcgccacaca cttgtcctct cctcatctgc tgctgtttcc agcgtgttcc acacgcccct  60540
caaacaggtc ctgggttttc ccacatctgc atctttacct ggaacatgct ctttgcccca  60600
cctctgcctg gcaatgttta cttatctttc caatcttgga tcaaatgttg agtctttctg  60660
gaagtctacc atactcagaa gcaagtactt cctccctgga gtcttaaggc ttttgatttg  60720
acccccaggc cagtcggctg cctttgagcg ctgatggcac aggaacttgt aggcatttct  60780
tagggagagt ggggaactga cagtttgaag ttaccagatt taggttctag ttattttgat  60840
```

-continued

```
ggcatctcgg caaaacacca cacttttcga taacaagaaa tgccactgtc atggaatggg  60900
cagtggcttt ggggtaagac agggctgggt ttgaatctgt ctctgcaact ctagagcttg  60960
ggtgacatta aaaagactac ccattctctc tgagtctcat ttttcttatc tgaatatgag  61020
gatgacagca gtgttgatct tagagatctg agagaagtaa atgggataat gaatgctaag  61080
ggcttagcac agtgtctggt gccatgtatg tatgttttta cataaaggat tacatcttaa  61140
actcattttt gcccctgcac gcagagaaga tgcaggtaac acacgtactt attaaatgaa  61200
ggaccaaatc ttatgaatat ccctccttta aaccttctcc tagtctttga tagcaactgg  61260
ccacttgtag ttgcttaaag aagctaaaga gaattggaag cagcaggatg gaagagaggt  61320
ggagggaaat gggagtcaga aaataaacgt ccttttaaga aaggccatca taagagcagt  61380
gcaggtgttc cagcgaggca agaaccaggg ttagctttgt tccttagatg acccacgctt  61440
cattccttac tttgtctttt cttagaggac acagggtgag atgaccaatg acataggctg  61500
cattgttcct tttggaattg tgcagtgttc ccagttcaat cttcctcata agcgggagtg  61560
aggcagtggt gcagtggtgg tgctgccatg gcggtaacag cagctgccca gcagcttcct  61620
gatctctggg ttgaaactct ggtggtgtga ccttgaaacc agtactcatg ttatgacccc  61680
tgacttctcc tccagctctt ccaacaatgt tgaaagcata taattatctt acttatatcc  61740
ctctctgctt gaaatactta gaggggtttc tgtttccact acttagctct gatgaataca  61800
catagcatat aaaaacaagc atattaaata ctagttttaa attgggcatg gtcacactgc  61860
tatagtccca gctactcagg aggctgacgt gggaggattg cttgaggcca ggagtttgag  61920
gctgcagcaa gctatgattg cactgttacc ggtggaagat atcagagtta ctggtgaatc  61980
tgtatgggtc tgcagcaacc tcagttcttc ctttctcaga agaaagaatt caaccgagga  62040
gcataaggca gaaaaagaaa ctgaggcaag tttcagagca gtttatttaa aaaggcttat  62100
ttaaaaaaaa aaggctttag aacaggaaag aaaggaaaat tcacttgcac ccaaacaggc  62160
acctgaaggt caagtgcagt gttgaacttt gatcctagga ctttataggc tggccccttt  62220
cccatgattc ttctctcaga gtgggctgcc cgcatgcaca gtgccctcct tatccttggg  62280
agatgagcat tcacagtgct taggaagttg tacacatgcc catctgaggc tttcttccct  62340
tttctggtgg agtgccctca gaaggtcatc ctttgccatt ttgtctccct tttttttttt  62400
ttttttgagt tggagtttca ctcttgttgc ccaggctgga gtacggtggt gcgctcttgg  62460
ctcaccataa cctccgcctc ccgggtacaa gtggttctcc tgcctcgacc tcccgagtag  62520
ctgtgattac aggcttgcac caccacgccc ggctaatttt gtattttttt ttttttttta  62580
gtagagatgg ggtttctcca tgttggtcag gctggtcttg aactcccaac ctcaggtgat  62640
ccgcccgcct tggcctccca aagtgctagg attacaggca tgagtcaccg tgcctggcct  62700
ccattttatc tcttaatgca catgcccagg aagttgtgtc tccctggtgc ctgcgctcaa  62760
ttaacacttc agtgcaacag gtgcaggcca tcaggacatg gcttctccct ggtgcaggct  62820
gccaatgtat ccccttttaga gaggcaatgt gatcattgcc aaaacatcac ctgacattcc  62880
tagcgggtgg gggaagagcc ctctccagcc ccactcatgc ttgtctaact acctgtaaca  62940
gcgctacttg cactccagca gcctgagtga tagagcaaga ctccatctct ttttaaaaaa  63000
ggaattttac aatgtgagtc aatttattta gaaaattata gcgatatgac agatatgaag  63060
gtggtcatca gtggtgggat gctgaagtgt gggaaacact ggtcttattt aataatcata  63120
accaggtagg cactattgtt accttcaaga gaaagagagg ctaaatgaat ccctcaggat  63180
tacatagctg ttaggtagtg tttctgactc cacagctcac tttctgaagc tggagaaagg  63240
```

-continued agttggaaat tatttggttg tcatcagaga ccaaacatca agtggcactg taactgcatc 63300
ctgaagaatg aataggattt atccagtgag gtagggaggg atttccaggc tgacaggctg 63360
acatggacaa aggtgtggtg gtgtgagtgg gcaccatgca tcatgggaac tgacggagcc 63420
ctgcagttct agagcagagg agttgtatgg gaacgtgact ggaggtgata cctgagaggg 63480
gagcaggaat ctagtcctgg gagtccttca aagctatgat gaggagatga cgcaattctg 63540
aaagccaagg agccatggga ggatattaga cagggtgacc tattcgcatg ggaatcttag 63600
agagttactt cattcggtgg agagctgggg cttaggatct aagccgatga ggaagaggtg 63660
ggctgaggag cctgtaggtg tgtgatgaga actgaaacaa tttccctcca cacagctggc 63720
tttctacatt gacatcattt tactattgcg ctgtcttcat taacatgact ttactattcc 63780
aggaaactct ttcccagaaa gatatatgtt acaaatacct tgtggttcat ttcaggaatt 63840
tcccaaactc atttaaatga atatcaaatg gttaaacttt tcagtagaaa gtgtgaaaca 63900
acagtttgct ccccagaatc ttttgaaccc cttgcctcaa aatccccacc tcactgtgtc 63960
ctccaatcct aaactcatat caagatcatt atcaaacccc aatccagccc ctccgttgaa 64020
atacctgcct ggaaccagac tccaaaacct catctccttt cgtcctctgc tttctgaaca 64080
ctattaagac tctggcaagt aagtagtttc ccttactgct gtgaggcttg gctttatcaa 64140
gtagtagtga aactgccttt gcaaaaatta tgacagtgag agaaatctga tatagctggc 64200
gtcatctggc ttctagcctc acaagctaat cccctttgtt aactgtaaaa caaagagaat 64260
aacagcctct tctaataaca gccaaaacta atattctcct tgcccaggaa ctgaaacagt 64320
ctttgtaaga ctcctgaaag tccccaagat taggattatg ggaggggcct gaattctgct 64380
aaaatgtagg cgtagttaaa tgattaacag ctattgttcc ctagcttgct tttctgtaaa 64440
tccttacagc tcaagagtaa cgtagctggt agctgaaggg cacaagatct gtaacttccc 64500
caatcccaat tgctcctaca gataacatca ttattgtcaa aacctaaaat tgatctttga 64560
gatatttttc agacttttgt attctggcaa ccaactgact ccacctggac ccgtgactca 64620
taccaaggaa catgacaccc acacagaaac tcccatccag aaacaaactc agcatgcgaa 64680
gacacttcgg acactaacat atttcattcc caatcaatca gcagcaccca tttcttagcc 64740
ccctgcctgc caaattgtac ctaaaaaccc tagcctcaga gcttttgggg aggtgaattt 64800
gagaaatgtt tcctgtactt ctgctcggtt ggtgataatt aacatttttt ttctaatttt 64860
tttaaaaaaa tcacttggat cacttgaggt caggattttg agaccagctt ggccaacctg 64920
gtgaaacccc atctctatta aaaatacaaa attagtcggg tgtggtggtg tgcgcctgta 64980
atcccagtta ctcaggagac tgaggcagga gaatcacttg aacctgggag gcagaggttg 65040
cagtgccaag atcacaccat tgcattccaa cctgggcaac agagcaagac tctgtctcaa 65100
gaaaacaaaa caaaacaaaa caaaaacaaa aacaaaaaca aaaaaccacg gttgacaaag 65160
aaatttgtta cctctgtagc acacaataat ttaacgtaac agttattact gataatgtat 65220
actaagtcct accagaatta taggagtttc acataacttt tgaacacata ccagtaagat 65280
acttctacaa atacagccca aagaaagtca aacattattt catatttgac aatgcttcct 65340
gtataatttt tatgccaaat aagccaaatt atgttatttt tggactttag gaaacctaat 65400
atcttaaaag attaattaag tcagaaaaag acataattta taatttttgt taaagagcag 65460
atcagtgctc taagaaaaac cggttgtgct tttattccaa tattcaattt attgaaaaac 65520
tgaagattaa ttcctttaac tttagccaat atgttcacac acataatttc ttttgtaaga 65580

-continued

```
ccaatttttc agaaaccttc caaaaagtca aagaagcagt tcattacctt aaagcattta  65640
gcaaacctaa tatatgacct gcataattta gaccaaatgt ctacattttt gaagatattt  65700
ttattttacc agtaatcttt aaaaccattt ttatttctca aagattactc aagtcatgtg  65760
aactaaaatg catcacactt tttatttttc tgacaaaata tttgcctacc tagttattat  65820
acaccaaagc tctctcataa tgggaagtaa tttttaatac ccccaaaagt aaaaaatgtc  65880
agttaatgca atgcaaaaca gtacaaagcc ttagattttg agaggaatct atccactttt  65940
taatccctgg ggttccatga ggaaaacaga ggtttttccc aaaatgggat ctgtggctcc  66000
tcctatgttt tccccaagga tttccaggct gttagagctt gaataagctg acttaaccac  66060
agtgctcttt taaaaagtcc ttttaaatct cgtattacca gactttagcc aggccaaacg  66120
gccaagattc ctggcttttg aactttacca aaagcaacct cacaggtgaa accaacaagt  66180
cttaactaaa gttatggctt aatcacgagt gtatgaggta ttttcaaaaa ggtggtaagc  66240
agtttttaca agatctagaa tctccagtgg tagctaaaag aaaggaagat tcaagaaggg  66300
aaccagaaat tgtacatgga ggggaagaga atcaacaaat gttaaaggtc atgcagaaat  66360
caaaccagaa aggggtcatc tcctaagctg gaattgaacc caggccatca ttgtaaaatg  66420
gcagagacca agagacagta ctgccacatg gttacaaggt caagctccca aggacatgaa  66480
acaagatgag agggaaactt tatccagttt ttttggtttc agagacctgc agcaaaattt  66540
gtaactgacc agtttgctgg accatcttga acagtgggtt tacaggggtc ctaggcttgc  66600
attctatcct acggtaccca tctttatgac agaacaatac agaaagacac acaaagcaca  66660
ccagatttgc tacagcataa gattaccctc acaaatcctt tttctcatta attaaaactt  66720
tacagaagat aaacagagat ttttaccatt cattcaatca gtttgcacag caagagagag  66780
aggccagaag tctgactggt aagaaattct taccctttg ccagcatgcc aggcttctgg  66840
gttccctttg cctgagtggc cctagtgacc tggcttgctg caccatagcg ctgggggcca  66900
accctcaaca caaaggaaaa ttatcttttt ccattctggc tggagcaaaa tatgtgtgac  66960
aaaacacaga catcagccac tctgcttagc acccaatatc aaactggcaa agctcaaact  67020
tgccccccggt tggccccata attgttaatc cagtctccaa ccaggagttt caatttgtgg  67080
tctctgggca agatggtagc cctgggtaat agaaaagata agaaagagaa aggagagaaa  67140
aggagtgaag cgtagtctgc agtagggtgg ggaaggtgaa gagctcagag aggccagaga  67200
aaaacccacc catcccagcg atgctgaatc aaaagttcag gtggcttctt gtcagtcacg  67260
aagggatctt ttccagcagt ttcaccagct ctcaagtttc ctcctttagg gaggaaaaag  67320
ctccccatgt cccatgatcc tgtacatgac taattctgtc acccacagcc accagcaaag  67380
agtgcaaggc agacttatcc aaagaaatag cagttaacat cctgtaatgc caaacctgtt  67440
cttagctgag agggacttta ccaagacagg cctccaaccc cctaaatttt aggaaggact  67500
ctaatcttcc taagttgggc cgtgaaccaa ggtttggtca agcatccttg ccttttctta  67560
agaggggtct ttaaccctct ctgtcttagg agagactcta actcccctaa gttgggcccc  67620
taacccaatc ccatccttga cccgggtact ccaccatgta cccaaaatca gtcagtcagt  67680
gctagtctat ttcctttgag tcgagggtct cctcagtgta gtcttttcat ggctctccag  67740
aaagttgtta ctggaaaggg gtcctgatcc agaccccaag agggggttat tggatcttgt  67800
gcaagaaaga attcagggtg agtctataaa gggaaaataa gtacataaag aaagtaaagg  67860
aataaaagaa tggctactcc attggcagag cagccccaag ggctgctggt taccctttt  67920
aatggttatt tctaaaatat acaccaaaca aggggtggat tattcctgcc tccccttttt  67980
```

-continued

```
agaccacata gggtaacttc ctgacatagt catagcattt gtaaactgtc atggcgctgg  68040
tgggagtgta gcagtgagga caaccagagg tcacgctcat ggccatcttg gtttcagtgg  68100
gttttagctc gcttctttat tgcaatctgt tttatcagca aggtctttat gacctgtatc  68160
ttgtgccaac ctcctatctc atcctgtaaa ttagaatgcc taaccagctg ggaatgcagc  68220
tcagcaggtc tcagccttat tttgcccagc tcctattcaa aatggagttg ttctggttca  68280
aacacctctg acaattttgt ttattttttg tagagatgag gtctcattat gctgcccagg  68340
ctggtctcaa actcccaggc tcaagtgatc ctcctgcctt ggtctcctga agtgctgaga  68400
ttacaagtgt gagccactat gcccagctaa ttaaactgtt tatttgctgc aacacctgat  68460
gttcttagtg cattagcttt tctggacagt gggcaagacg aacccattag gttgttacag  68520
tttgggtggt attttctggg atctggacct ggagaatctg ctcaatcaga agagggagcc  68580
agccatggtg gcacgagcac ctgtagtccc agctacttag aagactgagg caggaggatc  68640
acttgagccc acgagtttga gtccagcctg ggcaacatag tgagaccctg tctctaattt  68700
tacgaaaaga gagagagagg aaatagggga agaagagcca gggataagaa atgcagagga  68760
cggccgggtg tggtgggtca cgcctgtaat cccagcactt tggaaggctg aggtgggcag  68820
atcacgaggt caggagtttg ggaccagcct ggccagcgtg attaaatccc gtccctacta  68880
aagatacaaa aaaaattagc tgggtgtggt ggtatgtgcc tgtaatccca gctacttggg  68940
aggctgaggc aggagaattg cttgaaccca ggaggcagag gttgcagtga gccaagattg  69000
cgccattgca ctccagcctg ggtgacaggg tgagactcca tctcaaaaaa aaaaaaaaaa  69060
aaaaaaaaga aaagaaaaga aaaaaagaaa tgctggggac atcaacattc aaaggcagtg  69120
ggggagccaa ggtaattttt cgacagagaa tccagtatta gcctaaattc catctagatt  69180
cacaggccct ggaaagcagg actttgagaa atggagagga ggtaatttgg aaccaggagc  69240
cttcagatgg gtagaacaca gtgagtgcta ggtacaggtg agggtggcaa ttagaaacca  69300
gccccagcct gatgcatggt gggacacagg tgatggggtg tctggaattg gagagaagtg  69360
tgggaagtga agtgagaggg tgctgagaca aacttgactc tggaatttcc ccaggcaggc  69420
tctgactggg ctctcctgag gaaggacttc ggcttggtag ctggagcagg ttccctgggc  69480
caaggggagg acagggtggg gcagacccta tgagaatggc tgcaagactc ttactgcaat  69540
aactcagtga gctgccatcc tccccctccc ccaccacaca aactcccctt cccactttgt  69600
tgatgatttc ttagctctgg atgcttccgg tccatttata gctaacctta taatcggatg  69660
catacttgtc attttataag tagagctctt ggtcactctt tgcccatcaa ttaactcaat  69720
tgtggtgttt gttgtctgtc ctctttctac tttctggata ccttgtatgg acctagatgt  69780
ggttccaggg acactttgaa tagaaaggcc aggctgagat gagggttggg cctggaggcc  69840
ccttggacca ctggacatca gaacatttac tcacgtgcca gggactctaa gtcacccaac  69900
tgaacaacta caccttctag atttagaaga atgcacatac atagtttcct ctcaggcccc  69960
tgctttctcc cctccctttc ttcccacctc ccttccactt actggcagaa atatatccac  70020
cctgtattgt gttaagatga ctttattgca tttctaaagg gcaagtgtgt tgttggtagg  70080
ctccctttta ggaagctgaa aggcttgcct gagtgctggg tggggttaga gccaggaccc  70140
cagtcttctt ccattcatgt gtggagaaac tgcttttagg aaattgctta cagtttgttt  70200
tattattccc tctgcttgga ctatgtccat tcattcattt attcaacata tatttattga  70260
gcacctatta tatgtcaaaa tgcttgctct cgtggagctc gtatttgaga gtaatgatat  70320
```

-continued

```
cagaatgcac atattatata tgtattacat atatatataa ttaggttgaa gaaaaacaaa  70380
acaaggtagc atggtaaggg gctagaaaat gatgaggact gatattttag gaggagcaga  70440
gaacaatgac ctgactgaag tgaggaaatg agccacgtgg ctctccagga ccagaagttt  70500
caggcagagg aatagcacgc gaaaaatcca gagactaggg aggtgggtgt ttactgtgtt  70560
tgctgtcttt gaggatgagc aaggatgcca gtgtggctgg agtggagcag gagttgagaa  70620
agagtggtag ggaggtgggt caaagaagca gccagagctg tggccggact ttgcattttt  70680
ttctgagcat gataggaagc agctgagcaa gggagggact tgatctggat tctatttcct  70740
gctatgtggg gtgagggagg aagcaaggag agcagctggg agagacagag tataacagaa  70800
tcggggtcta ttataaagga agagcaacca gaattttcta atggaaaagg atatggagtg  70860
tgaaagcaaa agaggagtag taaaagacac caagggtttt ggcctgagca actcaaggac  70920
agggatgtca tttaccgaga tgggaagtgc tggagaggaa caggagtgag ggtggccacg  70980
gtgaaatgtg gctttgggat gtgtggtgga gatgtggaga aggtggaggt gttaacaagt  71040
ctagagtgct gggatgaggt catgttggac atgtaactct ggggattatc aatgtatgtt  71100
ttgaaagcca ttaagattgt ctgtaaagaa caagatggta agtgttttag gattgtccca  71160
accactcaac tctgccatta taatatgaaa gcagccatag acaatatgtg aatgaatgat  71220
catgaccatg ttccaataaa actttatttt agaaagcaga tagtgggtca gattttggcc  71280
cataggatat agtttgccaa atcttagacg aggtggtatt acctaggtag actgtaaaaa  71340
gaaaagagaa gaactcagag ccttggggca cccaacactt agaaattggg aagaggagag  71400
ggatctaaga gaatgagata taacaagcag caagggaaca ggcaaattaa gagattgggg  71460
tggcatggga gatggaagat gtttcaagaa ggacaaacca atattatggt gccaataaac  71520
gttgtgaaat acactgaaat ggacaaaaaa attgagtgtt ctgtctagta tacccttcag  71580
ggttatattt atttttcatt gcttttgagc tattttacaa ctttttaagt tgtagaaaac  71640
tgacaataat gcaaatgatt cttgtctatg aaaacaaatt atgtccagta caatgcaatt  71700
aattgcactg gtggaattgg tagaatgcaa ttgccctgtg aataaaccag ttttgcatct  71760
ataatcatgt gatgcttaac cacaaggata tgttctaaga aatgcggtat tgttaggcaa  71820
ttttgtcatt gtgcaaacat catacagtgt gcttacacaa acctagatgg tatagcccac  71880
tacacaccag gctgtagggt agagcctatt gcttcgaggc tacaaacctg aacagcatgt  71940
tactgaactg aatgctgtag gcaattggaa cacagtggtg aatatttctg catctaaaca  72000
tatctaaata tttaaaaggc acagtagaaa tacagtaaaa aagatttgaa atgctacatg  72060
tatgtagtgc acttactatg aatggagctt acaggactgg aagctgccct gggggagcca  72120
gtgagtgaga gatagtaaat gtgaaggctt aggacattat tgtacctgat ggtagatttt  72180
ataaacactg tacacctagg ctacattaaa tatatttaac gttttttttct ttcttcaata  72240
ataaattaac cttagattac cgtaacattt ttatcctatg aacttttaaa ttttaacaat  72300
cttgttgact gttttctaat aatatttggc ttaatacaca aacacattgt acagctgtat  72360
aaaaatattt gttctttata tcctcattct ataaactttt ttaatttaaa tttttttttt  72420
tttacttttt aaactttttt gttaaaaatg aagacagaaa cacatacatt agcctaggcc  72480
acacagggta aggattatca atatcactgc cttccacctc tactccttgt cccactggaa  72540
tgtcttcaag ggcaataata tccttggggc tgtcgtctcc tatgacaaca atgccatctt  72600
ctggagcacc tcctgaagga cttatcttag gctgttttac agctaacttt tttttttctt  72660
ttgagacaga gtttcacttt tgttgcccag gctggagtgc aatgcgtgat cttggctcac  72720
```

-continued

```
cgcaacctct gcctcccggg ttcaagcgat tctcctgcct cagcctcccg agtagctggg  72780
attacaggca cccgccacca cgcctggcta attttgtatt ttttgcagag acggggtttc  72840
tccatgttgg acaggctggt ctcaaactct caacctcagg tgatctgcct gccttggcct  72900
cccaaagtgt tgggattaca ggcatgagcc accaagcccg gcctacagct aacttttttt  72960
ataagtacga tgagtacact ctaaaataat gatgaatgta cagtatagta aatacgtaaa  73020
ctagtaatac agttgcttat gatcattatc aagtcctatg cactgtacat agttgtatgt  73080
gctatgcgtt tatacaactg gtagtacggt gaattggttt acaccagcat caccacaaat  73140
acattgcgta atgcattgtg ctatgatgtt aggacagcta tgatgttaca aggcaacagg  73200
aatttttcag ctccattata ccctatggga ataccaacat atatggggtc cattgttgac  73260
caaaatgttg ttttgcaatg tgcaactgta tttgtaaatt tagaatagca ttccttattg  73320
cttttgtatg tgagtttcat taacttcttt aaactggttg taacatctta ccggttccct  73380
cattagtgag taaaataaaa tcatttacat gtattcattt tatatttgta tgtgagccat  73440
gatttcactt tttgaaataa ttattatttg acaatggaga ttaagttaaa taaatattaa  73500
gaattaacaa aattggcaac atacagatca tggtgacttt gataagaacg attttggagt  73560
aggaagggtg aaagactgat tggagcaaat tgtgtaaagc tataataaat aataaagaca  73620
catgggcaca ggggtaaata aatagaccaa tggaacagag ttagagatcc cagaataaac  73680
ccacacataa atagaaactt tgtagatggc agagatggta atgcaggaaa aggatggagt  73740
agtcaataaa tggggctggt acaatttgtc atctatatga gaaaaaaaac aaaactggat  73800
ctctacctca aacaaatcag tctgttccag tggatttaag atgatatggt ttggatctgt  73860
gtccttgccc aaatctcacg tcgaattgta atccccaatg ttggaggtga gggctggtgg  73920
gagatgactg atcatggagg gggatttctc atgaatagtt tagcaccaac atcttggtgc  73980
tgttctccat gatagtgagt gagttaatgt gagatctggg catgcaaaag tgtgtagcag  74040
ctctttacct ctcttgcttc actctggcca tgtgacgtgc ctgctcgccc tttgctctct  74100
gctatgatta taagtttcct gaggtctccc cagaagctga gcagatgcca gcaccatgct  74160
tcctgtacag cctacagaac agtgagccaa ttaaaattct tttctttgta aattacgcca  74220
tctcaggtgt ttctttatag caacgtgaaa agggactaat acagactttt agaagaaaat  74280
agaagggaat atttttgtgg cctcatggta atgaaaaaaa tttaaaataa gacacaaaat  74340
cacaaacctt aaaggaaaac atttatgaat ttgacaccat taaaatttta aaaacttttg  74400
attatcaaaa gacacattaa agagattgaa aacacaatta ctcataacac ttaactgaca  74460
aaagataggt atccagattc tgcaaagaac acttacaaat caatataaat aaaaataact  74520
taatagaaaa atgtgcaaaa aatatgaata aacaattatc agaagagaaa actcaaatga  74580
tcaatgaaca tatgaaaaga tgtaaaacct cactactaat tagagaaatg caaattaaaa  74640
ccccaatata atactatttt acatctcttt aatggactaa tctttaagag tgtgatgatc  74700
caagtattgg caaagatgtg gggacattag aacttttata ctctcttgag tggaaggtaa  74760
attgttataa tcactttaga aagcaatttg gcaatattta atattttaag tttttctaag  74820
cagttttcca ggggttgttg tgttataggg tatacatata acacagcaac tcctggagat  74880
ataccttaga aaaactcaca aatatgtaca gagggacagt ttatagcaat ggtgctgtag  74940
taagattttg gctataacct gcctgtccat caataagaaa atgattaagt aaattgtggt  75000
ttattgagac aatggaatac tatgtagcaa tgaaaaagaa tggattagag ctgcatgtat  75060
```

-continued

```
caatatggat gaatttcaca aacagatgtt caagggaaag agcaagttgc acaatacatg  75120
ttcataccta gttttcagtt tacagatctt gcacattttt gtcagattta tccctaagta  75180
tattttaagt gttattgaaa atggtatttt aggctgggcc tggtggctca tgcctgtaat  75240
cccagcatgg ctttgggagg ctgagatagg aggattgctt gagcctagga gttcaagatc  75300
agcctaggca acatagtgag acctccactt tacaaaagaa ataaaaatag ccaagcatag  75360
tggatcatgc ctgtaatcct atcatttagg gaagcaaagg tggggtatag cttaagccca  75420
ggagtttgag acctgcctgg gcaatatagc gagaccgtgt tctctacaaa agaggggaaa  75480
aaagaaaaaa taaataaaaa tttacaaaat tagctgggca tggtggtgca tgcctgaagt  75540
cacaaatact caggaggctg aggtgggagg atcacttgag cccaggaggt tgaggctgca  75600
gtggactatg atcattccac tgcagtccgg cctggacaac acagtaagac cctatatcaa  75660
aaaaaaaaaa aaaaaaaaga agaaaacagt atttaaaaaa ttccaatttc taattgttcc  75720
ttactagtat atagaaatac agtagactgt tgtatattaa tcttatatcc tgtaactttg  75780
ctaaaatcac ttattctagt agctattaaa aatagattcc atcagatttt ctctatattt  75840
gaccatgtca tctgtgaata aacacagttt tatttcttcc ttttcaatct gaatgccttt  75900
ttttccacct aatgctctgg ttagaacccc ccatacaaag ctgaatagaa gcagtgagaa  75960
cagacatctt tgtctagttc ccaatcttag ggagaaaaca tacagtcttt cacatgaagt  76020
atactgttag ctatgggttg ttttttggag atgcccttta tgagatggat gtaattccct  76080
tctattctta gtttgttcag tgtttttatt atgaaaaggt gttggcttct cccaaatgtg  76140
tttttgcat tgactgggat aatcatgttt tttcatatgg tctgttagta tggtaaatta  76200
tattgcttga ttttcagatg ttaaatcact cttgcattct tgtgataaat ctcatgtgct  76260
catgatgtac ttgtcctttt aaatataaag agacatccaa tttgctaaag ttttgttgag  76320
aattattgca tctatgttca tataggtata ttggtgtata gttttcttgc cttgtaaggt  76380
ctttacctgg ttttgatgtc agagtaatgc tggaccattc agtgatttgg gacgtattca  76440
ctcatcttca acttccttga acagtttgtg cagaatcaat attatttcta ccttaaatgt  76500
ctgactctgg ggctttcttt cttttctttt tctttttct tttttttgag gcagggtctc  76560
actgtgtcac ccaggctgga gtgcagtggc ccagtcacgg ctcactgcag cttcgacctt  76620
ccaggctcaa gtaatcctcc cacctcagcc tcccaagtag ctaggataac aggcgtgcac  76680
catgatgcct ggccaaatgt tttgcatttt ttatagagat gaggtttcac catgttgccc  76740
aggctggtct caaactcctt gactcaggcg atcctcctgc ctcagcctcc taaagtgtta  76800
ggactacagg tgtgagccac tgcacgtggc caaccctggg gttttctttg tggaaacatg  76860
tgttagtcta tttgcattgc tataaaggaa tacctgagac tggataattt ataaagaaag  76920
gagatttatt tggctcatgg ttctgtaggc tgtacatgaa gcatagtgcc agcatctgct  76980
tctgttgagg gcctcaggaa gcttccagtc atggcagaag atgaagcggt ccctgaatca  77040
catggtgaga gaaggaacaa gagagaagga ggaggaagtt ccagactctt tcaaacaacc  77100
agatattgtg tgaactcata actgagaatt cactcattac tggggaggat ggcaccaaga  77160
cattcatgaa ggatccatga tccaaacccc tcccaccagg ccccacctcc aacattaggg  77220
actacatttc aacacgagat ttggagagga caaacatcca aactatatca gaaggttttt  77280
aattgcatat tcaatttctt taatagatgt aggcctattt tggttatcta tttcttcttg  77340
agtgttgtta gattgtattt ttcagtaatt tgtccatttt atccatattg tgacatttct  77400
atctggtgta ataagaatag tgttcatatc aaagttcaat ttctccatat cttttccagg  77460
```

-continued

```
taactctccc tttggtgctt tgaagcaata tggcgtcttg actggctgcc atggccccca  77520
cctttcctcc taggctcagc ccttgacata actactcctc actaccctct catcttcccc  77580
ccaccttgta tccctctagc attcctcacc tgaagaactt aggctttctt aagtctcttt  77640
agttagcagg aaactatcta atttaaaaac cctctccaag ttgtttatta cttaagggat  77700
tagtccttcc aagagtattt atgtttcaga agagaatgtc tagataggat tgtgcataac  77760
aaaaataagt caatttttaa tggtgttatt gtaggctctg tgacaagtag gggagggaag  77820
cactttggga aatggactct cctctctttc aaatattatt caagtacaag tttgcgcctg  77880
ttactcttct gctttaagac tgtctacagg gagttctcct tgtcctttgg tcaaagtaaa  77940
atgttcaaca cagccttgca agatcctgcc gcttctcgga gccatcagac ccactcttga  78000
tgctctgctc tggtagagct ctgccctggc cctcaaactg ttggacttct ctgagaaagc  78060
gataggtgtg ctcagatttt aaggatgagg tggagaagtt cagagagagg gcatttgcta  78120
tggaactgag gctaccaaag tgacgaagag aatgcatccc tgttctctag gaactcaagg  78180
tttagtggcc ttatagagtg gaatagcacg ccaacagtgg ggccagtgac tgccaggctg  78240
actagagaag gcaactctca ctgtggatat agtcggaaac tggcttttct gcttcagcgc  78300
tgtggaccag caattgacct ttcttcccta aagttcattc acttgatacc ttccagaagg  78360
aaggtcaccc cctgcctggg ttggctatgg gccaaacccc tgcccactcc aaagtgtggc  78420
ttggaatgcc atggtctgct tattaaaaat cagatttcgg gaggccaagg cggtcggatc  78480
acgacgtcag gaaatcgaaa tcatcctggc taacacggtg aaaccccgtc tctactaaaa  78540
atacaaaata ttagccggac gtggtggcgg gcacctcccc gctacttggg aggctgaggc  78600
aggagaatgg tttgaacccg ggaggtggag cttgcagtga gccgagattg caccactgca  78660
ctccagcctg ggcgacagag cgagactccg tctcaaaaaa aaaaaaaaaa aaaaaaaaaa  78720
aaaaaaaaaa aaaaatcaga ttcctgttcc ccaggcatcc tgaatcatca gggatggagt  78780
ctcaaaataa atgtacattt atttattttt tatttttgta tagacgaggt gtcgctatac  78840
gttgcccagg ctggtctcaa actccttggc tccagcaatc ctcctgcctc ggcctcccaa  78900
agcactggga ttataggcct gagccaccac gccggcctaa ttgtactttt atttttttga  78960
gacggagttt cactcttgtt cctcaggctg gagtgcaatg gcacgatctt ggctcaccgc  79020
aacctccgtc tccagggttc aagcgattct tctgcctcag cctcccgagt agctgggatt  79080
acaggcatgt gccaccacgc ccggctaatt ttgtattttt agtggagacg gggtttctcc  79140
atgttggtca ggctagtctt gaactcccga cctcaggtga tccgcccgcc tcggcctccc  79200
aaagtgctgg gattacaggc gtgagcaagt gcgcccggcc ttaaatgtac cttttaaacc  79260
aagttctgca gtagattctt aggcattaaa gtttgagagc catgtttctg aggggcgtca  79320
tgctgaaggc tatatattct tgcggccccc ggaccgagcc tagcccttgc attcccaccc  79380
tgggctctct ctcagcgaca acttttccca ggcgtcgggg cttccctcga gcgtggcgac  79440
cccgcagaca tggtgccaag agccagggtg ggcggcgggg cgggtgggag agcggcggcg  79500
ctgggggcga gggcaccatg cgaccgcggg cgccgggacc acagcgcgcc gggaaggagg  79560
ccgaggcggc aggaaaaaag ccgaagatac ttggggggac cgaggggcca agcgacggag  79620
ggaggaacag aatacagcct cgcgctggtc ccgagcactg ggacgcgcgg ggagagcagg  79680
aggccgggcg gggaggttcg gggcggggcg cgctacccgc agtccccgga gctcggctaa  79740
ctcggcgccc agtgcacggc cgcaccatgg ggtcccgcca cttcgagggg atttatgacc  79800
```

-continued

```
acgtggggca cttcggcagg tatgggggag gggccccgcg gcgccacgcg ggaggcggcg  79860
ccgaggggtc tgtttctttc cgttgcggcg gggttctcgc gcggcgctcg cgatccgaaa  79920
acatctccac ttcctcctca ccccgcgcag tcgggacacg ggcgtccaga cgccggcccc  79980
tagctgggct tctcctctag gcctctggca gcgggacctg gcatggtgag cagaggcgct  80040
gggctcgctc ggagtgcgcc tgttgccggg caggagggac ctggtgcgtg ctctccgcgg  80100
cagcagatgc tggaggcatc tggctggaga tctggctcga ggggccagat ctcactcgta  80160
gggggtgcct gtgcctggcc gcccgtttct ctaatccgcc gccacttccc tagacggctg  80220
ctgcccagtt ctgccctgcg cctccgtagg gcctccctct gtgcctggca ggtgttcccc  80280
agggacaacc gttagtcaga gttggttgcc gtttattaaa acctaatacg tgccaggtac  80340
actgtacctg gcgcttacac atagttcttc atttgatgtt caccgggacc ctgcaaagga  80400
ggtgttcaaa tccttatttt agtgattggg aaacaagctg gcggggtcaa ggactcatag  80460
ccaacgcatg gtggaaccac gtttaacctc cgtacaccct cttttcattt gtcaaattga  80520
tttaaaaaat ttaaattatt cattcgttcg ttcactcatg gacagagctc ctctatctga  80580
ctcagagtgt tttgagaggg gaggtagccg ggtgaggggc catgcagcgt tatggccgga  80640
gatttggagc tgcgtctcga tcctggcctg ctacttacct ctgatatgat tctggagata  80700
ctttgtgtgt cagtttccta tccagaaaac gggaatcagg cttagcaaag agatgatgtg  80760
gtgctgttct tcaaggtgga aggttgcatg cgttttggtt ttgattccca gtgtctgcaa  80820
aaaggagctg ttaggacaga ggaaacgggc aggaagcccc agctgttccc ttcttcctct  80880
gcttgcatca ttgaacgctg ccttgtgcct ggctcggtca taagccgttg gtacatgtta  80940
cttcctttaa tcttcactac agccttataa ggttggtagt atcaccctct tttcacagat  81000
gagaaaacca aggtttctgc ctaagcacaa atctaatact agcagggcag aattggatgc  81060
cattggatgc ccatcacctc cacagcccac actctcaacc atgatgcact cctgagcacg  81120
gttaggtgac ggctcctcag ctgggccaag ctctttatgt atgatctcat ttcatccttc  81180
tggaagcaga atagcacaga ggttaaaaga tcagttttaa ggctggatgt ctaagttccc  81240
actctggcgc taccacacat taactatacg gtcttgagca ttttatttac cactttctta  81300
tctgtaaaat ggggctaata atagtacaaa tgttttcaaa taggagtagt gaaaatgtgt  81360
atatgaggac tctgcatgca gtttctcatc cttacagtaa ctcaatgagg taggtggtac  81420
ttacatctta gttcccctgt gttttttagg gattagctga ggtaattata ttagttggtg  81480
tttgactaaa gtgcccaatc aaacagattc ctcaaatgga agtttatgcc tctccagtaa  81540
ctgcccacag caggatctgt gccacgagac cattcaagga ccctggcagg tgggacagct  81600
ctgtcatcca ctgcatgggg ctccctgtct gtgcctggag cagctgcgca cccatggtga  81660
cagctcacta cggtgaagag gggcaaatg ggtttgagga gacagctctt agctggccac  81720
cataatgtat gcaaaagtct tattattcag taagttctca ataagtcatg gctattatca  81780
ttacctgagt tcccatattg gtggtcaggg ttgactcgtg aaagcagctt acaggaggga  81840
aaagggtaac aaaccactgc ttatatagca gaagatgaag actgtgtgac tgcaacacag  81900
taccacattt ttctcaggta tttgttctaa ttggtatcta ttctttataa acagaaagga  81960
aagttattgt gatgattatt tagtcctctc tttaagggat cctagtgaaa gtgttaagta  82020
gagcagtggt ccccaacctt tttagcacca gggactggtt ttgtggaaga catttttttcc  82080
acagacctgg tccctaacct ttttagcacc agggactggt ttcgtggaag atattttttc  82140
cacagacctg tggtggggtc gggaggatgg tttcaggatg gaactgtttc acctcagatc  82200
```

-continued

```
atcaggcatt agattctcat aaggagcact cagcctagat ccctcgcatg tgcagttcac  82260
aatggggttc acgttcctat gagaatctaa tgccgccgct gatctgacag gaggtggagc  82320
ttaggaagta atgctcgctg gccgctgctc acctcctgct gtgtggtcca gtttctaaca  82380
ggccatggac cagtctggtc tatggcctgg ggctttggga cccctacagt agagaaccct  82440
gattacctct catttctcat tggtcatttc tagaataagg aagcactatt ctagtcacct  82500
ttaaaagggg aaaacaggcc aggtgcggtg gttcatgcct gtaatcccag cactttggga  82560
ggctgaggca ggcagatcac gaggtcggga gctcgagacc atcctggcta atgtagtgaa  82620
accaagtctc cactaaaaat acaaaaaaat gagcctggca tggtggcggg ggcctgtggt  82680
cccagctact tgggaggctg aggcaggaga atggcgtgaa cccaggaggc agagcttgca  82740
gtgagccgag attgcgccac tgcactccag cccgggcgac agaacgagat tccgtctcaa  82800
aaaaaaaaaa aaaaaaaaaa aaaaaaaaaa aaaaaaaaaa aaaaaaaaag ggaaaacagg  82860
atacctgaga agaactaaaa taccattcca ggatttctcc tgaaaccata tcgtttccat  82920
aaacttcaca gcttaagctc catatgaaaa gaaattgaga agactgaaat ttaggcacct  82980
gtgttgggag gatctgaacc tggatccctg agttagttgt cctgggttaa gaggagagac  83040
ggtttaaaag tttagagttg gaatgtggag cctgtggcag accttcatca atggatagag  83100
gtagggtttt gttttgtttt atttcagtat atagagtttt tctggctctt ttttgacttc  83160
agtgtgtgaa catcataaca tctatcattt atatacagct acggtgtgtc atagagtgct  83220
ttccatgtgt taactcattt cattcccaca aagcccatag tttagatgag gaaactgagg  83280
cacagaaagg ctaaggatct tgctcatggt ccctggtggt aagtaacagg gccaagatca  83340
aaccttggca gtctggctcc agagtccatg ctcttagcca tgatggactc caccagttat  83400
gcttttatat ggaatggtat aatctaggac tgaaagcagt tttcttcatc cgtcactcag  83460
attgcatggg tccattccct ggggcttctg gccgcccttg cttttcctcg cctctgggtt  83520
ttctgccgat tgtgtttgtg tgattatttt tccattagag tgtcatatct ataagcctgt  83580
tgtcctggtg gacccctagg ttgggtacat gcatgacacc tctgagggcc aagaatcttt  83640
gtaaaagaga gagtgatgtg ttagaatgct agacgcctaa ggaaatgggg cttggttttt  83700
tttcaagagg ttattcttgc aaaagggaaa gggaaatttg aattgaagga gtgcttagga  83760
cctttctagc acatggaaag tgtgtttatg tgaactagca tggcttgatt gggggccact  83820
tagtggttta ttattttggg ggtataaaat atgagagtga gagaggcagg aggtaagctt  83880
acagtcatct ccatgagtgt ttttgcaaag tttgggtatc agaagtttgg gttttgcagt  83940
gcagagggtg gattggaggg gcagcgagtg gggcaagggg gccagtgaag acctagataa  84000
gagcccaggt gagagagaaa gagggtctgg agagtgggag tgtgggcagg gagaaccaga  84060
cagttttagc aggtggagtt gatgggagct cttggcccta aggcatgaag gagaagtgaa  84120
tgggaccaca tgcccctcct agcccacccc atgtcccatg ccctggattt ctagtttgtg  84180
tgggtgatgg tagcctaaac tcagaaagtt accctccagg cggggcaggc ctagatatcg  84240
agctcagttt gagattggtt taccttgagt tccttgtggg aattccaggt ggagacatca  84300
agtgggaagt tgggtagata atctgttgct cagggaaaat gccccccttgt caatatggat  84360
caggtggcca cccagggctg cagtccagct ggaccagtgc cttgtggaca gattaggcat  84420
gcctggcacc tgttccagct gtgcctcagc aggggtgttg ctgaatagtt ttccctctcc  84480
ctgggcgctg tagatagaaa acttttaaat tgatatatta catatatgca gaaaagtgtc  84540
```

-continued

```
caccataatc tacagcctga tgagttgtca tacagtgaac acacctgtgt tacccccacc  84600
caaatcatct cctcttatgc cttctcccaa gccctactcc gtccctgtcc cccaagctca  84660
ctactgtcct tacatcaacg atactaaatg ttacataagt ggggtaaaag gcacttgccc  84720
tttggcttct tttgttccac actgtgtttg tgagatccac ccatattgtg tgtcacagag  84780
gttagtcgat tttcacagct acatagtatt taatggcaca aatatttcac ggttcattca  84840
tttactgtca acagacgttt agactgtgtc caggttgggc ttatatgagt tgcctttctt  84900
gcatttgtct tttagggtag ggttatattt tgcttaacga cagagatact tctgagaagt  84960
tcatcgttag gtgattttgt tgttctgcaa acatcacaga ttttatttac acaagcctag  85020
atggtacagc ctgctacaca tttaggctct atggtatagc ccactgctcc tagactacaa  85080
acctgcacag catgttattg tactgaatac tgtaggcaat tgtaacacaa tgggaagtat  85140
ttgtgtacct aaacatggaa agggtgtggt aaaaatatga tattaatatt ataatcttat  85200
gggaccactg ttgtatatgt ggttcatcat tgaccgaaac gtcgttttgt ggcatgtggc  85260
tctacctgtg tatgcatttc gctgggtaga tacctaggag atgctgtcac aggcggtgca  85320
tgtggtcccc tgccagagag ttttgcaaaa tggttataac aaatgtcacc ctcacaagct  85380
gtttattggt ttttcagttg ctccacaaca attgtccagt attttgaatg tcaaaccttg  85440
taccagtaca tagtttaacc agaaaactag atatcctggg gcaatgtttt catccgtatc  85500
agcatctcct aagaagcttc ttaagcttgt aggggccttg accccacctt agacctcctg  85560
aatcacgatt gctaagaggg ggacagaaaa gacaaatcct agcttcagag gcctgccagg  85620
gtgggtgctg tgttggtgta tgtgtgtgtg tgcacaagag aaaaagacac aaagagagaa  85680
ggagagggga agagagagag agaatagttc tggtgatgtg gtgatgactg tgggggtcac  85740
tggctgagga agaaaaaaac tgaggccagg aaggtagaaa ctaactgaag aagctggtag  85800
gatctgaaga ctggacgcct gaatggtgct ggaaatgggg tcagtgggaa ggatggggga  85860
agtaagaggg tgggaggtca tgctcagaac ctgagctttt cagtggtgga gctgttccag  85920
gtagagacta gttagggaac aaacccaaat gcctcaggta aactttaggc aagttaaaca  85980
tgcctgctgt ttgcaggggc tgtgttgtcg tttgctgagt tgaaatttca gggatgggag  86040
tcaaataatt ataaatatgt gcaccatacg tacatgattt atgttctatt tccagtcata  86100
ttcatatggg attgttatta tagggtgctc cttaggctct caacaaaatt tagtttcaag  86160
aggacctgat tttcatgcct cttattgcca tggtgtctag cgggtagatg ctggcccacc  86220
acaagccaca ctgtaatgat ctggatgggg tgattctcag actaggaata ctcctttagt  86280
taaaaactac atgctaccct ttccctctag gatctcctag gagtatctac acttttatca  86340
tactttcacc ataatttctt taaccagtct cctgtcaatg gacatttcag ttttctatgt  86400
tttgcagttg cagacactgc tgaaaataaa atttataaat taactttggg agagttgata  86460
tctttgtgat gttgactact ggttactttt agggaagtca agttttatta ttaacaagag  86520
cagacaataa cacccattag tgtaatgtct tttagcaaag cagagacaac taggtgcttg  86580
attttacaaa aaattagtac atatgaactg tttccttaag caagattaat ttcccacttt  86640
atttacatca gcgattcact aagcaaagat tttttttagt ttgtcagctg gctcacaaac  86700
tctgatgtat gttgggatga ttaaatgaga taatgagtgt gaacatgctt taaagtatga  86760
tccaatataa ggtgttagta tttatttatt tttgagacag ggtctctctc tgttgcccag  86820
gctagagtgc agtggcacga tcttggctca ctgcaacgta tgcttccagg ttccagctat  86880
tctcatgcct cagcctcctg agtagctggg actacagtca cccgcaactg cctggctaat  86940
```

-continued

```
ttttgtattt atagtagaga tggagtttca ccatttatag tagagatggg gtttcaccag  87000
gagttcaagg ctggtcttga actcctgacc tcaagtgatc cgcctcagca tcccaaagtg  87060
ctgggattat aggcatgagc cactgcgccc ggcctaagat gttagtatta tgcacagtga  87120
ccaagacaat gctgaataag ctgccacgta cagtacaggc aggagtgaat agagtagagt  87180
aaagagggga gaattgactt ctgctgtgta agatgaagcc catctacaat ctgtgcaata  87240
gaagcagact ggatggcact gtagggtcaa ggagtctctt aagagagcca ttcttattgc  87300
ctggaagatg cctcttgaga aaatgacagg gaaggaagaa acaccttctg aatggacaag  87360
cctgcttccc aagggcaggt gacccaccag ccatgctagg tgctcacccc catgaggcca  87420
caggcaatat agcaacccca aggctctgtg gtgacacggc agccagtgca ggggctgggg  87480
acgagggatt ctgacctgca ggtgtgaggg tcagcaccac tcatcttcaa gccaagatgt  87540
tagcctgtgg ggtcttttga gcaagagcaa caccggcctg tcttctcagc ctactgttcc  87600
tgcccaaccc ctctgtctag gatggactga ggctgatttc tttttttctt tttcttcttc  87660
ttcttcttct tctccatttt gttttttttt tttttgagac agagcctcgc tcgcttaccc  87720
aggctagagt gcagtggtgt gatcttggct gactgaaacc tccgcctccc agattcaagc  87780
aattctcctg tctcagcctc cttagtagct gagactacag gcacgtgcca ctatgcctgg  87840
ctagtttttg gcatttttag tagaaacagg gtttcaccat gttggccagg cttgtcttga  87900
actcccaacc tcaggtaatc cacctgcctt ggcctcccaa agtgttggga ttacaggcat  87960
gagccaccat gcctggcctg atttctgatc attttactac tggcagggac atattaatgt  88020
ttttggaaaa aacagagcta gctcccatta gcccatcaag cactggggct ccaagctctt  88080
ctgttggctg cccatcccaa agagacccta agaataggaa ttagtgtgtt ctttctcatc  88140
ctggagctag aagaacacta cttacttccc gcctgcattt tgctttgtag ttttctttcg  88200
tggactagct agctacaagg gccaatgcca tagatagaat tcagttttga aactgtggcc  88260
aacatgacca gcctgtggtg tcctgatagc cacaagactt caaattcatt ccatttaacc  88320
tattatttat ctacatgagg ttctatgaga agtgaggaat ggtggctaca tgccagcctg  88380
gcagttatct gtgaggactt ggagaggtca ctaggttgtg atagtctcca aagtggggtg  88440
tgttcaccag tgggcggtag agatgatccc ttggactgcc accagaaaac acccatttta  88500
tatatgaatg tgtgcataga agtcaatatg tacaaataga agtttatatt tcaatataca  88560
taataagtta atttagcatt atatgaatat gtgtgtgtat acatgttcac tttatatgtc  88620
tacatgcaca tctgtgcaca catacacttt ttaaaattta actgatgggg gacccaggct  88680
aaatttttgg atacactggc ctattgaaca tctctcttta gcagagtact gagtatgagt  88740
caatttcagc actgttcatt ttcagcccaa ggtattctcc agcattctat agccactgca  88800
ctacacactg tgctgggtgc tacaggagat actaaagtga ctgaaccaca gtttctgctc  88860
tgatgagact ttaactcaac cttttatagg acttctgttg ttggtttggt agagaaatag  88920
aaaacattca cctggtgttc tttaaaaaaa tcaacataaa taacagaatg gtacttcagc  88980
tgcatattgt gttcatagaa gagaaggaag agaaggaaaa gtggggacta gaaaatgcat  89040
aaatgagtga gaatgggaaa ggcggaagca agtaaaaaga caggactgag agaagctggc  89100
agtgaaggat aaagagactg aaaatcggca tttaggttgg agggaaaaaa aacgcagaga  89160
gagaggagta tgagaggaac aggctagacc agcaggtctc aaaatgtgag aattcttgta  89220
ggtctttgaa gtctgcaagg gtaaaacttt tttctagcaa tactaagata ttagctgtct  89280
```

-continued

```
ttttaaaaac tctcattctc tcatgaaagt acagtagagt tttccagagg ctagatgatg  89340
tgtaataact catcagattg aatgcagatt atctatctat ctatctatct atctatctat  89400
ctatctatct atctatctat ctatctatca catttttcttt atccagttaa ccactgatgg  89460
actcttaggt tgattctttg gctttgcaat cgtgaatagt gctgtgataa acagacaaat  89520
gcaggtgtct ttttgatata atgatttctt ttcctttggg taaataccca gtagtgggat  89580
tgctggatca aatggtagtc ctatttttag ttctttgaga aatcttgata atgttttcca  89640
taggggttgt actaattcat attcctgcta acagtgtata aatgttccct tttctccaca  89700
gtctcactaa tatctgttat ttttgacttt ttaataatag ctattctgaa tggtatgaga  89760
tggtatctca ttgtggtttt aatttgcatt tctctgatga ttagtgatat tgagcatttt  89820
ttcctgtttg ttggctgctt gtatgtcttc ttttggaaaa tgtctgttta tgtcctttgc  89880
ctacttttta atggtttttt tttgtattaa tttgagttct ttatggattc tggatattag  89940
ctctttgttg gatgcatagt tcggtttgca aatatttttc ccattctgta ggttatgtac  90000
tctatcgatt gtttcttttg ctgtgcagaa gctttttagt tgaattaatt cccatttgtc  90060
tatttttggt tttgttgcat ttgcctttga ggacttggtc ataaattctt tgcctaggct  90120
aatgtccaga agagtttttc ctaagttttc ttctaggact ttttgagtgt caggtcttac  90180
atttaggcct ttaattcatc cttagttaat ttttgtatat ggtgagagat agggatccag  90240
tttcattctt ctgcatatag caagccagtt tttcccagca ccatttattg aatagagagt  90300
ccttttccca ttgtttattt ttgttgattt tgttgacgat cagttggttg tcagtgtgtg  90360
gctctatttc tggattctct attttgttcc attggcttgt gtgtcgattt gtgtaccagt  90420
tccatgctgg tttggttact atagccttgt agtatagttt gaagtcaggt aatgtgatgc  90480
ctctggcctt gctctttttg cttaggattg ctttggctat ttgggctctt ttgtggttcc  90540
atgtgaattt tagaatagtt ttttctaatt ctgtgaaaaa taatgctgat tctataggaa  90600
ttgcattgaa tttgtagatt gccttgggca gtatggtcac ttaaatggta ttgattcttc  90660
taatccatga gcatgagatg tttttccatt ttttgtgtca cttctgattt ctttcattag  90720
tgttttgtag ttctccttgt agaggtcttt tacttctttg gttaagtgta ttcctaggta  90780
ttttgtgtgt ttgtgtggct ataataaatg ggattgactt tttgatttag tttgcagctt  90840
gagtgttgta tagaaatgca actgattttt gtacattaat tttgtttctt gaaactttac  90900
tgaagttgtt tatcaagtct aggagtcttt tggaggaatc tttaggattt ttctaggtat  90960
aagatcatgt tatcagggaa cagagataat ttcactcttt ttttcagttt ggataccttt  91020
tgtttctttc ttttacctaa ttgctatgtt taggacttct agtactgtgc tatttaggag  91080
ctgtaagagt gaaatccttg tcttgttcta gttctgaaga ggaatgcatt ttacttttcc  91140
ccattcagta tgatgttggc tacgggtttg ttatatatgg ctcttattat tttgaggtat  91200
gttactttga tgcctagttt gttgagtttt tttttttttt atcatgaagg gatgttggat  91260
tttatcaaat gctttttcag catctattga gttgacctta tgtcttttgt ttttaatttt  91320
gtttacgtgg tgaatgacat taattgactt gcatatgttg aaccatcttg gcatccctaa  91380
aataaaactc atctgattgt gatggattat ctttttgatg tgctgttgga ttcagtttgc  91440
tagtattttg ttgaggattt ttgtatctat gttcatcaga gatattggcc tgtagttttc  91500
tttttgatg tgttcttatc agattttggt atcattatga tactggtttc atagaattat  91560
ttatggagga attcctcttc cttaattttc tggaatgatt tcagtaagat tggttctagc  91620
tctttgtaca tctgataaaa ttcaactgtg aatccgtctg gtcctgggtt cttttttttgt  91680
```

```
tgtagttgtt acattttttt gttactgatt caatttcatt actcgttatt ggtctgttca  91740
gaatttctat ttctcttgag gggttgtatg cttccagaaa tttattcatg tactctgggt  91800
tttctagtgt gtgcacttag agatgttcat agtagtctct gatgatcctt tgtgtttctg  91860
tgttatcagt tgtaatgtta cttttatcat ttctgattgt gcttatctga atcttctctt  91920
tttctttgtt agtctagcta gccgtctaac aattttgttt accttttcag agaaccaact  91980
ttgtgttttg ttgatccttt gtatgatttt tttggtttca atttaattga gatcaaatct  92040
tctctgatct ttgttattat tcttttcttc tgctagcttt gtgtttggtt tgttcttgat  92100
tttctagttc cttgaggtgt ggcattaatg gttgttaatt tgagatctgt ctttttgatt  92160
tgagcaatta atgctataag ctttcctctt agcactgctt ttgctgtatc ccagaggttt  92220
tggtatgttg tgtctgtttt cattcatttc aaaacatttt tttgatttct gccttgattt  92280
tatggtttac ccaaaagtca ttcaggagca agttgtttag tttccatgta cttctgtggt  92340
tttgagagtt tctcttggta ttgatttcta attttattcc tctgtggtct gggaagatcc  92400
taatatgatt ttgacttttt ttttttgca tttattgaga cttgctttat gggcaagcat  92460
atggtgaatt ttagagaatg ttttatgcac agatgagaaa aatgtatatt ctgtggttgt  92520
tgggtggaat gttctgtagg tgtctcttag tccatttggt caagtttata taatcaaatc  92580
gacagatcaa gctcaatgat ctgtcatcat tgacagctta ttgctgtcag tatggtattg  92640
aaagtccctc actcttttat atgactgtct atctcttttt gtaagtctaa tagtatttgt  92700
tttataaatc tgggtgctct gatgctgggt gcatatgtat ttaggatagt taaatctttt  92760
tgttgaatta gaccgtgtat cattggataa tgctattctt tgtctttttt tttttttttt  92820
ttttttactg ttgttacttt agagactgtt ttatctgata taagaagaac aactcctgct  92880
ccttttttgtt ttccatttgc atgacatatc tttttacccc cctttacttt aggctatggg  92940
tatctttaca tattaagtgg tctcttgtag gtagcagatg gttgggtctt tttaaaaaaa  93000
aatccatttt gctcatctat atcctctaag tggagcattg aggctgttta catttagggt  93060
taataatgat atgtgaggtt ttgttcctgt cagagttttg ttagctagtt gctttgtagt  93120
gtcaattgtg taattgcttt atgggatctg tgaactttct acttatgtgt gattttactg  93180
tggcaagtat tgtcctttca tttccatggt tataacttct ttaagcagtt cttatagaac  93240
tggtcaagtg gtgattaatt ccccttagtgt ttgcttgtct gggaaagact ttatttctcc  93300
ttcttttatg aggcttattt ggcaggatat aaaattcttg ggaggctttt ttttttcctt  93360
taagaaggct ataaataggc ccccaatctg ttctggcttg taagatttct actgagacgt  93420
ctcattagtc tgacaggatt tctttttata ggcgatctga cacttctctc cagatgcctt  93480
taagattttt ttctttagca ttaaacttgg atagtatgat gactatatgc cttggtgaca  93540
ttcatctttt atagtatctc ccagatattc tctgaatttc ttgcatctga atgtctacct  93600
ctatagcaag atcagggaaa ttttcctgaa ttattctctt aaatataatt gcttactttt  93660
tcttcttctc tctcaggatt acatataagt catacatttg gtccctttac ataattgcat  93720
atttctcaaa gactttattc attaaaaaat tcttttttct ttatttttgt ttgacttgtt  93780
aaaatagaaa gattggtctt caagctctga aattatcttt tctgcttggt ctagtctttc  93840
actatagtta aagtttaata tatctatttt gtctttcatg tcctaagttt ttgggggttg  93900
attttcagct ttcttttgca tctcagtgag ctttcttaca atccatattt tgaattcttt  93960
atctgtcatt tcagaatttt cattttagtt aggatccatt gctagagagc tagtaatgtt  94020
```

-continued

```
tggaggtgtc aaaacacttt gtctttttgt atagctggag cttttatgct gattccttct  94080
catctgaagg agcttgatat agtttggttc tgtgtcccac ccaaatctca tcttttaact  94140
cccataattc ccacgtgttg tgggagggat gtggtgagag atgattgaaa catggaggca  94200
ggtatttccc gtgctgttct tgtgacagta aaagggtctc acaagatctg atggttttaa  94260
aaatgggagt ttctctgcac aagctctctc tttgcctgtt gccatccatg taagatgtga  94320
cttgctcctc cttgccttct gccatgattg tgaggcctcc ccagccttgt ggaactgtaa  94380
gtccaataaa cctctttctt ttgtaaattg cccagtcttg gtatgtcttt atcagcagca  94440
tgaaattgga caaatacaga gctgttgcct cctatttttg aatttgccaa catttgaatg  94500
aaacttttaa agtttgtatt cttttttcac ttgagggtgt ggctgtagta tatattgcgt  94560
atgattgttt ggctttgttt ctgggtgctt tcagggggcc aagggtctct atgggttcct  94620
tggttatgga tatcatttgt gtggtggctt tcccagatgc tgcttgttgc agtgatatgt  94680
agggtgtatg agctgacaca ctatcttctg tagggctagg agtgtggagg tctcaggaag  94740
cttatctcat acactagcac tgtgctcttc tgacagcagg tttttttgttt gatgatgcag  94800
ttcagtctct agtccagtaa gtgacgcttg agggtaagaa gagctagctc accctcaggt  94860
catccaaaga tgagtggaag cccccttcctt gatgggggtt ctgaggtctc aggggtaggg  94920
gccagcaggg ggctgcacca gctcctcatc ctgggcagac aagaacatga tccactacct  94980
atcatgcccc tttcacagca ctcataaccc tcagttcttt taaacactgt cctttggctc  95040
ctggccactc ctgaggtctg tgagaaggct tcgattgtgg ctaccaccaa aatggcctcg  95100
ggtcagagcc tctttctcca gtccagaaca gtcagctctg tggcttgtct gtcctctgtt  95160
gcagggacat tgctactttg tgtagggagc ggtagatggg ccctgccttt tctgaaagcc  95220
caggcagtac cacctcactt tcagtgggga tgcagccact gtgaaaagtg ctagaaagcc  95280
tttcttcaat tgcacgaatg ccagcttcca gcagggaaag cctctgctgc atctgcaaca  95340
gtgaatgggt ggagtaggaa atagtcccct ctccatgtcc cttcccagct actactaccg  95400
ccccttttcag agattggtcc tgtgcctgca tttcctttgt cccaaggagc actttggtgg  95460
gctgtgctcc ccctagaaga aacctgcact gagggctaga tttctggggt tcccgcagct  95520
ccccagggtc ctgctggtcc cccatggttg ccaaagtcag agtggttgtg gggtatgttt  95580
ctgggggatc tggtgataca atatcacaaa ggctgaggtt gcttgggcag ggcagtggct  95640
cagaacaggt gcacaaccag tatggtgtcc accatctcag ttcaggcctg aggggagtgc  95700
cagcacacct gcatgagttg gtcacctggc actctattct caggaagttc ccaaatcacc  95760
actgacagca ttgcccaggg tcacgaaggc agaggggctc tcccacaatt tggtagtcag  95820
cagtttgtta caggggtgag gtgagaaggg atgcacccct atccaccctt tctgtaagac  95880
tccaggctcc ccaggggcca gtctctgcca gattcttgct gttttccttt tctctgcccc  95940
agcttcttcc tgtgggctcc ctggcagacc ttggctctct ttcctcctct ctttctccat  96000
tttaatttct aatatataaa aggtgataaa tatgatccac ataaagaaag tccttttgga  96060
atcctcaaaa tttgtaaaaa tatagaggct cttgagacca aaaagtgtga gaactgctga  96120
gctgagggat ggtcagaagc atcttccagt gagagggagc atcaggatgc agcggggtgg  96180
gcaggtctgc aaaggaagaa gggcgatgga gatcacatgt gtcaatggtg caatttgacc  96240
tcagtttgat cggacaggac ctatttccta cctcccattt taatggtttt ataggaatgt  96300
tggtgattgc cttaactgat tctgttttca atctaaataa ttaagtcacc tgttcaaagg  96360
tctgctatgc ctcttaattt caggggttgg aattttgtgg ggtaatccaa attttatctg  96420
```

-continued

```
ttctatcctg ttgtcctgtg ggcataattg tccttatgcg gtgatttttt acttcagaaa  96480
atatgtcact gttggtttga gtctataaat ttggagactc tattttttta aatttttaaa  96540
taaacttttt attttttgat aattttagat ttatggaaaa gttacacaga tagtacagag  96600
tccccatatg accctcaccc agtttcccct attgttaaca tcttacatta ccatatttgt  96660
cagaactaac aaactgatat taatatgtta ctattaacta actatatact tcatttgaat  96720
ttcaccagtt tttccaagtg tcctcttcct gttccgggat ccagtcccag agcaccacac  96780
tgcatttaat tgtctgtagc agtctctcag tctttcttta ttttttgtga ccttggcagt  96840
ctttaggtat attggccagg taacctgtag atgaccccca atctggggtc tttttttaaa  96900
ttattaaact aaggttatgg tttttggaaa gacaacaaca gagatgaagt gcccttctca  96960
tcagatcata ggagggatac agcatatcca catgacgtca ctggggatgt taaccttcat  97020
cacttggtga ctttagtgtt tgcaagtttc taggtttccc cactgtaaag atactatttt  97080
tcctcttttc ctgctttgtt ctttagaagc aagttactaa gcctagccca ccctttagga  97140
gtaaattgcg ggaattaaac tctacttcct ggagagaggg aatgtctaca gatagtaatt  97200
gaattctaat gtaagaaaga ttggtctctt ctccctcttt tattttttca ttcatttatt  97260
tatatgagta tggtgtattg tatttgtcag gcttctccag agaaagagaa caaataggat  97320
acacacacac acacacatac acacacacac atatatgaga cttattatag gagttggctt  97380
acatggttat aaaggctgag aagtctcatg acctactatc tgcaagctgg agaactagga  97440
aagctagtgg tgtaattcag tcccagactg aaggcctggt gtaagtcttc atctaattcc  97500
aaaaacccaa gaaccaggag ctctgatatt tgagaaccag agaatatgga tgtcccagct  97560
catgcagaga ataaatttgc tcttccttca cctttttgtt ttattcaagc cctcaagtga  97620
ttggatgatg cccacctcaa ctggtgaggg tgatctctac ttagtctact gattcatacg  97680
ctaatctctt ccagagacac tctcacagac acacccagaa ataatgtttt gccagctatc  97740
tgggcttccc ttaacccagt caagttaaca cataaaatta accacacagt atgaattcat  97800
gtatatttat tttatgcttt gggatatact atgccattta ttttgttgct caaattgttt  97860
cagcttccaa ctggctgtag gggccagcct tacagggtct gtgggttttt ctccccatgt  97920
gtggagacga gagatcgtag aaataaagac acaagacaaa gagacaaaag aaaagacagc  97980
tgggcctggg ggacccctac caccatgaca cagagactgg tagtggtcct gaatgtcagg  98040
ctgcactgtt atttattgga tacaagacat gggggcaggg taaagagtgt gagccatctc  98100
caatgatagg taaggtcacg tgggtcacgt gtccagtgga caggggggccc ttccctgttt  98160
ggcaaccgag gcggggagag agagagagag agaggagaca gcttatgcca ttatttctgc  98220
atatcagaga cttttaatat tttcactaat tctgctactg ctatctagaa ggcagagcca  98280
ggtgtatagg atggaacatg aaagcagacc aggagcgtga ccactgaagc acagcatcac  98340
agggagatgg ttaggcctcc agataactgc aggcaggcct gactgatgtc aggccctcca  98400
caagaggtgg tggagtagag tcttctctaa actcccctgg ggaaagggag actccctttc  98460
ctggtctgct aagtagcggg tacttttctt tggcactgac gctactgcta gaccatggtc  98520
cgcttggtaa cgggcatctt tccagacact ggcattacct ctagatcaag gagccctctg  98580
gtggccctac ccgggcataa cagaaggttc acactcttgt cttctggtca cttctcacca  98640
tgtcccttca gctcctgtct ctgtatggcc tggtttttct taggttatgg ttgtagagct  98700
aggattatta tagtattgaa ataaagagta attactacaa actaatgatt ggtgatactt  98760
```

-continued

```
atatataatc atgtctatga tctatatata tctagcataa ctcttgttat tttatatatt  98820
ttattatatg gaacagctcg tgctcggtct cttgcctcgg cacctgggtg gcttgccacc  98880
cacagctggc cactgggaac tttttcaggt tgctacttgg gcccctttca tatgccctta  98940
tccttttgtt ttttgagtat ttccttactt tatggtattg taagatattc caggcttatt  99000
ttgtattctt cttttcctgg ctttagaatc agccactttt tctggctcct ctcattggag  99060
aatggtattt agaaactaag atctgggcaa tgggtgtgct tgctgctctt gggatgtcat  99120
tgcttctagg ccttctcagt agatggagct aagtaatata tgtatatata ctaacccaca  99180
gatataaata tgtctataat tatttctata tttatccatt cgtgtatatg ttaagataaa  99240
catgatggag acccttcaaa tttgcttatg ttctttttca gcctatagac cagatataat  99300
aattagcttt tcttctcttg cagattccag agagtcctct atttcatatg tgccttccag  99360
aacatctctt gtggtattca ctacttggct tctgtgttca tgggagtcac ccctcatcat  99420
gtctgcaggc ccccaggcaa tgtgagtcag gttgttttcc ataatcactc taattggagt  99480
ttggaggaca ccggggccct gttgtcttca ggccagaaag attatgttac ggtgcagttg  99540
cagaatggtg agatctggga gctctcaagg tgtagcagga ataagaggga gaacacatcg  99600
agtttgggct atgaatacac tggcagtaag aaagagtttc cttgtgtgga tggctacata  99660
tatgaccaga acacatggaa aagcactgcg gtgacccagt ggaacctggt ctgtgaccga  99720
aaatggcttg caatgctgat ccagccccta tttatgtttg gagtcctact gggatcggtg  99780
acttttggct acttttctga caggtaaaat caaatattta ggattgttgt atcagtgtag  99840
ggtttatttt cctatctggt tttcttggga cacaaggaat tatgtttaaa acttgtcatt  99900
tttatacttc ctatctaaat acctacctct ttgctgatcc attatttagg gatgtataat  99960
gataaggata ggctctgaag acagtatacc tagatccaaa tcctggttct accacttatt 100020
aactgtggac cccaggcaaa ttgcctaact tacctgtgtt tcagaatctt tgtctatagg 100080
ctggtgataa aaaataatat cacttacttc aaaggattat tgcaaaatta atacagaaaa 100140
aaagtaccct ggacatataa tcactcaata gatacggttt attactttga atattttctt 100200
ctctttaaat agacttgctt tttaatagga gtagcctgat cctaagcagt atatctgtaa 100260
aattatgggc ttgatataac agccccttttt agtctttttg tgctgctgta acaaaatacc 100320
acagactggg taattcacaa acaatagaaa tttatttccc atagttctgg cggctgggaa 100380
gcccaagata aggtgccaac aggattgctg actgggaagg ctgttgtttg ctttcaagat 100440
ggtgccttat tgctgcatcc tttggatggg ataaatgcag tgtcctcaca tggaagaagg 100500
gatggaaggg caggagagtg ctcccttcaa ccttgagcac ttttctaagg gtgctaaggg 100560
ctctactgtc atgactttat cacctcccaa ggccatccct cttaatagtg ttgcactgga 100620
gattaagttt caacatgaat tttggaggga atactatcat tcaaagcata acctggccat 100680
atatttttaa aaatttacat taaaatgaat atgtaattct taaaataaag caaagtttat 100740
ctctgtatga acatggacca taccaaagca cagagatgaa cttatttggt ctccatagtt 100800
gtggatttta cagtcatatg gtgggcactg aggacctaaa gacaatagct tagatcagaa 100860
atccctgccc ttgaggtata ccagtctaat ggggctgata aacatgtcaa aagaaaaatt 100920
aaagggcttt gttatgggca gggccatacc tctcatagta tgtcaaaggt gctaggtatt 100980
agtgttttca ttcagcaagc tgttatacaa attatcactt ggggcttttc tgttgaaatg 101040
tgttcactgc ttgactcttg aaactcaaaa tatttgcaac tacttgtatg aaatgtacta 101100
aaatacattt gctgtatgac aaaaacggga tataaataat gcttataaca cagtcagagt 101160
```

-continued acaaaatatg ttaactgaaa ataaatttag ttcctttgtc tgaacttggt atagttatat 101220
agacatatat tgaacactta cagtcacttt gatagatgca gagatgtgtg tgtatatata 101280
tatataatat ataaataaaa aatatattag tgaaattata tatatatttc actaattata 101340
tgtacatata atataaatat attatatgta catgtaatat ataatatata tttatatatt 101400
atatatatta taatatatat attatatata atataacata tattatatat attataatat 101460
atatattata tataatataa catatattat atatattata atatatatat tatataatat 101520
aacatatata atatatatat tatatatatt tatatattta tatatattta tatatataaa 101580
tgtatataat aatatatata ttatatgtac atataatata tataaaatat atatacaaaa 101640
aatatatata atataaaata tataatatat ataaatatat ataatatata taaaatatat 101700
aatatatata aatatatatt atatataaaa tatataatat atataaatat atattatata 101760
taaatattat atataatata tatattagtg aaagcaagtt tattaagaaa gtaaaggaat 101820
aaagaagggt cactccatag gcagagcagc catgatatat attttttaaa gtccttgaga 101880
agttgcatac cattaactgg tattcatttg gatgggtagc ttgaattaaa attacttggg 101940
agctccagaa aaaccttaag ctaaaaaatt ggtttgacat ggtccctgac tcccagtgtc 102000
tgtattctct cggcggaatt tgttgaaaga gacagcctcc ttgcacctct tgtagtcttc 102060
tatacttctt gctggatgtg ccaagatggc aagtccctga ccactttttt atgtgggcca 102120
tttctcagag ttgtctatgc agccagtacc ttaaaagatg agtgctatgg cttagatatg 102180
attagtctgt tctcaccaag gctcatgttg aaatttgatc cccagtgtgg cggtgttggg 102240
aggtgaggcc tagtgggagg tgtttgggcc atgggggcaa atccctcatg aatgaattgg 102300
tgctgttctc atggcagtga gtgaatgagt tctggctgtc acaagactgg attaattctc 102360
gcaggaattg attagttcct gcaagagtgg attgttttaa agtgaggaca cccctcaggt 102420
ttctctctct ttacatgtgt ctgcttcacc tttgaccttc tctgccatgt tgtaatgtag 102480
catgaaagcc cttgcaagaa gccagtaccc ttgatcttcc cagcctgcag aactatgagc 102540
taaataaacc tcttttcttt ataaattatc cagtcttagg tgttctttta tagcaacata 102600
aaattaacta atatgatgag ataatgtccc ctctctgcca caaagagtag gcttcctaac 102660
tgcttggtac aaaaccagtg gattccccac atccagtgct cctcctctct aattcaaccc 102720
actatctgtg aagtgtcatc tggactcatt gtgggacttg gggattagag gacctgagac 102780
aaagatgctg ctgccctact gcttgctaac gaagtaagta atgaagttct ttgtctctga 102840
cccaaacatc ttgtgttttt gccagcatcc cttaaacagt acagattaac atattaactt 102900
agagtaaaat aaaattgaat attctttgta taccctcatc ttgggcctga gaggattctc 102960
ataaattatt tttcaaggtg aataagtagc tcagtgaaaa ccaaaagaca taattaaaag 103020
ggaccatgag tgagaatcaa cagaaacaac tggcagcaga agcagacttc tgcacaaaga 103080
cttcaaatac tagaattatc aggcacaaat aataaaataa ccacacttac tattttttaaa 103140 gaaatagaag acaagcttaa aaatattgat aaaaactgga cattgcatta aaactgacat 103200
aaaattgaag aatacccagg acatctagaa atacaaagtg aaataagtga ataacaaatc 103260
acctgcaaag ttttaacaac ctgtcacaca cagctacaaa aaattcatga aatggatgat 103320
aactcagaaa aagtcatcaa tattaaagct cagagagaca gagaggtggg aaatatgaga 103380
gattaaaatt tatggaggct gaaaagagaa aagttctgaa atctacttaa tattagaaac 103440
taatcaatgg tatttaccac attaacgtat tagaggacaa aattcataca atcaactcaa 103500

-continued tacatatagg aaaagcattt gatgaatttc aaaatccatt catcataaaa actaaaaata 103560
gaagaatgcc tttaacctga taaaaggttt ctacaataag gtttaccatg aatatcttac 103620
ttgtgaagtt taaaatatta atttcttttt tctttctttc tttttatgtt tagagacagg 103680
gttttgctat gttgcccagg ctgttctcaa actcctgggc tcaagcaatt ctcctgcctc 103740
agccctccca agtaggtggg attacaggca tgcaccactg cacccagctc ttaactgtga 103800
aatgttaaaa gcttttcctt tgagattagg aacagacgag gatgtatgaa acatgtcttc 103860
tacttagcat tgtactggat agtctagcca gtgctgtaag gaaaaagaga gagaaagagg 103920
tagaaggaaa ggaagcaagg aaagaataat gattggaaag gagaaataaa aagtcattat 103980
ttgtagttat tacaattttg tatgaaaaaa gtcctacata tgaattatta gaattaatga 104040
gcatttaaaa ttatatttct atataccagt aacaaatata taaattttaa aaatgtcatt 104100
gcagaaacct aaaaatatga aatataaatg gttaaatata acaaaaagtg aagaaggccc 104160
tctgtggaga caattataaa cttgaagaat caaatcatta aagtaaatag atatatcact 104220
agacaaacag attgaggctc ccttagaggt tcctggaata gacttgtgca ttcataaaca 104280
taagtataga cacataggca ttttatatta gcaggaaaag gatcaatcat taagtggtgc 104340
tgggacagat gtctagctat atagaaggaa atacaactgg attcattttc taacatttta 104400
cagtacaaca gcagttccag aaggactaaa cgtgcatatg tgaaaagcaa aactatacga 104460
ttttaggaag ataatttagg agaatatttt caggacctaa tggaagaaag ggtgattttt 104520
ctaaaacaca aaaaacattg atcatgaaag aaaaaatgga taaatttgac ttcattacag 104580
gaatttatgt ccaccaaaag acaccattaa aagaggaaag acatgaatgt gtgcacacaa 104640
gagagagaaa atatttgctt tacatataac taaattatta gtgtccagaa tagtcaaagg 104700
atttttactt acatcaatgg gaaaaagaca atccaataga aaaatgggaa aaagatttga 104760
agtcacttca tagaaaagaa aatccaaatg gctaatgaaa agttgaattg acagtgacat 104820
ataatcacac catttacttt tgaccagttg tcaaaagtca gaagtcttgt aatactaagt 104880
gttggtgagg atatggagta ataggatctc tcatcctgct ggtgtgaatg caaactgaga 104940
atccaaattg ggttaacctt gaagactgat ttggtatcat atagagttgg tgatgtgcac 105000
agccacatgc tctggggcat ataccctgag catgctcttg cacaggtcca cagaggtaca 105060
tgcataaaag tgccctcaca gcattgttcc taacagccct gcactctaaa caacccagat 105120
gtccttcaat tatctcatgg acacatgtat taaaatatat tcttacagta ggatatgtgg 105180
acatgaaaat gaatgagaca cagctacatg aaacaacata gatgaatctc ctatacataa 105240
tgtttgataa aggaagcaag tcataaaata atacatgtgg tattgtcctg ttatagaaaa 105300
tttaaaatca taatagcaaa acttacctat actgtttata agcagtaacc tgtattgttt 105360
agcattgctt ataaaagtag taaaatgaaa caaaaaacaa gagattatca ccaaaattag 105420
aaaaatgttt cctcctagaa agggcaaggg atttgtagtc acaaagagag gtgcaagaag 105480
ctatcaggag gctggcaatc atctctttct tgccttgggt tgtgatttct aggcatttga 105540
ttttttatta ttcttgaaac tgtacatatt ttatgcatgg ttatatatgt ataaaatatt 105600
ataataaaaa aagcaaagaa ataagatctg atcccaccct taaggagcta acagtggaga 105660
atatagactt ttgaactgac aatttcaatg aaatgtagta aatgcttttt tttttttttt 105720
tttttttttg agaagatgtc tagctctgtt gcccaggctg aagtgcagtg gtgcgatctt 105780
ggatcactgc aacttctgcc tcccaggttc aagtgattct cctgcctcag cctcccgagt 105840
agctgggact acaggcatgt gccgccatgc ctggctaatt tttgtatttt cagcagagta 105900

```
ggggtttcac catgttggcc aggctggtct tgaactcctg acctccagtg atctgcctgc 105960
cttggcctcc caaagtgctg ggattacagg catgagccgc catgcccagc cggtaaatgc 106020
ttttaaaata ataaaaactc gcatttatgg acaatttatt atacactagg tactattcta 106080
aatgtcttat atatcatctc atttaattat ttaaagaggt ctgtgagata gacactattg 106140
tgcccccccc tccttttttt ttaaccagta gggaaaagga agcatagaaa gttcacatgg 106200
aaaataaggg atggagctgg gatttgagcc caggccagca tccccaacta ctgcatcaca 106260
ctgtttctga atttttgcta tgagacccca aggaatgatc aatggaagtt gtcagatgga 106320
gaaggccccc aagggaaagg aatagctttg tgtcatgaaa caacctggca tgttcagaga 106380
attgtgggaa agtcagtgtg gcagaagtag agaagggcag attgtgaaag gaaatgacaa 106440
gagacaaaac cacaatgggg attattttat ttctaggaag tgtggaaggt gtactgacat 106500
gaggttagga agaccagctg ggaagctagt gggatgaatg atgtaagaaa tggtgaagac 106560
ttgagtgaaa gcgggaaaag cagggaggaa aagatgaaga catatttggg aggcatttct 106620
aaactcacat aatctgatga cgaatatgca ggagggagcg gaggaatgta ttaaggttta 106680
gaagcctaat ggaaggagat tttgctaacc aattcaggaa ataccaggga gagagcagtt 106740
ttagaagaga agggaacacg tttggatata ttccagtgag cttgtcctat ccctattaag 106800
aaaaacaaag tcctatccct atattaagaa aaacaaagtg aagatgtgtt caaagttaat 106860
accaattaca acagcaacaa gagattgcag ctctgcagga cattaaagca gagaagagca 106920
actggggcca gatggtgggt ggggagttaa tagcccatac ttaggaatca gagccaggga 106980
agtggatgaa atcacaaggg cagagtgtgc agcagaggac tttagggagt ccagctttga 107040
ggcaggcggg tcatcaggga ggtacaagca gaaccaggtg agagggatgt tttacaagcc 107100
aaaggacagc aggggtctaa cgagtaggca tggtcagtgg cattagagag gacaggcaga 107160
aaggaccagg agaggcaatg tgcaggtccc tggtgactgc aaaatgagct cagaaaagtt 107220
ggttgcacct ggtcatcatt ggctgaggaa acatgtagga gttgaggaag gaaatactcc 107280
cttctgatat atctgtcaag ggaggaaatg caacgtggct aaaggagcaa tggggtcaag 107340
agaaggttct tgtctttggt tggaggagac taaactgaaa ggaagaagtc aaaggagagg 107400
gaaaaacaaa ggaaaaagaa gtgaagggtt tcagaggaag tgggaagagg cacaagccga 107460
tacaaagatt gcaaaatgat atttggagag aaaggggcat gtgtcttcag agaggcagga 107520
agagaaggct gaatgcagat gcaggtcatg ttggtaagtg gacagagcag gaagttgtgg 107580
gtcttcctct ttgatggtct ctgttctctg caggagatgg ctgttcatct acagagagag 107640
aagttgtttg aggtgggaga gagggtcaag cagtgatagg taaaaatagt tttaggtggc 107700
attcagggat aaaattagat tggggaacat tcatatatag ggccaacaat ctctactaat 107760
gtgcaaagga gcaaagaagg ctgaagtgtg aagatgatgg tttcttattt atttgcatat 107820
cctctgctgc accaagcaaa tctgttggtt ggactctcca gacaatattc ttttgcctta 107880
aactatttgt cagagacaac ccataggaag aaaatatttg cttattatat atctgataag 107940
ggtctagtat ccagaatata taaagagctc ttacaactca atattaaaaa agcaatagac 108000
taattcaaaa atgggcaaag aatttggata aacatttctc taaagaatat atgcaaatag 108060
ccaatacgcg cttgaaaaga tgctcaacat cattaatcat tagggaattg taaataaaaa 108120
ccacaatcag atactacttc acagccattg ggctggctat aataaaaaag gcagacagta 108180
acaagtagtg gggagaatgt ggagaatcaa aaccctcata cattgctggt gggaatggaa 108240
```

-continued aaatggggcg gccatcttgg aaaccagttt ggcagttcct caaaatgtta cacatagagt 108300
taccatatga cccaggaatt tcactctagg tatataccca agagaattca aaacctaagt 108360
tcacacaaaa tcttgttcat gaatgttcag agcagcatta ttcataatag ccaagaagag 108420
gaaaatgagc catcaactga tgaatagata aaatgtggtt tatccgtata atggtgctac 108480
tcagagagaa aaaaggaatg aagtgctaat acatgctaca acgcagaaga agctggaaaa 108540
tctaatgcta gggaaaagaa gtcagacaca aaaggccaca tattgtttga ctccatttat 108600
gggaaatgtc cagaacaggc aaatctatgg agacagaagg tagatgagtg gttgtcagag 108660
actggaggga gcagggaaga gggggtggca gcttctgggc acagagtttc ttttgggagt 108720
gattaacgta tcctggaatt aaagaatgat gatggttgca caaccttgca aatatactaa 108780
aaaccaccaa attgtctact ttaaaaggtt gaattttatg gcatttgaat tatatcacaa 108840
ttttaaaatc tgtcagatat tatttgtttt ttaaacaaag agatgcctct ttcaattatg 108900
aaaagatagg gcaagtaagc acattattct agaagaagaa ggtagcaaga cctctgtttt 108960
tagaggggct tggcaagagc tgtcatagcc ttagtggaca gagccagcct ggcagggaag 109020
atgatcccac agagagccaa agtcctgaaa gggagaggac aaattctctc ctctcttccc 109080
ccaatcccag gttaaagggt cctgcgggga tgactcagag tgatcaggta tgtatattag 109140
caactcaggt aaaggcctct ccactgaaca gctggtcttt taaagaagcc atggaactta 109200
tggtttgctc aaaataaata aaagaaaaac aatcaataca taagctattc aaggtatata 109260
ggtaatgcct atcttttatg aattggagtg gatgtttaaa ctgttacaac tctacctttc 109320
ctcttccact gtgtgactct tatttttcag gctaggacgc cgggtggtct tgtgggccac 109380
aagcagtagc atgtttttgt ttggaatagc agcggcgttt gcagttgatt attacacctt 109440
catggctgct cgcttttttc ttgccatggt gagttgtgtt ttttacttct ttaattctgc 109500
tgcagttttt cataggaaac cttaactctc atcattttgc tcatttaaga tctagtgagc 109560
gagatcaagg actcatcttt gtccactcca ctgcagaagt ctgcctacag aataccaatg 109620
ccttatgttt agaatggaac tcattaaagt gaaaaattgt tgctggctag gcagaagtgt 109680
gtttgcctct gtgtcgggca tgtggtccac atgtcacaat tactgaggca ttattttctt 109740
tctgagtaat catattggtc tagtcagggc ctgttcacat gagcaaacag acagttgagg 109800
tgtgtggtta aagtcacttg tataatgtac aggaagaatg aaaacaggag ggcattaggt 109860
ccttatgtta ccaggaacgg cagtttagtg gaaagggcac gagtttgaat accagcattg 109920
tcatatattg gcttgttagt tgtatgatca gtatcctctt tgaacctttg gttgcagtct 109980
gtaaactgta gaaaagaatc tgtgtttatt attattattc tcaggattca gtgagattaa 110040
gtataaacaa ccgcagtaca gcacctgatt acaatggtaa cttactagaa atggactagc 110100
gagcaaggag gctgtttcca tgctcagtga ggcttccaga tagatttcca actatcaagc 110160
aacatcaaga ataatagagg gaagtttcca tctggaggag gagcttgtga tcttgctaaa 110220
tgcagagcag caggttggat ggtctgaggg tctggagaga agcaaagggc ttcaatctct 110280
ctgcaccccc tcagagaaca agatggggtg tcagttttgg agtctttttt gatggataga 110340
aagggtttct agcaaaccat acagttggcc aaggataagg aagatgcata aaaataaatc 110400
taggagactg gaaggtgttg tacctcatta aaaagtaaat atatatattt aggaatgtaa 110460
agagttttaa atacaagata gcaaccagta gttctgtttc cactgaggac ataactctgt 110520
gactgtagag tgagatttca cgagagaaac cttctggtgg gactgaaggc tccacaaagg 110580
cacaggtact aagaaagtat aaacatcatc ttttggaaga cttaagagga tatttctgaa 110640

-continued

```
aatatctgtt tcagtcttgc aaaataccac gcgttggctt ctatacccaa ggaaacaagg 110700
ccacacccat agaatacatc cgtgaaatgt ggccttaatt ttctgtgact gtttccgttg 110760
atgttcatgg ggaatggatt tgtgggggaa ttctgtggat gggagatgca ggcagattca 110820
tttactcaac acatttattg atctgtctac agagtgtaat gctaagtaaa ccagacccag 110880
ctgtctcagt aagtctagta ggaaaggcaa gacgttgatc agccatcttc aaaaataaat 110940
aaaatgttga cagtgagggc ataacatcag tgggtctgga gcgttcacca gggtctggag 111000
ggtcaagggt tttctcactg tgagggatgg gtgagagaag aatattccag caaagataga 111060
agtggatgaa agggccctga gatgagaaag aaaagccgga atgtctggag aatagagagg 111120
aggagagacg cattgatgag gctgaaggga tcaaggcggt taggtggggc tttgtaggat 111180
tgtcaggatt ttgctctatc tcctaaaggc aatggcaatc cacaaaaggg attccaggaa 111240
ttctggctgc tatgaggggg tggattccga gaagatgtga gtattattat cagtggaagg 111300
gatgggtgtg agtggattca cagagtgttt tggagttagt tgtatatgga ttttctgaat 111360
ccaataacag aggaagttgt agctgactca tgagaaataa ttagcattga aaaacctgac 111420
agggacaaat attacagctt aatttaactg ggaaatttat agtatttgaa agttatcaca 111480
atctttgtta atgtaacagc agcgcttacc aaaagcgact tctggattgt tagatgtagg 111540
gtcccgatga tctgagtctt gccattacaa agttgcacag ggaaataaaa gctgttgtca 111600
caaaaatatt aaactgatta tgaatacagt agtcctcatc aagcacctcc ctgcctcctg 111660
ctagtgtcaa ccctttctga cagcaggaat atccttgtag gccggcctct ttgtgactgt 111720
ccaatgcaag gagaaattgc agttattaca agggacacat gtttacaaaa agtctttaaa 111780
agcagtgagg gaacagggga acactgcctg aatcctgccc acaacctttg gccagtgggg 111840
atctggcaga gagacctgtt aacttttgaa gaaattaaca tctgcaagga taatcacata 111900
atgagccttt gaaagagtat gattcaaata tctaatgatt aagagaagcc tttggggagt 111960
ggtgctctcg aataatttta caaaagttaa ttgtatgatt tgtgttgtag aagtcaaata 112020
tgaaaaaatt ttgtagaaaa aattcttccc ctcctcctcc caaaaaaccc atcaatggac 112080
tcattctttg tttatttcaa gaatggtcac atattatatt ctaatcacat attgtaatct 112140
aatttttatt aaagatagtc atatttccaa aataaagttt ttccccagtt ttccttcttg 112200
tggtaaagta catataacac aaaatttacc atcctaacca tttttaagtg tacagttgag 112260
tgatattaag tgcattcata ctgtggtgca attatcacca ctgtgcatct tcagaactcg 112320
ttttcatctt gcaaaactga aactctgtcc attgaataat aactctctgt tccctgtctc 112380
cctagcccct gacaaccacc attctacatc ctgtctctat gagtttggcc actctaggta 112440
cctcatgaaa gcggaatcat atgatagttg tctttttgtg actggcttat ttcccttagc 112500
ataatattca ttgtatgcat agactacatt tttcttatct attcatctat ggacggaccc 112560
ttggggggtt gcttccatgc tttagctgtt gtgaataatg ctatgagcag gcatgtgcaa 112620
acatctcttc cagaccccac tttcaattcc tttgggtata tactcaaagg tggaattgct 112680
ggatcatgct gtaattgttt tttgaggaat cgtcatactg tttttcctag aggctgtgcc 112740
attatacatt tctctcacat attacacatg ggttccagtt tctctacatt cccgccaaaa 112800
cttgttattt tttttttaa ttagccacac taatgtgtat gagggggtat ctctttgtag 112860
cattgaattg catttctcaa tgattggtaa aaatttgtat ttcttctgtt tgaaatgtct 112920
gttcaaagcc tttgcccatt tttgaattgg attgtctgtg tttttgctgt tgttggattt 112980
```

-continued taggagttct ccataaaatc ccttatcaga tatttgattt gcaaatattt tatccagttc 113040
tgcaggttgc cttttccctc cattgatagt gttctttgat gcacagtttt aattttcatg 113100
aagtctaatt tgtcttcttt gcctgtcaaa atagaatttt aattaaatca gtttttctta 113160
ccactagtta gcgtaaattt ttttgtctcc atttagcagt taggatttaa caataaggac 113220
ctcctggata cagataactt gatgtatgca tttacaagga atggagaaat acatccacag 113280
tataatgaaa tatttagatg acacaaaaga caatgtctaa catttatatc ataaataatc 113340
tctcaagttt tgccatttgg ggtggggagg atgagggaag atgaaaggac ctataagaaa 113400
aaaagataga tcggattgaa tgtcatttta tacatctgat aggggtttca gaaagcaagt 113460
ctttgtcatt ttcttttttg cctatatgtg atttgcaatg gggtcagact cctcaatagt 113520
tataaatgtg accttgaata taaatcccta ttatttgttt ttcaggttgc aagtggctat 113580
cttgtggtgg ggtttgtcta tgtgatggaa ttcattggca tgaagtctcg gacatgggcg 113640
tctgtccatt tgcattcctt ttttgcagtt ggaaccctgc tggtggcttt gacaggatac 113700
ttggtcagga cctggtggct ttaccagatg atcctctcca cagtgactgt cccctttatc 113760
ctgtgctgtt gggtgctccc agagacacct ttttggcttc tctcagaggg acgatatgaa 113820
gaagcacaaa aaatagttga catcatggcc aagtggaaca gggcaagctc ctgtaaactg 113880
tcagaacttt tatcactgga cctacaaggt cctgttagta atagccccac tgaagttcag 113940
aagcacaacc tatcatatct gttttataac tggagcatta cgaaaaggac acttaccgtt 114000
tggctaatct ggttcactgg aagtttggga ttctactcgt tttccttgaa ttctgttaac 114060
ttaggaggca atgaatactt aaacctcttc ctcctgggta agtagttaca gtatatttaa 114120
atttggcagt gaagtgagat ttctaccatt tgtgtgtgtg tgtctgtttc tgtgtgaatt 114180
tgagaaaaag aatgttttta ataggccctt taaaaccagg aacaatactg ccaaccatat 114240
tattatgata tctcttagtg ttatgttgta acacatgtac atatgagggg acttcaacca 114300
gttcatggaa aaatggcatt aaaagacaaa aatttaaaac ataaactttc tcaacatgat 114360
tgccatcaag gtcaagacac ttttgtacga catcagccat ttattccatc cttaaaaaac 114420
tgagggtcct gagaatgtac ccatgtcaat gcagtcttat ttacactatt aactgaagaa 114480
aaatgggtgc cgcgtacaga ctttttaaga ttaggaaaca gaaagaagtc agaatgagcc 114540
accatgagaa ctgttaaggt ggctgcctag tgatttccca tcaaaactct tgcaaaattg 114600
cccttgtttg atgagaggaa tgagcatgcc cattgtcatg gaggagaagg actctctggt 114660
gatgtttccc aggcattttt ctacaaaagc tttggttaac tctctcaaaa cactctcctc 114720
ataagcagat attttcattc tttggccctc cagaaagcta acaagcaaaa tgccttgagc 114780
atccccaaca aacgttgcca tgacctttgc tttcgactgg tccacttttg ctttgacagg 114840
accatggccc cccttggtaa ccattgcttt ggttgggctt tgtcttcagg atcagactcg 114900
taaaaccgtg tttcatctcc tgttacaatt ctccaaagaa atccttcagg atcttgatcc 114960
cacttgttta aaatttccat gggaagttct gcccttctct gcagctgatc tgggcacaac 115020
tgttttggca cccattgagt ggaaagtttg ctcaacttta atttttcagt cagaattctg 115080
taagccagac taattgagat atctatggta ttggctattg cttctgctgt taatctcagt 115140
ctttgtcaat tagggcataa acaagatgta tttttttcct caatgtggat gctctgccac 115200
tgtggtcttc atcttcaata tcgtcttgtc ctttcttaaa ataagttatc catttgtaaa 115260
ctgctgattt atttggggct ttgtgcccgt aaacttttca taaagcatca atgatttcac 115320
cattcttcca cccaagcttc accataaatt tgatgtttgt tcttgcttca atttcagcag 115380

-continued

```
aattcatgtt gctctagtgg gagctctttt caaactgata tcttattctt cttagtgcct 115440
caaactagct cctcttcaga cacgttctaa gaagttagta caaatttctt ttagtgcaga 115500
aaaaatctga aaacacatgc atagtttttt cataatatgc actttccatt aacttttttt 115560
tttggaaaag gagtcttgct ctgttgccca ggttggagtg cagtggtgtg atctcagctc 115620
actgcaatat ccgcctcctg ggttcaagcg attctcctgt ttcagcctcc tgaataaatg 115680
atattacggg cacatgccac catgcccagc taatttttat attttagtag agacagggtt 115740
tcaccatgtt ggccaggctg gtctcgaact cctgacctca ggtgatccac ccgccttggc 115800
ctcccagagt gctgggatta caggcatgag ccacagcacc ccgccgtcca tgaccttttt 115860
gaaaactcct tgtattttcc atttgaaaaa aatgcatcag aagaatttag tctctccctt 115920
tctgccttct ctccttgctc accttcttca cacccatccc cagcccagag ctcctcccag 115980
gggtaacttc tataatgttt gggttgtgcc ctttcagatc tattcctatg catttgtgcc 116040
agacattgtg gcatgtgcct gtagtcccag ctactcggga ggctgaggag ggaggattac 116100
ttgagcccag gagttctggg ctgcagtact ctatgctgat caggtgtcca cactaagttc 116160
agtatcagta tggtgacctc ctgagagcag ggaaccacca ggttgcctaa ggaggggtga 116220
accggccctg gtcgaaaatg gagcaggtca aaattcctgt gctgatcaga tctgtttcta 116280
cgcattttca tatatttgtg catattaatg ttttatattt taacataaat gagatcactc 116340
actatatatt gttctttgta agttgcttcc cttttaaaat ttaatatgcc ttggctatct 116400
ggcacctctc aaccttcaag tgtccttaat ttataaattt tagttagtaa aataactttt 116460
aaatacatgc aactataatt tatgttgttg tacttctttc attttaatgg caggttaaat 116520
cactttagat agcttgagat gtgactccta gtgtaaacca aatttaaact aaaacgtgag 116580
agaaatatta gaaacctctt tttatccatc tagtcttaac tcctgcttat tgctgtgtag 116640
gctgcctgta ttttatatta tcctcaaaac atcttgcttc taaattttta tacgtagaca 116700
tcgtgccatc tcattaaagt gctctgacgg cacatctggt tattttttct gatttcctca 116760
gcagacacat ccgtttttgt tcattatagc tcagcaggaa ttatgagaga agtcgtttta 116820
agaaaaaaag atttactctt ttttttgaag caaactaaca agtttataga aagagcctgt 116880
cttgacttca aactcattct ctatgacaat ttgagatggt gcagtatccc tagaacagag 116940
tggccaatgg taggtggggt ggagtgtgga tgcagaagct taggaaggct agaagtttag 117000
atcttcatga catagttttt tacttttgcc aaagacataa attgtcaaaa aactgggcaa 117060
tctcataaat acaaaaatgt ttccaaagac aaacacacat ggttttatat tatctaccgt 117120
tttggatttt tcacttgtac tcttgcagat gggtgcttct gttcaataat tctcggctgt 117180
gaaatttttg aacaagtttt tatctcctga gacagtttgg ggctggtggg aatttgggct 117240
ctggctttgt gccatttgca ggtgccaggc ggattatgag cattagagca tttcacagga 117300
aacgctcatc tttactgtag tgagtttaaa agtggcgggg ctggctgcct cgcagcaatt 117360
cttagagagt ttctaaaggc cccagaagtg aggagagggc tgctcatgcc ttttgggtag 117420
tgggttagaa gacgggggtc cccttttgca gtcgggtacc tagacttata gagggctgct 117480
tgctcaatga caggtgtagt ggaaattccc gcctacacct tcgtgtgcat cgccatggac 117540
aaggtcggga ggagaacagt cctggcctac tctcttttct gcagtgcact ggcctgtggt 117600
gtcgttatgg tgatccccca ggtgagttat cttctgtttt ttataagaca gttatactgt 117660
gacagtttga tgggaagaat ttagcttatt acagttaagt atgaaggtca attcagagta 117720
```

-continued tgatttgggc agagtatata atatttaaaa atctgttttc tttaaaacat tctttttctg 117780
ttatataagt aatatatgtt cattttagaa aatttgaaga gaaaaatgta aaaaaaaaag 117840
aaaagcctaa cctgggtgca atgactcaca cttataatcc cagcaactca agaggctgag 117900
ggtaggagga tggcttgagt tcaggagttc gaggctgcag tgagctctga tcactgccac 117960
tgtactccag cctagatgac agagtgagaa ctcatctcaa aaaataaaaa ataaaaaata 118020
aaaagttcat aatcctaatt cccagagatg accagtgttg tattttgtaa acgcaataat 118080
cttgtgtgag gaaagtcgat cacaccttcc agcatcatca tactgaacat tcactcattt 118140
attcattcag caaacattta tccaccatct tttatgtgcc aggtgctgag aacacacagt 118200
gcatcaagtt tccgtaaatg taacgagagg gcgtctggca cccgtgtgta ctcttttgtc 118260
tagggtggtc gaggatggtg cacctctcgg aggaggcgac atgtaatcag aaacctgaat 118320
gagggaggca gccatggaga catctgaagg atatgagtca gatattcaag actggtagag 118380
tttcagtaca ctgtttttca ttgcaggaga ttagtagttt ccaatgtctg gtacgcataa 118440
acaccccaag gagcttgttt ttaaaaacag tttcttagtg agaaacacta cccagaaatt 118500
cctgaaatga ctttcacatt cccatatttt ggcaaactgc gtccctcaaa atacctcttg 118560
catccagaag tgcttcccct cttcccaaaa aagatgtttt cagatctgta ttttaattct 118620
tgatttgcaa aatgtcacta taacagtact taaaatattt tatttaatgt tctcctgtga 118680
ttatataatc attaagcaat agtatatcaa catttagagc aaagcatttt aagttttgca 118740
tatcgtttga aatttaattt aagctaacaa gtgtcttcct tttatagtag cactttactt 118800
aatgcttagg atcggtgagc caaatatttt atgtaatgaa atttccaggt gattgataca 118860
caactaattg aatgcaataa aactactcgg gacaaggagg tctctgccaa tttgagagaa 118920
cttcatccac acctttaaaa aagtagtttg tagtgatggt agttgagtag atggcagctg 118980
cctttaagtt ggtgaagagt tggggaacac cagaaccttt gagttctaca ctaataggga 119040
agatgagaaa gaggctgatg gagatttcta gaaatagagc attaacccac aacgacaaat 119100
ctctcccctc caataaattt ttccccaggt gataatgtca acacaataca aatactaatt 119160
taattaacaa ttgttaatta atttaattta caattgtaat taaggtgaca ttagctcttt 119220
aatagaggca tcccagaatc tcagtgactt aacataaagg atgtttgtta cctgctcata 119280
gaaagttcca tgtatttgta cctagctggc caaagtggga gtggtgagtg ggtgtttgtg 119340
tccatggagt cattcaggga tgtaggctga cagaggcact gctgtcctta acacatcagc 119400
cgcaaggcca ccctgggtct cagcatccag ttggcagatg ggggaggagg gagatttcgg 119460
aatatagggt gtctttgtta gttacctttg gaagtggaac acattaggga gaataaaaac 119520
cgaggtggag gtaaaggttt tgccattgag gaatgtatca gctgcaaaca aacaaacaaa 119580
tgaacaaaac agtctgtact aatagttacc actttcaaat attttctgaa gataatttat 119640
aagccaggga ttactgccac aaagggcaca atttgttttg tttgtttttt ttaagaaaag 119700
taaatagatt aaatagagac aagatctcac tctgtcaccc aagctgaagt gcagtggtgt 119760
gattatagcc ctccgtaatc ttgaactcct gggcttaaat gatcctcctg ccttagcttc 119820
tccagtagct gggaccacag gcatgtacca tcacacacag ctaatttttt tgtttttctg 119880
tagaaatggg gtcttgctat gttgccctgg ctggtctaaa actcttggcc tcaagtgatt 119940
ctcctgcctc agcctcctaa agtgctggga ttacaggtgt gagccattag gcccggctca 120000
caatttgttt gtatggctcc ttgattcatt ctgctggatc agtcccagaa ggagtgggga 120060
aattcttggt gccaccagca ctatcagggc gtgtctcctt ccaaaacagt cttcccaact 120120

-continued

```
ggctttcgtc acagttcaaa ccctccaaag tggatgggga gaagagacac actgaaactt 120180
tcctccacat ttcgtaaaga tggaaagctt tctcagactg tgagtagagt ttaatacatt 120240
caaacagaaa aataagggtc ttcattgttc tgaaaaaata ctgaaggaat tagaatgttt 120300
taagtaatga ttttaaagat tttctatttt cctttaaaaa taccacttgt gatgatctat 120360
tctgctaaat ttttttcaga aacattatat tttgggtgtg gtgacagcta tggttggaaa 120420
atttgccatc ggggcagcat ttggcctcat ttatctttat acagctgagc tgtatccaac 120480
cattgtaagg taaggatgaa ttgttttctg gttgttttcc tattatcttt cacttgtgtg 120540
tcatttcatt gtatttggcc tttacatgta aatgcttctt ttttatagaa gttacctgga 120600
tctctgagat gggaaaatga catgctgata ctcattttga gtctgaggct ttgtacccta 120660
ttagtgagga tattagacga attattttga aataacactc tattattcca aaaacatttt 120720
aagtttcaag taccatagac ttccactgag tctctgtatt gactcaaagg taatttctca 120780
ggatgtgtct ctcgatgttc tgatgccaat tgtgttagtc tgagtgggct gctgtaacaa 120840
aataccacag gctgggtggc ttaaacaata gaaatttatt ttctcacagt actggaggct 120900
ggaagtccaa gaacaaggtg tcggcaggtt tggattctcc tgaggcctcg ctctgtggtc 120960
ttcaggtggt gccctcttgc tatgtcctca aggggtctta cctctgtgtg caccgctgat 121020
gtccctccct cttcatataa gacaccagcc atattggatt acggcctcac cctaacagcc 121080
tcattttaac ttaatcacct ctttaaagac cttatctaca aataccatta catcataaag 121140
tactagggat tcagacttca acacttgaac tttgggaggg acaacttagc ccataacatc 121200
agtaatcatt ggctccctga gattacctta tctggaggtt ctcaaagctg gcagctcgtc 121260
agagtcattg aggtatttca taaaaaatat cagtcttggg tccttacacc agacctgctg 121320
gatcaatcca agaatgacac tggggatttt tttttctttt ttcgagatgg agtctcattc 121380
tgttgcccag gctggagtgc agtggtgtga tcttggttca ctgcaagctc cgcctcctgg 121440
gttcaagcaa ttctcttgcc tcagcctcca gagtagctgg gattacacgt gcatgccact 121500
acacccggct aatttttgta tttttagtag agacggggtt tcaccatgtt ggtcaggctg 121560
gtctcgaact cctgacctcg tgatccgcca gccttggcct cccaaagtgt tgggattaca 121620
ggcatgagcc accacgccta gccgagactc gggattttta acaagtctgc aggtgactct 121680
gagttgccac cctgcccgcc ccacccgccc ccccgacacc ctttgggaat gtctgatgtg 121740
attcccactg atctgggaac ctcagggact tccaagcttt tacaaagctt ttccaaacac 121800
attttacttg gaaactcttt atgtggtgaa gaggacggag gtcctttgtg gaagctctgt 121860
tgagtacctg gaatcccccc agtgctcctg ccttcttgct ccagggggct gcagcagaac 121920
ttccaggcct taacagtaca tcctttgtaa accacacttc ttgttgcagc cctcatgtcc 121980
agataagaca gctgagacca gggagatcaa gtacctggtg caagacacac agctgggacc 122040
ccagctataa agggaaggga tcttttctct gattctccat tggattttat tttattttt 122100
ttgagacaga gtctcactct gttgcccagg ctggagtgaa atggtgtgat cttggctcac 122160
tgcaacctta cctcccaggt tcaggtgatt ctcctgcctc agcctcctga gtagctggga 122220
ttgcaggtgt gcaccaccat gcccggctaa tttttgtatt ttagtagaga cagggtttca 122280
ccatgttggc caggctggtc tcaaactcct gacctcaagt gatccaccct ccttggcctc 122340
ccaaagcgct aggattacag gtgtgagcca ctgcgtccgg cccgtcagac tttttgactc 122400
ttttttttgc aaaatgatcc tgtattttaa agtgtaaata gtgattaggg tcacactgct 122460
```

-continued gccaagagac acttgtccca cagatctccc tctgtgaaat tccgtaatag tttcctatct 122520
gcagtcctcc cttaaatcct ccaagtggca ttttcctaac acctgcttta tcaatggaag 122580
ttttcatttt ctaagggaaa aaatttgtta gcttggataa tttcttagcc tattaaagac 122640
ccaatcttaa tggcaacaaa taaacaaaca agatattaag gtttttcaca ggaaacttat 122700
taaaaaatct aactgcttag ctagtgggtt catcccattt aggagtatgt tatttgtcat 122760
gtgttacaag tgtgaaaggc aagtgacttt ctatagagat aagtccatat aacaccagcc 122820
cagagatgcc tcctccttgt ctccacaagc aggagggatg taggacctag aaaatccatt 122880
agtcaagaga tagcataaat ccttccctag gaattttcca tgcccacaca cctgcctgct 122940
gaaatgctag ggcaggcagc cctgtggacc aggatgggta agtacatttg tgttgactgt 123000
agatagatta atggatatct agatggatgg atggatggat ggagggatgg aagaatggat 123060
agatagagta ggtacacata tatatctaag aaaaaagttt atcagactaa tatgtgacca 123120
ggggtataga atagcagagg aataactccc tatgtaattg tctattagcc cagttgtctg 123180
agagtagagt ttttcttctt cctccatact tcccctctag gtcacccaga gtgctattat 123240
tagaccactc tcgcagtcta ataataaata catcttctgt ccattttaca ggttgtggaa 123300
ctggaattca cacaagatta gggtcgtggc caaaggcatc tggctagtca gtgacccatc 123360
agaactcaaa tccacatctt ttggccctat ctgtcaccca gtgaaataca tgagaatttt 123420
tatgggagac agtgcttaac attagcgggg gataagttgc tagcagtaga gctttagtag 123480
cagaggggaa gaaggtattt tggggtaagg gctttgtgga ctcttctcag atcatattgt 123540
gaaagtggca gccctgcaca gatgtacagt agcagacagg cagaataaca gattacattc 123600
tagcacttac aggctgacaa tggtggagac tagttgaatg caatagagag tgaagttgca 123660
taattgccaa cttgcgttgt ggctttggct ccgttgtggc tgacccaggg aagaagctgc 123720
tctaaatcag ggagaatatc tttgtcatgt cctgtgggac ccttctggcc tctcaggtgg 123780
atttctgctc agccaggaaa agctt 123805

<210> SEQ ID NO 4
<211> LENGTH: 551
<212> TYPE: PRT
<213> ORGANISM: Homo sapiens

<400> SEQUENCE: 4

Met Arg Asp Tyr Asp Glu Val Ile Ala Phe Leu Gly Glu Trp Gly Pro
1               5                   10                  15

Phe Gln Arg Leu Ile Phe Phe Leu Leu Ser Ala Ser Ile Ile Pro Asn
            20                  25                  30

Gly Phe Asn Gly Met Ser Val Val Phe Leu Ala Gly Thr Pro Glu His
        35                  40                  45

Arg Cys Arg Val Pro Asp Ala Ala Asn Leu Ser Ser Ala Trp Arg Asn
    50                  55                  60

Asn Ser Val Pro Leu Arg Leu Arg Asp Gly Arg Glu Val Pro His Ser
65                  70                  75                  80

Cys Ser Arg Tyr Arg Leu Ala Thr Ile Ala Asn Phe Ser Ala Leu Gly
                85                  90                  95

Leu Glu Pro Gly Arg Asp Val Asp Leu Gly Gln Leu Glu Gln Glu Ser
            100                 105                 110

Cys Leu Asp Gly Trp Glu Phe Ser Gln Asp Val Tyr Leu Ser Thr Val
        115                 120                 125

Val Thr Glu Trp Asn Leu Val Cys Glu Asp Asn Trp Lys Val Pro Leu

-continued

```
    130                 135                 140

Thr Thr Ser Leu Phe Phe Val Gly Val Leu Leu Gly Ser Phe Val Ser
145                 150                 155                 160

Gly Gln Leu Ser Asp Arg Phe Gly Arg Lys Asn Val Leu Phe Ala Thr
                165                 170                 175

Met Ala Val Gln Thr Gly Phe Ser Phe Leu Gln Ile Phe Ser Ile Ser
            180                 185                 190

Trp Glu Met Phe Thr Val Leu Phe Val Ile Val Gly Met Gly Gln Ile
        195                 200                 205

Ser Asn Tyr Val Val Ala Phe Ile Leu Gly Thr Glu Ile Leu Gly Lys
    210                 215                 220

Ser Val Arg Ile Ile Phe Ser Thr Leu Gly Val Cys Thr Phe Phe Ala
225                 230                 235                 240

Val Gly Tyr Met Leu Leu Pro Leu Phe Ala Tyr Phe Ile Arg Asp Trp
                245                 250                 255

Arg Met Leu Leu Leu Ala Leu Thr Val Pro Gly Val Leu Cys Val Pro
            260                 265                 270

Leu Trp Trp Phe Ile Pro Glu Ser Pro Arg Trp Leu Ile Ser Gln Arg
        275                 280                 285

Arg Phe Arg Glu Ala Glu Asp Ile Ile Gln Lys Ala Ala Lys Met Asn
    290                 295                 300

Asn Ile Ala Val Pro Ala Val Ile Phe Asp Ser Val Glu Glu Leu Asn
305                 310                 315                 320

Pro Leu Lys Gln Gln Lys Ala Phe Ile Leu Asp Leu Phe Arg Thr Arg
                325                 330                 335

Asn Ile Ala Ile Met Thr Ile Met Ser Leu Leu Leu Trp Met Leu Thr
            340                 345                 350

Ser Val Gly Tyr Phe Ala Leu Ser Leu Asp Ala Pro Asn Leu His Gly
        355                 360                 365

Asp Ala Tyr Leu Asn Cys Phe Leu Ser Ala Leu Ile Glu Ile Pro Ala
    370                 375                 380

Tyr Ile Thr Ala Trp Leu Leu Leu Arg Thr Leu Pro Arg Arg Tyr Ile
385                 390                 395                 400

Ile Ala Ala Val Leu Phe Trp Gly Gly Gly Val Leu Leu Phe Ile Gln
                405                 410                 415

Leu Val Pro Val Asp Tyr Tyr Phe Leu Ser Ile Gly Leu Val Met Leu
            420                 425                 430

Gly Lys Phe Gly Ile Thr Ser Ala Phe Ser Met Leu Tyr Val Phe Thr
        435                 440                 445

Ala Glu Leu Tyr Pro Thr Leu Val Arg Asn Met Ala Val Gly Val Thr
    450                 455                 460

Ser Thr Ala Ser Arg Val Gly Ser Ile Ile Ala Pro Tyr Phe Val Tyr
465                 470                 475                 480

Leu Gly Ala Tyr Asn Arg Met Leu Pro Tyr Ile Val Met Gly Ser Leu
                485                 490                 495

Thr Val Leu Ile Gly Ile Leu Thr Leu Phe Phe Pro Glu Ser Leu Gly
            500                 505                 510

Met Thr Leu Pro Glu Thr Leu Glu Gln Met Gln Lys Val Lys Trp Phe
        515                 520                 525

Arg Ser Gly Lys Lys Thr Arg Asp Ser Met Glu Thr Glu Glu Asn Pro
    530                 535                 540

Lys Val Leu Ile Thr Ala Phe
545                 550
```

-continued

<210> SEQ ID NO 5
<211> LENGTH: 551
<212> TYPE: PRT
<213> ORGANISM: Homo sapiens

<400> SEQUENCE: 5

```
Met Ala Gln Phe Val Gln Val Leu Ala Glu Ile Gly Asp Phe Gly Arg
1               5                   10                  15

Phe Gln Ile Gln Leu Leu Ile Leu Leu Cys Val Leu Asn Phe Leu Ser
            20                  25                  30

Pro Phe Tyr Phe Phe Ala His Val Phe Met Val Leu Asp Glu Pro His
        35                  40                  45

His Cys Ala Val Ala Trp Val Lys Asn His Thr Phe Asn Leu Ser Ala
    50                  55                  60

Ala Glu Gln Leu Val Leu Ser Val Pro Leu Asp Thr Ala Gly His Pro
65                  70                  75                  80

Glu Pro Cys Leu Met Phe Arg Pro Pro Pro Ala Asn Ala Ser Leu Gln
                85                  90                  95

Asp Ile Leu Ser His Arg Phe Asn Glu Thr Gln Pro Cys Asp Met Gly
            100                 105                 110

Trp Glu Tyr Pro Glu Asn Arg Leu Pro Ser Leu Lys Asn Glu Phe Asn
        115                 120                 125

Leu Val Cys Asp Arg Lys His Leu Lys Asp Thr Thr Gln Ser Val Phe
    130                 135                 140

Met Gly Gly Leu Leu Val Gly Thr Leu Met Phe Gly Pro Leu Cys Asp
145                 150                 155                 160

Arg Ile Gly Arg Lys Ala Thr Ile Leu Ala Gln Leu Leu Leu Phe Thr
                165                 170                 175

Leu Ile Gly Leu Ala Thr Ala Phe Val Pro Ser Phe Glu Leu Tyr Met
            180                 185                 190

Ala Leu Arg Phe Ala Val Ala Thr Ala Val Ala Gly Leu Ser Phe Ser
        195                 200                 205

Asn Val Thr Leu Leu Thr Glu Trp Val Gly Pro Ser Trp Arg Thr Gln
    210                 215                 220

Ala Val Val Leu Ala Gln Cys Asn Phe Ser Leu Gly Gln Met Val Leu
225                 230                 235                 240

Ala Gly Leu Ala Tyr Gly Phe Arg Asn Trp Arg Leu Leu Gln Ile Thr
                245                 250                 255

Gly Thr Ala Pro Gly Leu Leu Leu Phe Phe Tyr Phe Trp Ala Leu Pro
            260                 265                 270

Glu Ser Ala Arg Trp Leu Leu Thr Arg Gly Arg Met Asp Glu Ala Ile
        275                 280                 285

Gln Leu Ile Gln Lys Ala Ala Ser Val Asn Arg Arg Lys Leu Ser Pro
    290                 295                 300

Glu Leu Met Asn Gln Leu Val Pro Glu Lys Thr Gly Pro Ser Gly Asn
305                 310                 315                 320

Ala Leu Asp Leu Phe Arg His Pro Gln Leu Arg Lys Val Thr Leu Ile
                325                 330                 335

Ile Phe Cys Val Trp Phe Val Asp Ser Leu Gly Tyr Tyr Gly Leu Ser
            340                 345                 350

Leu Gln Val Gly Asp Phe Gly Leu Asp Val Tyr Leu Thr Gln Leu Ile
        355                 360                 365

Phe Gly Ala Val Glu Val Pro Ala Arg Cys Ser Ser Ile Phe Met Met
```

```
    370                 375                 380

Gln Arg Phe Gly Arg Lys Trp Ser Gln Leu Gly Thr Leu Val Leu Gly
385                 390                 395                 400

Gly Leu Met Cys Ile Ile Ile Ile Phe Ile Pro Ala Asp Leu Pro Val
                405                 410                 415

Val Val Thr Met Leu Ala Val Val Gly Lys Met Ala Thr Ala Ala Ala
            420                 425                 430

Phe Thr Ile Ser Tyr Val Tyr Ser Ala Glu Leu Phe Pro Thr Ile Leu
        435                 440                 445

Arg Gln Thr Gly Met Gly Leu Val Gly Ile Phe Ser Arg Ile Gly Gly
    450                 455                 460

Ile Leu Thr Pro Leu Val Ile Leu Leu Gly Glu Tyr His Ala Ala Leu
465                 470                 475                 480

Pro Met Leu Ile Tyr Gly Ser Leu Pro Ile Val Ala Gly Leu Leu Cys
                485                 490                 495

Thr Leu Leu Pro Glu Thr His Gly Gln Gly Leu Lys Asp Thr Leu Gln
            500                 505                 510

Asp Leu Glu Leu Gly Pro His Pro Arg Ser Pro Lys Ser Val Pro Ser
        515                 520                 525

Glu Lys Glu Thr Glu Ala Lys Gly Arg Thr Ser Ser Pro Gly Val Ala
    530                 535                 540

Phe Val Ser Ser Thr Tyr Phe
545                 550

<210> SEQ ID NO 6
<211> LENGTH: 557
<212> TYPE: PRT
<213> ORGANISM: Homo sapiens

<400> SEQUENCE: 6

Met Arg Asp Tyr Asp Glu Val Thr Ala Phe Leu Gly Glu Trp Gly Pro
1               5                   10                  15

Phe Gln Arg Leu Ile Phe Phe Leu Leu Ser Ala Ser Ile Ile Pro Asn
            20                  25                  30

Gly Phe Thr Gly Leu Ser Ser Val Phe Leu Ile Ala Thr Pro Glu His
        35                  40                  45

Arg Cys Arg Val Pro Asp Ala Ala Asn Leu Ser Ser Ala Trp Arg Asn
    50                  55                  60

His Thr Val Pro Leu Arg Leu Arg Asp Gly Arg Glu Val Pro His Ser
65                  70                  75                  80

Cys Arg Arg Tyr Arg Leu Ala Thr Ile Ala Asn Phe Ser Ala Leu Gly
                85                  90                  95

Leu Glu Pro Gly Arg Asp Val Asp Leu Gly Gln Leu Glu Gln Glu Ser
            100                 105                 110

Cys Leu Asp Gly Trp Glu Phe Ser Gln Asp Val Tyr Leu Ser Thr Ile
        115                 120                 125

Val Thr Glu Trp Asn Leu Val Cys Glu Asp Asp Trp Lys Ala Pro Leu
    130                 135                 140

Thr Ile Ser Leu Phe Phe Val Gly Val Leu Leu Gly Ser Phe Ile Ser
145                 150                 155                 160

Gly Gln Leu Ser Asp Arg Phe Gly Arg Lys Asn Val Leu Phe Val Thr
                165                 170                 175

Met Gly Met Gln Thr Gly Phe Ser Phe Leu Gln Ile Phe Ser Lys Asn
            180                 185                 190
```

-continued

```
Phe Glu Met Phe Val Val Leu Phe Val Leu Val Gly Met Gly Gln Ile
        195                 200                 205

Ser Asn Tyr Val Ala Ala Phe Val Leu Gly Thr Glu Ile Leu Gly Lys
    210                 215                 220

Ser Val Arg Ile Ile Phe Ser Thr Leu Gly Val Cys Ile Phe Tyr Ala
225                 230                 235                 240

Phe Gly Tyr Met Val Leu Pro Leu Phe Ala Tyr Phe Ile Arg Asp Trp
                245                 250                 255

Arg Met Leu Leu Val Ala Leu Thr Met Pro Gly Val Leu Cys Val Ala
            260                 265                 270

Leu Trp Trp Phe Ile Pro Glu Ser Pro Arg Trp Leu Ile Ser Gln Gly
        275                 280                 285

Arg Phe Glu Glu Ala Glu Val Ile Ile Arg Lys Ala Ala Lys Ala Asn
    290                 295                 300

Gly Ile Val Val Pro Ser Thr Ile Phe Asp Pro Ser Glu Leu Gln Asp
305                 310                 315                 320

Leu Ser Ser Lys Lys Gln Gln Ser His Asn Ile Leu Asp Leu Leu Arg
                325                 330                 335

Thr Trp Asn Ile Arg Met Val Thr Ile Met Ser Ile Met Leu Trp Met
            340                 345                 350

Thr Ile Ser Val Gly Tyr Phe Gly Leu Ser Leu Asp Thr Pro Asn Leu
        355                 360                 365

His Gly Asp Ile Phe Val Asn Cys Phe Leu Ser Ala Met Val Glu Val
    370                 375                 380

Pro Ala Tyr Val Leu Ala Trp Leu Leu Leu Gln Tyr Leu Pro Arg Arg
385                 390                 395                 400

Tyr Ser Met Ala Thr Ala Leu Phe Leu Gly Gly Ser Val Leu Leu Phe
                405                 410                 415

Met Gln Leu Val Pro Pro Asp Leu Tyr Tyr Leu Ala Thr Val Leu Val
            420                 425                 430

Met Val Gly Lys Phe Gly Val Thr Ala Ala Phe Ser Met Val Tyr Val
        435                 440                 445

Tyr Thr Ala Glu Leu Tyr Pro Thr Val Val Arg Asn Met Gly Val Gly
    450                 455                 460

Val Ser Ser Thr Ala Ser Arg Leu Gly Ser Ile Leu Ser Pro Tyr Phe
465                 470                 475                 480

Val Tyr Leu Gly Ala Tyr Asp Arg Phe Leu Pro Tyr Ile Leu Met Gly
                485                 490                 495

Ser Leu Thr Ile Leu Thr Ala Ile Leu Thr Leu Phe Leu Pro Glu Ser
            500                 505                 510

Phe Gly Thr Pro Leu Pro Asp Thr Ile Asp Gln Met Leu Arg Val Lys
        515                 520                 525

Gly Met Lys His Arg Lys Thr Pro Ser His Thr Arg Met Leu Lys Asp
    530                 535                 540

Gly Gln Glu Arg Pro Thr Ile Leu Lys Ser Thr Ala Phe
545                 550                 555


<210> SEQ ID NO 7
<211> LENGTH: 555
<212> TYPE: PRT
<213> ORGANISM: Homo sapiens

<400> SEQUENCE: 7

Met Pro Thr Thr Val Asp Asp Val Leu Glu His Gly Gly Glu Phe His
1               5                   10                  15
```

-continued

```
Phe Phe Gln Lys Gln Met Phe Phe Leu Leu Ala Leu Leu Ser Ala Thr
            20                  25                  30

Phe Ala Pro Ile Tyr Val Gly Ile Val Phe Leu Gly Phe Thr Pro Asp
        35                  40                  45

His Arg Cys Arg Ser Pro Gly Val Ala Glu Leu Ser Leu Arg Cys Gly
    50                  55                  60

Trp Ser Pro Ala Glu Glu Leu Asn Tyr Thr Val Pro Gly Pro Gly Pro
65                  70                  75                  80

Ala Gly Glu Ala Ser Pro Arg Gln Cys Arg Arg Tyr Glu Val Asp Trp
                85                  90                  95

Asn Gln Ser Thr Phe Asp Cys Val Asp Pro Leu Ala Ser Leu Asp Thr
            100                 105                 110

Asn Arg Ser Arg Leu Pro Leu Gly Pro Cys Arg Asp Gly Trp Val Tyr
        115                 120                 125

Glu Thr Pro Gly Ser Ser Ile Val Thr Glu Phe Asn Leu Val Cys Ala
    130                 135                 140

Asn Ser Trp Met Leu Asp Leu Phe Gln Ser Ser Val Asn Val Gly Phe
145                 150                 155                 160

Phe Ile Gly Ser Met Ser Ile Gly Tyr Ile Ala Asp Arg Phe Gly Arg
                165                 170                 175

Lys Leu Cys Leu Leu Thr Thr Val Leu Ile Asn Ala Ala Ala Gly Val
            180                 185                 190

Leu Met Ala Ile Ser Pro Thr Tyr Thr Trp Met Leu Ile Phe Arg Leu
        195                 200                 205

Ile Gln Gly Leu Val Ser Lys Ala Gly Trp Leu Ile Gly Tyr Ile Leu
    210                 215                 220

Ile Thr Glu Phe Val Gly Arg Arg Tyr Arg Arg Thr Val Gly Ile Phe
225                 230                 235                 240

Tyr Gln Val Ala Tyr Thr Val Gly Leu Leu Val Leu Ala Gly Val Ala
                245                 250                 255

Tyr Ala Leu Pro His Trp Arg Trp Leu Gln Phe Thr Val Ala Leu Pro
            260                 265                 270

Asn Phe Phe Phe Leu Leu Tyr Tyr Trp Cys Ile Pro Glu Ser Pro Arg
        275                 280                 285

Trp Leu Ile Ser Gln Asn Lys Asn Ala Glu Ala Met Arg Ile Ile Lys
    290                 295                 300

His Ile Ala Lys Lys Asn Gly Lys Ser Leu Pro Ala Ser Leu Gln Arg
305                 310                 315                 320

Leu Arg Leu Glu Glu Glu Thr Gly Lys Lys Leu Asn Pro Ser Phe Leu
                325                 330                 335

Asp Leu Val Arg Thr Pro Gln Ile Arg Lys His Thr Met Ile Leu Met
            340                 345                 350

Tyr Asn Trp Phe Thr Ser Ser Val Leu Tyr Gln Gly Leu Ile Met His
        355                 360                 365

Met Gly Leu Ala Gly Asp Asn Ile Tyr Leu Asp Phe Phe Tyr Ser Ala
    370                 375                 380

Leu Val Glu Phe Pro Ala Ala Phe Met Ile Ile Leu Thr Ile Asp Arg
385                 390                 395                 400

Ile Gly Arg Arg Tyr Pro Trp Ala Ala Ser Asn Met Val Ala Gly Ala
                405                 410                 415

Ala Cys Leu Ala Ser Val Phe Ile Pro Gly Asp Leu Gln Trp Leu Lys
            420                 425                 430
```

-continued

```
Ile Ile Ile Ser Cys Leu Gly Arg Met Gly Ile Thr Met Ala Tyr Glu
        435                 440                 445

Ile Val Cys Leu Val Asn Ala Glu Leu Tyr Pro Thr Phe Ile Arg Asn
    450                 455                 460

Leu Gly Val His Ile Cys Ser Ser Met Cys Asp Ile Gly Gly Ile Ile
465                 470                 475                 480

Thr Pro Phe Leu Val Tyr Arg Leu Thr Asn Ile Trp Leu Glu Leu Pro
                485                 490                 495

Leu Met Val Phe Gly Val Leu Gly Leu Val Ala Gly Gly Leu Val Leu
            500                 505                 510

Leu Leu Pro Glu Thr Lys Gly Lys Ala Leu Pro Glu Thr Ile Glu Glu
        515                 520                 525

Ala Glu Asn Met Gln Arg Pro Arg Lys Asn Lys Glu Lys Met Ile Tyr
    530                 535                 540

Leu Gln Val Gln Lys Leu Asp Ile Pro Leu Asn
545                 550                 555


<210> SEQ ID NO 8
<211> LENGTH: 554
<212> TYPE: PRT
<213> ORGANISM: Homo sapiens

<400> SEQUENCE: 8

Met Pro Thr Val Asp Asp Ile Leu Glu Gln Val Gly Glu Ser Gly Trp
1               5                   10                  15

Phe Gln Lys Gln Ala Phe Leu Ile Leu Cys Leu Leu Ser Ala Ala Phe
            20                  25                  30

Ala Pro Ile Cys Val Gly Ile Val Phe Leu Gly Phe Thr Pro Asp His
        35                  40                  45

His Cys Gln Ser Pro Gly Val Ala Glu Leu Ser Gln Arg Cys Gly Trp
    50                  55                  60

Ser Pro Ala Glu Glu Leu Asn Tyr Thr Val Pro Gly Leu Gly Pro Ala
65                  70                  75                  80

Gly Glu Ala Phe Leu Gly Gln Cys Arg Arg Tyr Glu Val Asp Trp Asn
                85                  90                  95

Gln Ser Ala Leu Ser Cys Val Asp Pro Leu Ala Ser Leu Ala Thr Asn
            100                 105                 110

Arg Ser His Leu Pro Leu Gly Pro Cys Gln Asp Gly Trp Val Tyr Asp
        115                 120                 125

Thr Pro Gly Ser Ser Ile Val Thr Glu Phe Asn Leu Val Cys Ala Asp
    130                 135                 140

Ser Trp Lys Leu Asp Leu Phe Gln Ser Cys Leu Asn Ala Gly Phe Leu
145                 150                 155                 160

Phe Gly Ser Leu Gly Val Gly Tyr Phe Ala Asp Arg Phe Gly Arg Lys
                165                 170                 175

Leu Cys Leu Leu Gly Thr Val Leu Val Asn Ala Val Ser Gly Val Leu
            180                 185                 190

Met Ala Phe Ser Pro Asn Tyr Met Ser Met Leu Leu Phe Arg Leu Leu
        195                 200                 205

Gln Gly Leu Val Ser Lys Gly Asn Trp Met Ala Gly Tyr Thr Leu Ile
    210                 215                 220

Thr Glu Phe Val Gly Ser Gly Ser Arg Arg Thr Val Ala Ile Met Tyr
225                 230                 235                 240

Gln Met Ala Phe Thr Val Gly Leu Val Ala Leu Thr Gly Leu Ala Tyr
                245                 250                 255
```

-continued

```
Ala Leu Pro His Trp Arg Trp Leu Gln Leu Ala Val Ser Leu Pro Thr
            260                 265                 270

Phe Leu Phe Leu Leu Tyr Tyr Trp Cys Val Pro Glu Ser Pro Arg Trp
        275                 280                 285

Leu Leu Ser Gln Lys Arg Asn Thr Glu Ala Ile Lys Ile Met Asp His
    290                 295                 300

Ile Ala Gln Lys Asn Gly Lys Leu Pro Pro Ala Asp Leu Lys Met Leu
305                 310                 315                 320

Ser Leu Glu Glu Asp Val Thr Glu Lys Leu Ser Pro Ser Phe Ala Asp
                325                 330                 335

Leu Phe Arg Thr Pro Arg Leu Arg Lys Arg Thr Phe Ile Leu Met Tyr
            340                 345                 350

Leu Trp Phe Thr Asp Ser Val Leu Tyr Gln Gly Leu Ile Leu His Met
        355                 360                 365

Gly Ala Thr Ser Gly Asn Leu Tyr Leu Asp Phe Leu Tyr Ser Ala Leu
    370                 375                 380

Val Glu Ile Pro Gly Ala Phe Ile Ala Leu Ile Thr Ile Asp Arg Val
385                 390                 395                 400

Gly Arg Ile Tyr Pro Met Ala Met Ser Asn Leu Leu Ala Gly Ala Ala
                405                 410                 415

Cys Leu Val Met Ile Phe Ile Ser Pro Asp Leu His Trp Leu Asn Ile
            420                 425                 430

Ile Ile Met Cys Val Gly Arg Met Gly Ile Thr Ile Ala Ile Gln Met
        435                 440                 445

Ile Cys Leu Val Asn Ala Glu Leu Tyr Pro Thr Phe Val Arg Asn Leu
    450                 455                 460

Gly Val Met Val Cys Ser Ser Leu Cys Asp Ile Gly Gly Ile Ile Thr
465                 470                 475                 480

Pro Phe Ile Val Phe Arg Leu Arg Glu Val Trp Gln Ala Leu Pro Leu
                485                 490                 495

Ile Leu Phe Ala Val Leu Gly Leu Leu Ala Ala Gly Val Thr Leu Leu
            500                 505                 510

Leu Pro Glu Thr Lys Gly Val Ala Leu Pro Glu Thr Met Lys Asp Ala
        515                 520                 525

Glu Asn Leu Gly Arg Lys Ala Lys Pro Lys Glu Asn Thr Ile Tyr Leu
    530                 535                 540

Lys Val Gln Thr Ser Glu Pro Ser Gly Thr
545                 550


<210> SEQ ID NO 9
<211> LENGTH: 539
<212> TYPE: PRT
<213> ORGANISM: Homo sapiens

<400> SEQUENCE: 9

Met Ala Phe Glu Glu Leu Leu Ser Gln Val Gly Gly Leu Gly Arg Phe
1               5                   10                  15

Gln Met Leu His Leu Val Phe Ile Leu Pro Ser Leu Met Leu Leu Ile
            20                  25                  30

Pro His Ile Leu Leu Glu Asn Phe Ala Ala Ala Ile Pro Gly His Arg
        35                  40                  45

Cys Trp Val His Met Leu Asp Asn Asn Thr Gly Ser Gly Asn Glu Thr
    50                  55                  60

Gly Ile Leu Ser Glu Asp Ala Leu Leu Arg Ile Ser Ile Pro Leu Asp
```

-continued

```
65                  70                  75                  80

Ser Asn Leu Arg Pro Glu Lys Cys Arg Phe Phe Val His Pro Gln Trp
                85                  90                  95

Gln Leu Leu His Leu Asn Gly Ile His Ser Thr Ser Glu Ala Asp Thr
            100                 105                 110

Glu Pro Cys Val Asp Gly Trp Val Tyr Asp Gln Ser Tyr Phe Pro Ser
        115                 120                 125

Thr Ile Val Thr Lys Trp Asp Leu Val Cys Asp Tyr Gln Ser Leu Lys
    130                 135                 140

Ser Val Val Gln Phe Leu Leu Leu Thr Gly Met Leu Val Gly Gly Ile
145                 150                 155                 160

Ile His His Gly Val Ser Asp Arg Phe Gly Arg Arg Phe Ile Leu Arg
                165                 170                 175

Trp Cys Leu Leu Gln Leu Ala Ile Thr Asp Thr Cys Ala Ala Phe Ala
            180                 185                 190

Pro Thr Phe Pro Val Tyr Cys Val Leu Arg Phe Leu Ala Gly Phe Ser
        195                 200                 205

Ser Met Ile Ile Ile Ser Asn Asn Ser Leu Pro Ile Thr Glu Trp Ile
    210                 215                 220

Arg Pro Asn Ser Lys Ala Leu Val Val Ile Leu Ser Ser Gly Ala Leu
225                 230                 235                 240

Ser Ile Gly Gln Ile Ile Leu Gly Gly Leu Ala Tyr Val Phe Arg Asp
                245                 250                 255

Trp Gln Thr Leu His Val Val Ala Ser Val Pro Phe Leu Gly Leu Leu
            260                 265                 270

Leu Leu Gln Arg Trp Leu Val Glu Ser Ala Arg Trp Leu Ile Ile Thr
        275                 280                 285

Asn Lys Leu Asp Glu Gly Leu Lys Ala Leu Arg Lys Val Ala Arg Thr
    290                 295                 300

Asn Gly Ile Lys Asn Ala Glu Glu Thr Leu Asn Ile Glu Val Val Arg
305                 310                 315                 320

Ser Thr Met Gln Glu Glu Leu Asp Ala Ala Gln Thr Lys Thr Thr Val
                325                 330                 335

Cys Asp Leu Phe Arg Asn Pro Ser Met Arg Lys Arg Ile Cys Ile Leu
            340                 345                 350

Val Phe Leu Arg Phe Ala Asn Thr Ile Pro Phe Tyr Gly Thr Met Val
        355                 360                 365

Asn Leu Gln His Val Gly Ser Asn Ile Phe Leu Leu Gln Val Leu Tyr
    370                 375                 380

Gly Ala Val Ala Leu Ile Val Arg Cys Leu Ala Leu Leu Thr Leu Asn
385                 390                 395                 400

His Met Gly Arg Arg Ile Ser Gln Ile Leu Phe Met Phe Leu Val Gly
                405                 410                 415

Leu Ser Ile Leu Ala Asn Thr Phe Val Pro Lys Glu Met Gln Thr Leu
            420                 425                 430

Arg Val Ala Leu Ala Cys Leu Gly Ile Gly Cys Ser Ala Ala Thr Phe
        435                 440                 445

Ser Ser Val Ala Val His Phe Ile Glu Leu Ile Pro Thr Val Leu Arg
    450                 455                 460

Ala Arg Ala Ser Gly Ile Asp Leu Thr Ala Ser Arg Ile Gly Ala Ala
465                 470                 475                 480

Leu Pro Leu Leu Met Thr Leu Thr Val Phe Phe Thr Thr Leu Pro Trp
                485                 490                 495
```

```
Ile Ile Tyr Gly Ile Phe Pro Ile Ile Gly Gly Leu Ile Val Phe Leu
            500                 505                 510

Leu Pro Glu Thr Lys Asn Leu Pro Leu Pro Asp Thr Ile Lys Asp Val
        515                 520                 525

Glu Asn Gln Lys Lys Asn Leu Lys Glu Lys Ala
    530                 535


<210> SEQ ID NO 10
<211> LENGTH: 550
<212> TYPE: PRT
<213> ORGANISM: Homo sapiens

<400> SEQUENCE: 10

Met Ala Phe Ser Lys Leu Leu Glu Gln Ala Gly Gly Val Gly Leu Phe
1               5                   10                  15

Gln Thr Leu Gln Val Leu Thr Phe Ile Leu Pro Cys Leu Met Ile Pro
            20                  25                  30

Ser Gln Met Leu Leu Glu Asn Phe Ser Ala Ala Ile Pro Gly His Arg
        35                  40                  45

Cys Trp Thr His Met Leu Asp Asn Gly Ser Ala Val Ser Thr Asn Met
    50                  55                  60

Thr Pro Lys Ala Leu Leu Thr Ile Ser Ile Pro Pro Gly Pro Asn Gln
65                  70                  75                  80

Gly Pro His Gln Cys Arg Arg Phe Arg Gln Pro Gln Trp Gln Leu Leu
                85                  90                  95

Asp Pro Asn Ala Thr Ala Thr Ser Trp Ser Glu Ala Asp Thr Glu Pro
            100                 105                 110

Cys Val Asp Gly Trp Val Tyr Asp Arg Ser Val Phe Thr Ser Thr Ile
        115                 120                 125

Val Ala Lys Trp Asp Leu Val Cys Ser Ser Gln Gly Leu Lys Pro Leu
    130                 135                 140

Ser Gln Ser Ile Phe Met Ser Gly Ile Leu Val Gly Ser Phe Ile Trp
145                 150                 155                 160

Gly Leu Leu Ser Tyr Arg Phe Gly Arg Lys Pro Met Leu Ser Trp Cys
                165                 170                 175

Cys Leu Gln Leu Ala Val Ala Gly Thr Ser Thr Ile Phe Ala Pro Thr
            180                 185                 190

Phe Val Ile Tyr Cys Gly Leu Arg Phe Val Ala Ala Phe Gly Met Ala
        195                 200                 205

Gly Ile Phe Leu Ser Ser Leu Thr Leu Met Val Glu Trp Thr Thr Thr
    210                 215                 220

Ser Arg Arg Ala Val Thr Met Thr Val Val Gly Cys Ala Phe Ser Ala
225                 230                 235                 240

Gly Gln Ala Ala Leu Gly Gly Leu Ala Phe Ala Leu Arg Asp Trp Arg
                245                 250                 255

Thr Leu Gln Leu Ala Ala Ser Val Pro Phe Phe Ala Ile Ser Leu Ile
            260                 265                 270

Ser Trp Trp Leu Pro Glu Ser Ala Arg Trp Leu Ile Ile Lys Gly Lys
        275                 280                 285

Pro Asp Gln Ala Leu Gln Glu Leu Arg Lys Val Ala Arg Ile Asn Gly
    290                 295                 300

His Lys Glu Ala Lys Asn Leu Thr Ile Glu Val Leu Met Ser Ser Val
305                 310                 315                 320

Lys Glu Glu Val Ala Ser Ala Lys Glu Pro Arg Ser Val Leu Asp Leu
```

-continued

```
                325                 330                 335

Phe Cys Val Pro Val Leu Arg Trp Arg Ser Cys Ala Met Leu Val Val
            340                 345                 350

Asn Phe Ser Leu Leu Ile Ser Tyr Tyr Gly Leu Val Phe Asp Leu Gln
        355                 360                 365

Ser Leu Gly Arg Asp Ile Phe Leu Leu Gln Ala Leu Phe Gly Ala Val
    370                 375                 380

Asp Phe Leu Gly Arg Ala Thr Thr Ala Leu Leu Leu Ser Phe Leu Gly
385                 390                 395                 400

Arg Arg Thr Ile Gln Ala Gly Ser Gln Ala Met Ala Gly Leu Ala Ile
                405                 410                 415

Leu Ala Asn Met Leu Val Pro Gln Asp Leu Gln Thr Leu Arg Val Val
            420                 425                 430

Phe Ala Val Leu Gly Lys Gly Cys Phe Gly Ile Ser Leu Thr Cys Leu
        435                 440                 445

Thr Ile Tyr Lys Ala Glu Leu Phe Pro Thr Pro Val Arg Met Thr Ala
    450                 455                 460

Asp Gly Ile Leu His Thr Val Gly Arg Leu Gly Ala Met Met Gly Pro
465                 470                 475                 480

Leu Ile Leu Met Ser Arg Gln Ala Leu Pro Leu Leu Pro Pro Leu Leu
                485                 490                 495

Tyr Gly Val Ile Ser Ile Ala Ser Ser Leu Val Val Leu Phe Phe Leu
            500                 505                 510

Pro Glu Thr Gln Gly Leu Pro Leu Pro Asp Thr Ile Gln Asp Leu Glu
        515                 520                 525

Ser Gln Lys Ser Thr Ala Ala Gln Gly Asn Arg Gln Glu Ala Val Thr
    530                 535                 540

Val Glu Ser Thr Ser Leu
545                 550


<210> SEQ ID NO 11
<211> LENGTH: 542
<212> TYPE: PRT
<213> ORGANISM: Homo sapiens

<400> SEQUENCE: 11

Met Thr Phe Ser Glu Ile Leu Asp Arg Val Gly Ser Met Gly His Phe
1               5                   10                  15

Gln Phe Leu His Val Ala Ile Leu Gly Leu Pro Ile Leu Asn Met Ala
            20                  25                  30

Asn His Asn Leu Leu Gln Ile Phe Thr Ala Ala Thr Pro Val His His
        35                  40                  45

Cys Arg Pro Pro His Asn Ala Ser Thr Gly Pro Trp Val Leu Pro Met
    50                  55                  60

Gly Pro Asn Gly Lys Pro Glu Arg Cys Leu Arg Phe Val His Pro Pro
65                  70                  75                  80

Asn Ala Ser Leu Pro Asn Asp Thr Gln Arg Ala Met Glu Pro Cys Leu
                85                  90                  95

Asp Gly Trp Val Tyr Asn Ser Thr Lys Asp Ser Ile Val Thr Glu Trp
            100                 105                 110

Asp Leu Val Cys Asn Ser Asn Lys Leu Lys Glu Met Ala Gln Ser Ile
        115                 120                 125

Phe Met Ala Gly Ile Leu Ile Gly Gly Leu Val Leu Gly Asp Leu Ser
    130                 135                 140
```

-continued

```
Asp Arg Phe Gly Arg Arg Pro Ile Leu Thr Cys Ser Tyr Leu Leu Leu
145                 150                 155                 160

Ala Ala Ser Gly Ser Gly Ala Ala Phe Ser Pro Thr Phe Pro Ile Tyr
                165                 170                 175

Met Val Phe Arg Phe Leu Cys Gly Phe Gly Ile Ser Gly Ile Thr Leu
            180                 185                 190

Ser Thr Val Ile Leu Asn Val Glu Trp Val Pro Thr Arg Met Arg Ala
        195                 200                 205

Ile Met Ser Thr Ala Leu Gly Tyr Cys Tyr Thr Phe Gly Gln Phe Ile
    210                 215                 220

Leu Pro Gly Leu Ala Tyr Ala Ile Pro Gln Trp Arg Trp Leu Gln Leu
225                 230                 235                 240

Thr Val Ser Ile Pro Phe Phe Val Phe Phe Leu Ser Ser Trp Trp Thr
                245                 250                 255

Pro Glu Ser Ile Arg Trp Leu Val Leu Ser Gly Lys Ser Ser Glu Ala
            260                 265                 270

Leu Lys Ile Leu Arg Arg Val Ala Val Phe Asn Gly Lys Lys Glu Glu
        275                 280                 285

Gly Glu Arg Leu Ser Leu Glu Glu Leu Lys Leu Asn Leu Gln Lys Glu
    290                 295                 300

Ile Ser Leu Ala Lys Ala Lys Tyr Thr Ala Ser Asp Leu Phe Arg Ile
305                 310                 315                 320

Pro Met Leu Arg Arg Met Thr Phe Cys Leu Ser Leu Ala Trp Phe Ala
                325                 330                 335

Thr Gly Phe Ala Tyr Tyr Ser Leu Ala Met Gly Val Glu Glu Phe Gly
            340                 345                 350

Val Asn Leu Tyr Ile Leu Gln Ile Ile Phe Gly Gly Val Asp Val Pro
        355                 360                 365

Ala Lys Phe Ile Thr Ile Leu Ser Leu Ser Tyr Leu Gly Arg His Thr
    370                 375                 380

Thr Gln Ala Ala Ala Leu Leu Leu Ala Gly Gly Ala Ile Leu Ala Leu
385                 390                 395                 400

Thr Phe Val Pro Leu Asp Leu Gln Thr Val Arg Thr Val Leu Ala Val
                405                 410                 415

Phe Gly Lys Gly Cys Leu Ser Ser Ser Phe Ser Cys Leu Phe Leu Tyr
            420                 425                 430

Thr Ser Glu Leu Tyr Pro Thr Val Ile Arg Gln Thr Gly Met Gly Val
        435                 440                 445

Ser Asn Leu Trp Thr Arg Val Gly Ser Met Val Ser Pro Leu Val Lys
    450                 455                 460

Ile Thr Gly Glu Val Gln Pro Phe Ile Pro Asn Ile Ile Tyr Gly Ile
465                 470                 475                 480

Thr Ala Leu Leu Gly Gly Ser Ala Ala Leu Phe Leu Pro Glu Thr Leu
                485                 490                 495

Asn Gln Pro Leu Pro Glu Thr Ile Glu Asp Leu Glu Asn Trp Ser Leu
            500                 505                 510

Arg Ala Lys Lys Pro Lys Gln Glu Pro Glu Val Glu Lys Ala Ser Gln
        515                 520                 525

Arg Ile Pro Leu Gln Pro His Gly Pro Gly Leu Gly Ser Ser
    530                 535                 540
```

<210> SEQ ID NO 12
<211> LENGTH: 550
<212> TYPE: PRT

-continued

<213> ORGANISM: Homo sapiens

<400> SEQUENCE: 12

```
Met Ala Phe Asn Asp Leu Leu Gln Gln Val Gly Gly Val Gly Arg Phe
1               5                   10                  15

Gln Gln Ile Gln Val Thr Leu Val Val Leu Pro Leu Leu Leu Met Ala
            20                  25                  30

Ser His Asn Thr Leu Gln Asn Phe Thr Ala Ala Ile Pro Thr His His
        35                  40                  45

Cys Arg Pro Pro Ala Asp Ala Asn Leu Ser Lys Asn Gly Gly Leu Glu
    50                  55                  60

Val Trp Leu Pro Arg Asp Arg Gln Gly Gln Pro Glu Ser Cys Leu Arg
65                  70                  75                  80

Phe Thr Ser Pro Gln Trp Gly Leu Pro Phe Leu Asn Gly Thr Glu Ala
                85                  90                  95

Asn Gly Thr Gly Ala Thr Glu Pro Cys Thr Asp Gly Trp Ile Tyr Asp
            100                 105                 110

Asn Ser Thr Phe Pro Ser Thr Ile Val Thr Glu Trp Asp Leu Val Cys
        115                 120                 125

Ser His Arg Ala Leu Arg Gln Leu Ala Gln Ser Leu Tyr Met Val Gly
    130                 135                 140

Val Leu Leu Gly Ala Met Val Phe Gly Tyr Leu Ala Asp Arg Leu Gly
145                 150                 155                 160

Arg Arg Lys Val Leu Ile Leu Asn Tyr Leu Gln Thr Ala Val Ser Gly
                165                 170                 175

Thr Cys Ala Ala Phe Ala Pro Asn Phe Pro Ile Tyr Cys Ala Phe Arg
            180                 185                 190

Leu Leu Ser Gly Met Ala Leu Ala Gly Ile Ser Leu Asn Cys Met Thr
        195                 200                 205

Leu Asn Val Glu Trp Met Pro Ile His Thr Arg Ala Cys Val Gly Thr
    210                 215                 220

Leu Ile Gly Tyr Val Tyr Ser Leu Gly Gln Phe Leu Leu Ala Gly Val
225                 230                 235                 240

Ala Tyr Ala Val Pro His Trp Arg His Leu Gln Leu Leu Val Ser Ala
                245                 250                 255

Pro Phe Phe Ala Phe Phe Ile Tyr Ser Trp Phe Phe Ile Glu Ser Ala
            260                 265                 270

Arg Trp His Ser Ser Ser Gly Arg Leu Asp Leu Thr Leu Arg Ala Leu
        275                 280                 285

Gln Arg Val Ala Arg Ile Asn Gly Lys Arg Glu Glu Gly Ala Lys Leu
    290                 295                 300

Ser Met Glu Val Leu Arg Ala Ser Leu Gln Lys Glu Leu Thr Met Gly
305                 310                 315                 320

Lys Gly Gln Ala Ser Ala Met Glu Leu Leu Arg Cys Pro Thr Leu Arg
                325                 330                 335

His Leu Phe Leu Cys Leu Ser Met Leu Trp Phe Ala Thr Ser Phe Ala
            340                 345                 350

Tyr Tyr Gly Leu Val Met Asp Leu Gln Gly Phe Gly Val Ser Ile Tyr
        355                 360                 365

Leu Ile Gln Val Ile Phe Gly Ala Val Asp Leu Pro Ala Lys Leu Val
    370                 375                 380

Gly Phe Leu Val Ile Asn Ser Leu Gly Arg Arg Pro Ala Gln Met Ala
385                 390                 395                 400
```

-continued

```
Ala Leu Leu Leu Ala Gly Ile Cys Ile Leu Leu Asn Gly Val Ile Pro
                405                 410                 415

Gln Asp Gln Ser Ile Val Arg Thr Ser Leu Ala Val Leu Gly Lys Gly
            420                 425                 430

Cys Leu Ala Ala Ser Phe Asn Cys Ile Phe Leu Tyr Thr Gly Glu Leu
        435                 440                 445

Tyr Pro Thr Met Ile Arg Gln Thr Gly Met Gly Met Gly Ser Thr Met
    450                 455                 460

Ala Arg Val Gly Ser Ile Val Ser Pro Leu Val Ser Met Thr Ala Glu
465                 470                 475                 480

Leu Tyr Pro Ser Met Pro Leu Phe Ile Tyr Gly Ala Val Pro Val Ala
                485                 490                 495

Ala Ser Ala Val Thr Val Leu Leu Pro Glu Thr Leu Gly Gln Pro Leu
            500                 505                 510

Pro Asp Thr Val Gln Asp Leu Glu Ser Arg Lys Gly Lys Gln Thr Arg
        515                 520                 525

Gln Gln Gln Glu His Gln Lys Tyr Met Val Pro Leu Gln Ala Ser Ala
    530                 535                 540

Gln Glu Lys Asn Gly Leu
545                 550


<210> SEQ ID NO 13
<211> LENGTH: 24
<212> TYPE: DNA
<213> ORGANISM: Artificial Sequence
<220> FEATURE:
<223> OTHER INFORMATION: Chemically synthesized

<400> SEQUENCE: 13

ggcacattta ttcaccaaga ccag                                            24


<210> SEQ ID NO 14
<211> LENGTH: 24
<212> TYPE: DNA
<213> ORGANISM: Artificial Sequence
<220> FEATURE:
<223> OTHER INFORMATION: Chemically synthesized

<400> SEQUENCE: 14

tgtggacctc agcagcattt ggat                                            24
```